US007307104B2

(12) United States Patent
Qiu et al.

(10) Patent No.: US 7,307,104 B2
(45) Date of Patent: *Dec. 11, 2007

(54) PROCESS FOR FORMING AN EMULSION USING MICROCHANNEL PROCESS TECHNOLOGY

(75) Inventors: Dongming Qiu, Dublin, OH (US); Anna Lee Tonkovich, Marysville, OH (US); Laura J. Silva, Dublin, OH (US); Richard Q. Long, Columbus, OH (US); Barry L. Yang, Dublin, OH (US); Kristina Marie Trenkamp, Dublin, OH (US); Jennifer Anne Freeman, Columbus, OH (US)

(73) Assignee: Velocys, Inc., Plain City, OH (US)

( * ) Notice: Subject to any disclaimer, the term of this patent is extended or adjusted under 35 U.S.C. 154(b) by 338 days.

This patent is subject to a terminal disclaimer.

(21) Appl. No.: 10/844,061

(22) Filed: May 12, 2004

(65) Prior Publication Data

US 2004/0234566 A1 Nov. 25, 2004

Related U.S. Application Data

(63) Continuation-in-part of application No. 10/440,056, filed on May 16, 2003.

(60) Provisional application No. 60/548,152, filed on Feb. 25, 2004.

(51) Int. Cl.
B01F 3/08 (2006.01)
B01F 17/00 (2006.01)

(52) U.S. Cl. .............................. 516/54; 516/21; 516/22; 516/23; 516/928

(58) Field of Classification Search .................. 516/21, 516/22, 53, 54, 928
See application file for complete search history.

(56) References Cited

U.S. PATENT DOCUMENTS

| | | | | |
|---|---|---|---|---|
| 3,489,690 A | | 1/1970 | Lachampt et al. ........... 252/308 |
| 4,303,456 A | * | 12/1981 | Schmuck et al. .............. 156/78 |
| 4,392,362 A | | 7/1983 | Little ........................... 62/514 |
| 4,461,777 A | * | 7/1984 | Murase et al. ............ 426/330.6 |
| 4,516,632 A | | 5/1985 | Swift et al. .................. 165/167 |
| 5,075,113 A | | 12/1991 | DuBois ....................... 424/450 |
| 5,304,334 A | * | 4/1994 | Lahanas et al. ................ 516/23 |
| 5,309,637 A | | 5/1994 | Moriarty ................. 29/890.054 |
| 5,317,805 A | | 6/1994 | Hoopman et al. ........ 29/890.03 |
| 5,611,214 A | | 3/1997 | Wegeng et al. ................ 62/498 |
| 5,727,618 A | | 3/1998 | Mundinger et al. ......... 165/80.4 |
| 5,811,062 A | | 9/1998 | Wegeng et al. .............. 422/129 |
| 5,858,314 A | | 1/1999 | Hsu et al. .................... 422/211 |
| 6,126,723 A | | 10/2000 | Drost et al. ...................... 96/4 |
| 6,129,973 A | | 10/2000 | Martin et al. ................ 428/166 |
| 6,155,710 A | | 12/2000 | Nakajima et al. ......... 366/167.1 |
| 6,192,596 B1 | | 2/2001 | Bennett et al. .................. 34/76 |
| 6,200,536 B1 | | 3/2001 | Tonkovich et al. .......... 422/177 |
| 6,203,791 B1 | | 3/2001 | Protopapa et al. ........ 424/94.64 |
| 6,216,343 B1 | | 4/2001 | Leland et al. ........... 29/890.032 |
| 6,220,497 B1 | | 4/2001 | Benz et al. ................... 228/118 |
| 6,230,408 B1 | | 5/2001 | Ehrfeld et al. .......... 29/890.039 |
| 6,258,858 B1 | | 7/2001 | Nakajima et al. .............. 516/73 |
| 6,281,254 B1 | | 8/2001 | Nakajima et al. .............. 516/53 |
| 6,313,393 B1 | | 11/2001 | Drost .......................... 136/201 |
| 6,352,577 B1 | | 3/2002 | Martin et al. ..................... 96/4 |
| 6,381,846 B2 | | 5/2002 | Insley et al. ........... 29/890.039 |
| 6,387,301 B1 | | 5/2002 | Nakajima et al. ............. 265/4.4 |
| 6,415,860 B1 | | 7/2002 | Kelly et al. .................. 165/748 |
| 6,431,695 B1 | | 8/2002 | Johnston et al. ............... 347/86 |
| 6,457,854 B1 | | 10/2002 | Koop et al. .................. 366/336 |
| 6,488,838 B1 | | 12/2002 | Tonkovich et al. .......... 208/108 |
| 6,540,975 B2 | | 4/2003 | Tonkovich et al. .......... 423/659 |
| 6,546,998 B2 | | 4/2003 | Oh et al. ...................... 165/110 |
| 6,675,875 B1 | | 1/2004 | Vafai et al. .................. 165/80.4 |
| 6,746,819 B1 | | 6/2004 | Schmitz et al. ........... 430/272.1 |
| 6,747,178 B1 | | 6/2004 | Harston et al. .............. 570/175 |
| 6,749,814 B1 | | 6/2004 | Bergh et al. ................. 422/130 |
| 6,749,817 B1 | | 6/2004 | Mulvaney, III ............. 422/200 |
| 6,755,211 B1 | | 6/2004 | O'Connor et al. ........... 137/554 |
| 6,769,444 B2 | | 8/2004 | Guzman et al. .......... 137/15.01 |

(Continued)

FOREIGN PATENT DOCUMENTS

EP 1 125 630 A2 8/2001

(Continued)

OTHER PUBLICATIONS

Gneist et al.; "Droplet Formation in Liquid/Liquid Systems Using High Frequency AC Fields"; Chem-Eng. Technol. 25 (2002) 2; pp. 129133.

Vladisavljevic et al.; "Preparation and Analysis of Oil-in-Water Emulsions with a Narrow Droplet Size Distribution using Shirasu-porous-glass (SPG) Membranes", Presented at the International Congress on Membranes and Membrane Processes (ICOM), Toulouse, France, Jul. 7-12, 2002.

Sugiura et al.; "Characterization of Spontaneous Transformation-Based Droplet Formation During Microchannel Emulsification"; J. Phys. Chem B 2002, 106, 9405-9406.

Tong et al.; "Surfactant Effect on Production of Monodispersed Microspheres by Microchannel Emulsification Method"; Journal of Surfactants and Detergents, vol. 3, No. 3 (Jul. 2000).

(Continued)

Primary Examiner—Randy Gulakowski
Assistant Examiner—Timothy J. Kugel
(74) Attorney, Agent, or Firm—Renner, Otto, Boisselle & Sklar, LLP

(57) ABSTRACT

The disclosed invention relates to a process for making an emulsion. The process comprises: flowing a first liquid through a process microchannel, the process microchannel having a wall with an apertured section; flowing a second liquid through the apertured section into the process microchannel in contact with the first liquid, the first liquid forming a continuous phase, the second liquid forming a discontinuous phase dispersed in the continuous phase.

112 Claims, 21 Drawing Sheets

U.S. PATENT DOCUMENTS

| | | | |
|---|---|---|---|
| 6,770,245 B2 | 8/2004 | Akporiaye et al. | 422/82.12 |
| 6,773,684 B2 | 8/2004 | Lesieur et al. | 422/198 |
| 6,916,113 B2 | 7/2005 | Van de Goor et al. | 366/108 |
| 6,935,768 B2 | 8/2005 | Lowe et al. | 366/167.1 |
| 6,935,772 B2 | 8/2005 | Karp et al. | 366/341 |
| 6,969,764 B2 | 11/2005 | Krull et al. | 526/64 |
| 7,001,576 B2 | 2/2006 | Hohmann et al. | 422/224 |
| 2002/0071797 A1 | 6/2002 | Loffler et al. | 422/190 |
| 2003/0027858 A1 | 2/2003 | Lambert et al. | 514/458 |
| 2003/0190563 A1 | 10/2003 | Nagasawa et al. | 430/569 |
| 2004/0011413 A1 | 1/2004 | Fujii et al. | 137/896 |
| 2004/0027915 A1 | 2/2004 | Lowe et al. | 366/341 |
| 2004/0029977 A1 | 2/2004 | Kawa et al. | 514/786 |
| 2004/0037161 A1 | 2/2004 | Honda et al. | 366/176.1 |
| 2004/0104010 A1 | 6/2004 | Kenny et al. | 165/80.4 |
| 2004/0123626 A1 | 7/2004 | Caze et al. | 65/17.2 |
| 2004/0125689 A1 | 7/2004 | Ehrfeld et al. | 366/165.1 |
| 2004/0130057 A1 | 7/2004 | Mehrabi et al. | 264/171.13 |
| 2004/0131345 A1 | 7/2004 | Kylberg et al. | 392/465 |
| 2004/0131507 A1 | 7/2004 | Saitmacher et al. | 422/111 |
| 2004/0131829 A1 | 7/2004 | Joseph et al. | 428/166 |
| 2004/0136902 A1 | 7/2004 | Plath et al. | 423/651 |
| 2004/0141893 A1 | 7/2004 | Martin | 422/198 |
| 2004/0143059 A1 | 7/2004 | Cabrera | 524/800 |
| 2004/0144421 A1 | 7/2004 | Parce et al. | 137/14 |
| 2004/0156762 A1 | 8/2004 | Schuppich et al. | 422/191 |
| 2005/0152690 A1 | 7/2005 | Nagasawa et al. | 396/142 |
| 2005/0161326 A1 | 7/2005 | Morita et al. | 204/450 |
| 2005/0233040 A1 | 10/2005 | Ehrfeld et al. | 426/518 |
| 2005/0279491 A1 | 12/2005 | Thome et al. | 165/272 |
| 2006/0077755 A1 | 4/2006 | Higuchi et al. | 366/336 |
| 2006/0121122 A1 | 6/2006 | Nakajima et al. | 424/490 |
| 2006/0128815 A1 | 6/2006 | Clare et al. | 516/9 |

FOREIGN PATENT DOCUMENTS

| | | |
|---|---|---|
| EP | 1 311 341 B1 | 8/2001 |
| EP | 0 904 608 B1 | 12/2001 |
| EP | 1 171 227 B1 | 6/2003 |
| EP | 1 382 382 A1 | 7/2003 |
| EP | 1 362 634 A1 | 11/2003 |
| EP | 1 180 062 B1 | 3/2004 |
| EP | 1 390 131 B1 | 7/2005 |
| EP | 1 289 660 B1 | 2/2006 |
| EP | 1 510 251 B1 | 9/2006 |
| JP | 05279523 | 10/2005 |
| JP | 05211857 | 11/2005 |
| JP | 05213334 | 11/2005 |
| WO | 97/32687 | 9/1997 |
| WO | 98/30205 | 7/1998 |
| WO | 98/55812 | 12/1998 |
| WO | 00/06295 | 2/2000 |
| WO | 01/10773 A1 | 2/2001 |
| WO | 01/12312 A2 | 2/2001 |
| WO | 01/43857 A1 | 6/2001 |
| WO | 01/54807 A1 | 8/2001 |
| WO | 01/95237 A2 | 12/2001 |
| WO | 02/28769 A2 | 4/2002 |
| WO | 03/026788 | 4/2003 |
| WO | 03/068381 A1 | 8/2003 |
| WO | 03/078052 A1 | 9/2003 |
| WO | 03/106386 A2 | 12/2003 |
| WO | 2004/043580 | 5/2004 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067708 | 8/2004 |
| WO | 2005/058477 A1 | 6/2005 |
| WO | 2005/063368 A2 | 7/2005 |
| WO | 2005/077508 A1 | 8/2005 |
| WO | 2005/079964 A1 | 9/2005 |

OTHER PUBLICATIONS

Rudhardt et al.; "Phase switching of ordered arrays of liquid crystal emulsions"; Applied Physics Letters, vol. 82, No. 16; Apr. 21, 2003.

Matlosz et al.; "Microreactors as Tools in Chemical Research"; Microreaction Technology; IMRET 5: Proceedings of the Fifth International Conference on Microreaction Technology (May 27-30, 2001).

Srinivasn et al.; "Micromachined Reactors for Catalytic Partial Oxidation Reactions"; AIChE Journal; Nov. 1997; vol. 43, No. 11; pp. 3059-3069.

TeGrotenhuis et al.; Optimizing Microchannel Reactors by Trading-Off Equilibrium and Reaction Kinetics through Temperature Management; Prepared for presentation at IMRET 6—6th International Conference on Microreaction Technology; Mar. 10-14, 2002.

Wengeng et al.; "Compact Fuel Processors for Fuel Cell Powered Automobiles Based on Microchannel Technology"; Fuel Cells Bulletin No. 28; pp. 8-13.

Rostami et al.; "Flow and Heat Transfer for Gas Flowing in Microchannels: a Review"; Heat and Mass Transfer 38 (2002) 359-367.

Dow Chemical Co.; Dow Dispersion Sciences, Advanced Emulsions through Advanced Science, Improving the Aesthetics of Personal Care Formulations; Published Mar. 2003.

Dow Chemical Co.; Dow Dispersion Sciences, Advanced Emulsions through Advanced Science, A New Approach to Creating Uniquely Functional Cosmetic Formulations; Published Mar. 2003.

Dow Chemical Co.; Dow Dispersion Sciences, Advanced Emulsions through Advanced Science, Creating New Ways for Personal Care Manufacturers to Optimize Operational Efficiency; Published Mar. 2003.

"Preparation of Emulsions Using Porous Membranes in Membrane Contactor"; IGVT Universitat Stuttgart Fraunhofer-Gessellschaft; www.igb.fraunhofer.de/WWW/GF/DP/en/GFDP_22_Emulgieren.en.html. (2002).

Schroder et al.; "Effect of Dynamic Interfacial Tension on the Emulsification Process Using Microporous, Ceramic Membranes"; Journal of Colloid and Interface Science 202, 334-340 (1998).

Beauty-Inn AG, Intesiv-Kosmetikinstitut; Sauerstoff-Spruhkosmetik; www.beauty-inn.ch/Behandlug-Sauerstoff-Spruehkosmetik.htm. (Nov. 2001).

Peng et al.; "Controlled Production of Emulsion Using a Crossflow Membrane"; PACE University of Exeter; www.pace.leeds.ac.uk/projects/p94x7.htm. (Nov. 6, 1997).

nst News; International Activities in Microsystem Technology; Microfluidic Systems New Products; No. 17, Jul./Aug. 1996.

Kawakatsu et al.; Production of W/O/W Emulsions and S/O/W Pectin Microcapsules by Microchannel Emulsification; Colloids and Surfaces; A: Physicochemical and Engineering Aspects 189 (2001) 257-264.

Tenore; "Surfactant-Free Emulsion Systems"; Cosmetic Science & Business 2000; www.atalink.co.uk/csb2000/html/art_rawmats_lipo.htm.

Lin; "Low-Surfactant Emulsification"; J. Soc. Cosmet. Chem., 30, 167-180 (May/Jun. 1979).

Friberg et al.; Emulsions; Kirk-Othmer Encyclopedia of Chemcial Technology; (Dec. 4, 2000) www.mrw.interscience.wiley.com/kirk/articles/emulfrib.a01/sect12.html.

Umbanhowar et al.; "Monodisperse Emulsion Generation via Drop Break Off in A Coflowing Stream"; Langmuir 2000, 16, 347-351.

Besser, Ronald S. "New Directions in Reactor Design Through Miniaturization". Sep. 13, 2002, Tulane Engineering Forum.

Ouyang et al. "Flexible Microreator System for Chemical Research at Moderate and High Temperatures". Stevens Institute of Technology.
Invitation to Pay Additional Fees and Partial International Search Report, Application No. PCT/US2004/014736, mailed Nov. 25, 2004.
International Search Report and Written Opinion, Application No. PCT/US2004/014736, mailed Mar. 7, 2004.
Written Opinion of the International Preliminary Examining Authority; International Application No. PCT/US2004/014736; mailed Aug. 19, 2005.
Iwamoto et al.; "Preparation of Gelatine Microbeads With a Narrow Size Distribution Using Microchannel emulsification"; AAPS PharmSciTech 2002; 3 (3) article 25.
Nakajima; "Novel Microchannel System for Monodispersed Micropheres"; RIKEN Review No. 35 (Jun. 2001); Focused on Science and Technology in Micro-Nano Scale; pp. 21-23.
International Report of Patentability, Application No. PCT/US2004/014736, mailed Sep. 29, 2005.
Nakajima; "Novel microchannel system for monodispersed microspheres"; RIKEN Review No. 36 (Jun. 2001); Focused on Science and Technology in Micro/Nan Scale; pp. 21-23.
Lambrich et al.; "Emulsification using microporous systems"; Journal of Membrane Science 257 (2005); pp. 76-84.
Kiwi-Minsker, et al.; "Microstructured reactors for catalytic reactions"; Catalysis Today 110 (2005); pp. 2-14.
Priest, et al.; "Generation of monodisperse gel emulsions in a microfluidic device"; Applied Physics Letters 88, 024106 (2006).
Abdallah et al.; "Gas-Liquid and gas-liquid-solid catalysts in a mesh microreactor", Chem. Commun., 2004, pp. 372-373.
Angeli et al.; "Modelling of Gas-Liquid Catalytic Reactions in Microchannels"; International Conference on Microreaction Technology (2000), pp. 253-259.
Besser; Stevens Institute of Technology; A Look at Microchemical Systems (Feb. 23, 2006), pp. 1-21.
Boger; "Monolithic Catalysts for the Chemical Industry", Ind. Eng. Chem. Res., 2004, 43, 4602-4611.
Chambers et al.; "Elemental fluorine Part 13. Gas-liquid thin film microreactors for selective direct fluorination"; Lab on a Chip, 2001, 1, 132-137.
Chambers et al.; "Elemental fluorine Part 16. Versatile thin-film-gas-liquid multi-channel microreactors for effective scale-out"; Lab Chip, 2005, 5, 191-198.
Chambers et al. "Elemental fluorine Part 18. Selective direct fluorination of 1,3-ketoesters and 1,3-diketones using gas/liquid microreactor technology"; Lab Chip, 2005, 5, 1132-1139.
Chambers et al.; "Versatile Gas/Liquid Microreactors for Industry"; Chem. Eng. Technol., 2005, 28, No. 3, pp. 344-352.
Commenge et al.; "Gas-phase residence time distribution in a falling-film microreactor"; Chemical Engineering Science 61, 2006, 597-604.
de Bellefon et al.; "Asymmetric catalytic hydrogenations at microlitre scale ina helicoidal single channel falling film micro-reactor"; Catalysis Today 110 (2005), pp. 179-187.
Doku et al.; "On-microchip multiphase chemistry—a review of microreactor design principles and reagent contacting modes"; Tetrahedron 61 (2006), pp. 2733-2742.
McGovern et al.; "Flow Regimes in a Catalyst Trap Microreactor"; Stevens Institute of Technology.
Gunther et al.; "Transport and reaction in microscale segmented gas-liquid flow"; Lab Chip, 2004, 4, pp. 278-286.
Haverkamp et al.; "Characterization of Gas/Liquid Microreactor, the Micro Bubble Column: Determination of Specific Interfacial Area"; International Conference on Microreaction Technology, 2001, pp. 202-214.
Heibel et al.; "Flooding Performance of Square Channel Monolith Structures"; Ind. Eng. Chem. Res. 2002, 41, pp. 6759-6771.
Heibel et al.; "Gas and liquid phase distribution and their effect on reactor performance in the monolith film flow reactor"; Chemical Engineering Science 56 (2001), pp. 5935-5944.
Heibel et al.; "Improving Flooding Performance for Countercurrent Monolith Reactors"; Ind. Eng. Chem. Res. 2004, 43, pp. 4848-4855.
Heibel et al.; "Influence of channel geometry on hydrodynamics and mass transfer in the monolith film flow reactor"; Catalysis Today 69 (2001), pp. 153-163.
Hessel et al.; "Gas-Liquid and Gas-Liquid-Solid Microstructured Reactors: Contacting Principles and Applications"; Ind. Eng. Chem. Res. 2005, 44, pp. 9750-9769.
Hessel et al.; "Gas/Liquid Microreactors for Direct Fluorination of Aromatic Compounds using Elemental Fluoride"; International Conference on Microreaction Technology, 2000, pp. 526-548.
Hessel et al.; "Gas/Liquid Microreactors: Hydrodynamics and Mass Transfer"; International Conference on Microreaction Technology, 2000, pp. 174-186.
Hessel et al.; "Microchemical Engineering: Components, Plant Concepts, User Acceptance—Part II"; Chem. eng. Technol. 26 (2003) 4.
Jahnisch et al.; "Direct fluorination of toluene using elemental fluorine in gas/liquid microreactors"; Journal of Fluorine Chemistry 105(2000), pp. 117-128.
Khinast et al.; "Reactive mass transfer at gas-liquid interfaces: impact of micro-scale fluid dynamics on yeild and selectivity of liquid-phase cyclohexane oxidation"; Chemical Engineering Science 58 (2003), pp. 3961-3971.
Kiwi-Minsker et al.; "Microstructured reactors for catalytic reactions"; Catalysis Today 110 (2005), pp. 2-14.
Koynov et al.; "Micromixing in Reactive, Deformable Bubble, and Droplet Swarms"; Chem. Eng. Technol. 1006, 29, No. 1, pp. 13-23.
Kreutzer et al.; "Multiphase monolith reactors: Chemical reaction engineering of segmented flow in microchannels"; Chemical Engineering Science 60 (2005), pp. 5895-5916.
Liu et al.; "Gas-Liquid Catalytic Hydrogenation Reaction in Small Catalyst Channel"; AIChE Journal, Aug. 2005, vol. 51, No. 8, pp. 2285-2297.
Losey et al.; "Design and Fabrication of Microfluidic Devices for Multiphase Mixing and Reaction"; Journal of Microelectromechanical Systems, vol. 11, No. 6, Dec. 2002, pp. 709-717.
Losey et al.; "A Micro Packed-Bed Reactor for Chemical Sythesis"; Department of Chemical Engineering, Massachusettes Institute of Technology, International Conference on Microreaction Technology, 2000, pp. 277-285.
Losey et al.; "Microfabricated Devices for Multiphase Catalytic Processes"; Department of Chemical Engineering, Massachusetts Institute of Technology, International Conference on Microreaction Technology, 2000, pp. 416-422.
Losey et al.; "Microfabricated Multiphase Packed-Bed Reactors: Characterization of Mass Transfer and Reactions"; Ind. Eng. Chem. Res. 2001, 40, pp. 2555-2562.
Lowe et al.; "Micromixing Technology"; International Conference on Microreaction Technology, 2000, pp. 31-48.
McGovern et al.; "Catalyst-Trap Microreactor for Hydrogentaiton of a Pharmaceutical Intermediate"; Stevens Institute of Technology.
Meille et al.; "Gas/Liquid Mass Transfer in Small Laboratory Batch Reactors: Comparison of Methods"; Ind. Eng. Chem. Res. 2004, 43, pp. 924-927.
Pestre et al.; "Effect of gas-liquid mass transfer on enantioselectivity in asymmetric hydrogenations"; Journal of Molecular Catalysis A: Chemical 252 (2006), pp. 85-89.
Roy et al.; "Design of monolithic catalysts for multiphase reactions"; Chemical Engineering Science 59(2004), pp. 957-966.
Roy et al.; "Monoliths as Multiphase Ractors: A Review"; AIChE Journal, Nov. 2004, vol. 50, No. 11, pp. 2918-2938.
Yeong et al.; "Catalyst preparation and deactivation issues for nitrobenzene hydrogenation in a microstructured falling film reactor"; Catalysis Today 81 (2003), pp. 641-651.
Yeong et al.; "Experimental studies of nitrobenzene hydrogenation in a microstructured falling film reactor"; Chemical Engineering Science 59(2004), pp. 3491-3493.
Utada et al.; "Monodisperse Double Emulsions Generated from a Microcapillary Device"; Science, vol. 308, Apr. 22, 2005, pp. 537-541.

* cited by examiner

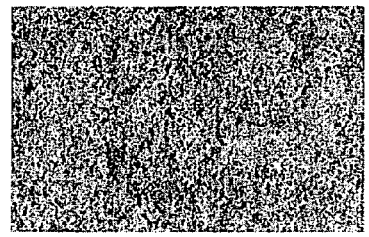
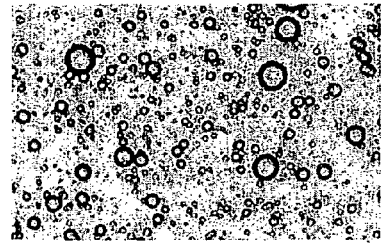
FIG. 22          FIG. 23
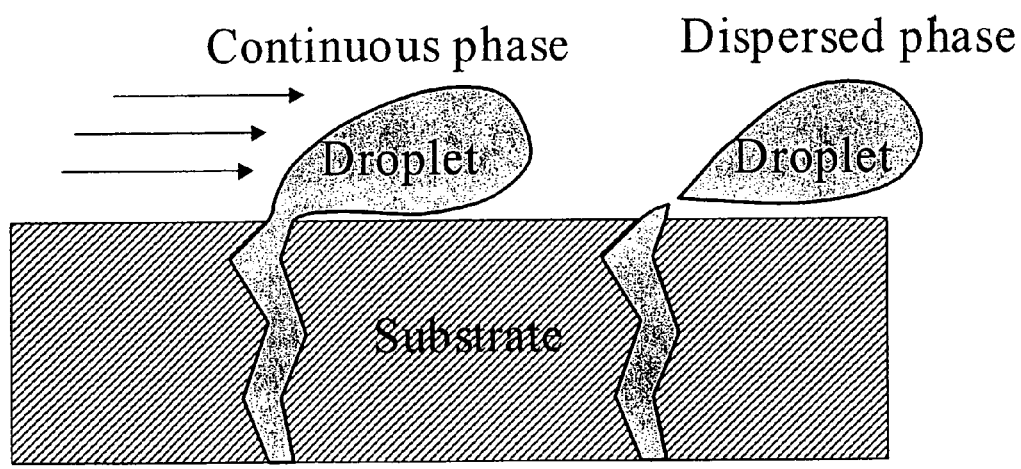
FIG. 24

PROCESS FOR FORMING AN EMULSION USING MICROCHANNEL PROCESS TECHNOLOGY

This application is a continuation-in-part of U.S. application Ser. No. 10/440,056, filed May 16, 2003. This application also claims priority to U.S. Provisional Application Ser. No. 60/548,152, filed Feb. 25, 2004. Each of these prior applications is incorporated herein by reference in its entirety.

TECHNICAL FIELD

This invention relates to a method for making an emulsion using microchannel process technology.

BACKGROUND

Emulsions may be formed when two or more immiscible liquids, usually water or a water-based solution and a hydrophobic organic liquid (e.g., an oil), are mixed so that one liquid forms droplets in the other liquid. Either of the liquids can be dispersed in the other liquid. When, for example, oil is dispersed in water, the emulsion may be referred to as an oil-in-water (o/w) emulsion. The reverse case is a water-in-oil (w/o) emulsion. More complex emulsions such as double emulsions may be formed when, for example, water droplets in a continuous oil phase themselves contain dispersed oil droplets. These oil-in-water-in-oil emulsions may be identified as o/w/o emulsions. In the same manner a w/o/w emulsion may be formed.

A problem with many emulsions is that if they are not stabilized, for example, by adding surfactants or emulsifiers, they tend to agglomerate, form a creaming layer, coalesce, and finally separate into two phases. If a surfactant or emulsifier (sometimes referred to as a surface-active agent) is added to one or both of the immiscible liquids, one of the liquids may form a continuous phase and the other liquid may remain in droplet form ("dispersed or discontinuous phase"), the droplets being dispersed in the continuous phase. The degree of stability of the emulsion may be increased when droplet size is decreased below certain values. For example, a typical o/w emulsion of a droplet size of 20 microns may be only temporally stable (hours) while that of one micron may be considered as "quasi-permanently" stable (weeks or longer). However, the energy consumption and the power requirement for the emulsification system and process may be significantly increased for smaller droplet sizes when using conventional processing techniques, especially for highly viscous emulsions with very small droplet sizes and large outputs. For example, the doubling of energy dissipation (energy consumption) may cause a reduction of average droplet size of only about 25% when using conventional processing techniques. Shear force may be applied to overcome the interfacial tension force and in turn to break larger droplets into smaller ones. However, as the droplet size decreases, the interfacial tension required to keep the droplet shape tends to increase. Energy consumption may take place in various forms, for example, it can be the energy needed by the stirrer to overcome shear force of the emulsion in a batch process, the energy for heating and cooling, and/or the power to overcome pressure drop in a continuous process such as in a homogenizer. Heating is often needed for emulsification when one of the phases does not flow or flows too slowly at room temperature. A heated emulsion typically has lower stability, however, due to lower viscosity of the continuous phase and in turn less drag. Drag may be necessary to stop or resist the motion of the droplets and in turn the coalescence into larger and often undesired droplets or aggregates of droplets as well as phase separation into layers. After emulsification, droplets tend to rise by buoyancy. As such, an immediate cooling down may be needed, which also consumes energy.

A problem with many of the processes that are currently available for making emulsions is that the range of compositions that are feasible for formulating product are constrained. For example, a problem with many of the emulsions that are currently available relates to the presence of surfactants or emulsifiers in their formulations. These surfactants or emulsifiers may be required to stabilize the emulsions, but may be undesirable for many applications. For example, heating without bubbling or boiling is often desired in emulsification processes, however in some instances the onset temperature of nucleate boiling or air bubble formation from dissolved air in the continuous phase may lower when surfactants or emulsifiers are present. Boiling may cause unwanted property changes. Air bubbles may cause creaming and other undesired features.

Emulsions that have low surfactant or emulsifier concentrations or are free of such surfactants or emulsifiers are often desirable for skin care products in the cosmetic industry. A disadvantage with some surfactants or emulsifiers is their tendency to interact with preservatives, such as the esters of p-hydroxybenzoic acid, used in skin care products. Skin irritation is another problem often associated with the use of surfactants or emulsifiers. Many adverse skin reactions experienced by consumers from the use of cosmetics may be related to the presence of the surfactants or emulsifiers. Another example relates to the problem with using surfactants or emulsifiers wherein water proofing is desired. For example, in water-based skin care products such as sunscreen, the active ingredient may not be waterproof due to the presence of water-soluble surfactants or emulsifiers.

A problem relating to the use of many pharmaceutical compounds relates to the fact that they are insoluble or poorly soluble in water and there are limitations as to the surfactants or emulsifiers that can be used. This has resulted in the discovery of drugs that are not clinically acceptable due to problems relating to transporting the drugs into the body. Emulsion formulation problems may be problematic with drugs for intravenous injection and the administration of chemotherapeutic or anti-cancer agents.

SUMMARY

The present invention, at least in one embodiment, may provide a solution to one or more of the foregoing problems. In one embodiment, it may be possible to make an emulsion using a relatively low level of energy as compared to the prior art. The emulsion made in accordance with the inventive process, at least in one embodiment, may have a dispersed phase with a relatively small droplet size and a relatively uniform droplet size distribution. The emulsion made in accordance with the inventive process, in one embodiment, may exhibit a high degree of stability. In one embodiment, the emulsion made by the inventive process may have a low surfactant or emulsifier concentration or be free of such surfactants or emulsifiers. The emulsions made in accordance with the inventive process, in one embodiment, may be useful, for example, as a skin care product, pharmaceutical composition, etc.

The invention relates to a process for making an emulsion, comprising: flowing a first liquid through a process microchannel, the process microchannel having a wall with an apertured section; flowing a second liquid through the apertured section into the process microchannel in contact with the first liquid to form the emulsion, the second liquid being immiscible with the first liquid, the first liquid forming a continuous phase, the second liquid forming a discontinuous phase dispersed in the continuous phase. In one embodiment, the second liquid flows from a liquid channel through the apertured section.

In one embodiment, heat is exchanged between the process microchannel and a heat exchanger, the liquid channel and a heat exchanger, or both the process microchannel and the liquid channel and a heat exchanger. The heat exchanger may be used for cooling, heating or both cooling and heating. The heat exchanger may comprise a heat exchange channel, a heating element and/or a cooling element adjacent to the process microchannel, the liquid channel, or both the process microchannel and the liquid channel. In one embodiment, the heat exchanger may not be in contact with or adjacent to the process microchannel or liquid channel but rather can be remote from either or both the process microchannel and liquid channel.

In one embodiment, the first liquid and the second liquid contact each other in a mixing zone in the process microchannel.

In one embodiment, heat is exchanged between a heat exchanger and at least part of the process microchannel in the mixing zone.

In one embodiment, heat is exchanged between a heat exchanger and at least part of the process microchannel upstream of the mixing zone.

In one embodiment, heat is exchanged between a heat exchanger and at least part of the process microchannel downstream of the mixing zone.

In one embodiment, the emulsion is quenched in the process microchannel downstream of the mixing zone.

In one embodiment, the process microchannel has a restricted cross section in the mixing zone.

In one embodiment, the process microchannel has walls that are spaced apart and apertured sections in each of the spaced apart walls, the second liquid flowing through each of apertured sections into the process microchannel. In one embodiment, the apertured sections in each of the spaced apart walls comprise a plurality of apertures, the apertures in the apertured section of one of the walls being aligned directly opposite the apertures in the apertured section of the other wall. In one embodiment, the apertured sections in each of the spaced apart walls comprise a plurality of apertures, at least some of the apertures in the apertured section of one of the walls being offset from being aligned directly with the apertures in the apertured section of the other wall.

In one embodiment, the process microchannel is in an emulsion forming unit comprising a first process microchannel, a second process microchannel, and a liquid channel positioned between the first process microchannel and the second process microchannel, each process microchannel having a wall with an apertured section, the first liquid flowing through the first process microchannel and the second process microchannel, the second liquid flowing from the liquid channel through the apertured section in the first process microchannel in contact with the first liquid and through the apertured section in the second process microchannel in contact with the first liquid.

In one embodiment, the process microchannel is circular and is positioned between a circular disk and an apertured section, the circular disk rotating about its axis, the first liquid flowing through a center opening in the apertured section into the process microchannel onto the rotating disk, the second liquid flowing through the apertured section into the process microchannel where it contacts and mixes with the first liquid to form the emulsion, the emulsion flowing radially outwardly on the rotating disk.

In one embodiment, the second liquid flows in a liquid channel, the liquid channel having another wall with another apertured section, the process further comprising: flowing a third liquid through the another apertured section in contact with the second liquid to form a liquid mixture; and flowing the liquid mixture through the apertured section into the process microchannel in contact with the first liquid.

In one embodiment, the process microchannel is formed from parallel sheets, plates or a combination of such sheets or plates.

In one embodiment, the process is conducted in a microchannel mixer, the microchannel mixer comprising a plurality of the process microchannels, the process microchannels having walls with apertured sections and adjacent liquid channels, the second liquid flowing from the liquid channels through the apertured sections into the process microchannels in contact with the first liquid, the process microchannels and liquid channels being formed from parallel spaced sheets or plates, the process microchannels and liquid channels being adjacent to each other and aligned in interleaved side-by-side vertically oriented planes or interleaved horizontally oriented planes stacked one above another.

In one embodiment, the process microchannel comprises two or more apertured sections and separate second liquids flow through each of the apertured sections. In one embodiment, the separate second liquids flowing through each of the apertured sections have different compositions. In one embodiment the separate second liquids flowing through each of the apertured sections have different properties.

In one embodiment, the process is conducted in a microchannel mixer, the microchannel mixer comprising at least two of the process microchannels, and in one embodiment at least about 10 of the process microchannels, and in one embodiment at least about 100 of the process microchannels, and in one embodiment at least about 1000 of the process microchannels.

In one embodiment, the process is conducted in a microchannel mixer, the microchannel mixer comprising a plurality of the process microchannels connected to at least one first liquid manifold, the first liquid flowing through the at least one first liquid manifold to the process microchannels. In one embodiment, liquid channels are adjacent to the process microchannels, and the microchannel mixer further comprises at least one second liquid manifold connected to the liquid channels, the second liquid flowing through the at least one second liquid manifold to the liquid channels. In one embodiment, heat exchange channels are adjacent to the process microchannels and/or liquid channels, the microchannel mixer further comprising at least one heat exchange manifold connected to the heat exchange channels, and a heat exchange fluid flows through the at least one heat exchange manifold to the heat exchange channels.

In one embodiment, the second liquid flows from a liquid channel through the apertured section into the process microchannel, the process microchannel and the liquid channel comprising circular tubes aligned concentrically.

In one embodiment, the process is conducted in a microchannel mixer, the microchannel mixer comprising a plurality of the process microchannels wherein separate emulsions are formed in each of the process microchannels, the emulsions formed in at least two of the process microchannels being different from each other. The emulsions can have different compositions and/or different properties. This mixer may be referred to as a combinatorial synthesis and screening device. An advantage of this embodiment of the invention is that it provides for the forming and evaluating of multiple product emulsions at the same time using the same apparatus. This can be advantageous when it is desired to screen multiple formulations as potential new products.

In one embodiment, the process for making an emulsion in a microchannel mixer, the microchannel mixer comprising a plurality of emulsion forming units aligned side-by-side or stacked one above another, each emulsion forming unit comprising a process microchannel and an adjacent liquid channel, the process microchannel and adjacent liquid channel having a common wall with an apertured section in the common wall, the apertured section being suitable for flowing a liquid from the liquid channel through the apertured section into the process microchannel, each process microchannel and liquid channel being formed from parallel spaced sheets, plates, or a combination of such sheets and plates, the process comprising: flowing a first liquid in the process microchannel; flowing a second liquid from the liquid channel through the apertured section into the process microchannel; and mixing the first liquid and the second liquid in the process microchannel to form the emulsion.

In one embodiment, the inventive process may be operated with a relatively low pressure drop for the flow of the first liquid through the process microchannel. In one embodiment, the inventive process may be operated with a relatively low pressure drop for the flow of the second liquid through the apertured section into the process microchannel.

BRIEF DESCRIPTION OF THE DRAWINGS

In the annexed drawings, like parts and features have like references.

FIG. 22 is a microscopic image of an emulsion made by the inventive process.

FIG. 23 is a microscopic image of an emulsion made by a batch emulsification process.

FIG. 24 is a schematic illustration showing the formation of a droplet during the operation of the inventive process.

DETAILED DESCRIPTION

The term "microchannel" refers to a channel having at least one internal dimension (for example, width, height, diameter, etc.) of up to about 50 millimeters (mm), and in one embodiment up to about 10 mm, and in one embodiment up to about 5 mm, and in one embodiment up to about 2 mm, and in one embodiment up to about 1 mm. In one embodiment, this internal dimension may be in the range of about 0.05 to about 50 mm, and in one embodiment about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. This internal dimension may be perpendicular to the direction of flow through the microchannel.

The term "adjacent" when referring to the position of one channel relative to the position of another channel means directly adjacent such that a wall separates the two channels.

This wall may vary in thickness. However, "adjacent" channels are not separated by an intervening channel that would interfere with heat transfer between the channels.

The term "immiscible" refers to one liquid not being soluble in another liquid or only being soluble to the extent of up to about 1 milliliter per liter at 25° C.

The term "water insoluble" refers to a material that is insoluble in water at 25° C., or soluble in water at 25° C. up to a concentration of about 0.1 gram per liter.

The terms "upstream" and "downstream" refer to positions within the channels, including microchannels, used in the inventive process that are relative to the direction of flow of liquid through the channels. For example, a position within a channel not yet reached by a portion of a liquid flowing through that channel toward that position would be downstream of that portion of the liquid. A position within a channel already passed by a portion of the liquid flowing through that channel away from that position would be upstream of that portion of the liquid. The terms "upstream" and "downstream" do not necessarily refer to a vertical position since the channels used in the inventive process may be oriented horizontally, vertically, or at an inclined angle.

Figure 1:
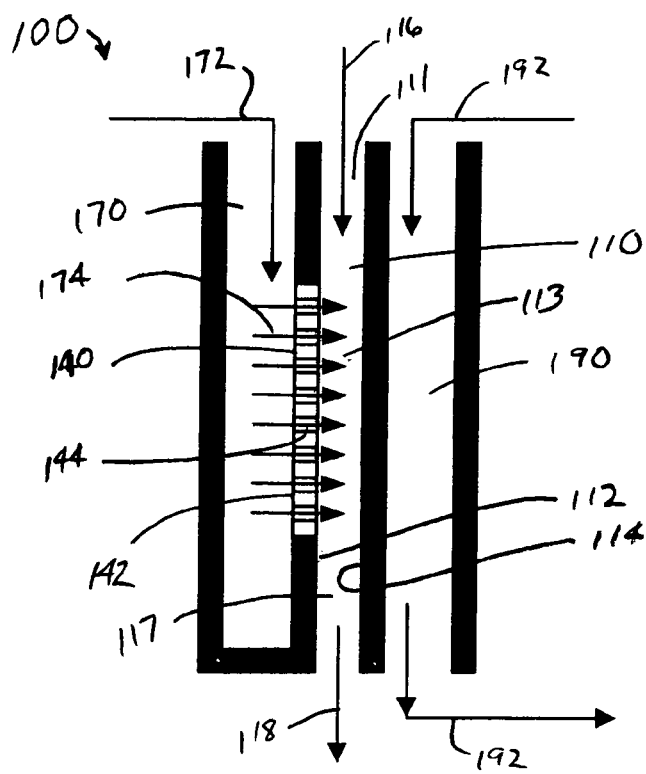
FIG. 1 is a flow sheet illustrating an emulsion forming unit for use with the inventive process wherein a first liquid flows through a process microchannel and is mixed with a second liquid that flows into the process microchannel from an adjacent channel through an apertured section in the process microchannel.

The inventive process will be initially described with reference to FIG. 1. Referring to FIG. 1, the inventive process may be conducted using emulsion forming unit 100 which comprises process microchannel 110 which has opposite sidewalls 112 and 114, and an apertured section 140 in sidewall 112. The apertured section 140 may be referred to as a porous section or porous substrate. The apertured section 140 may comprise a sheet or plate 142 having an array of apertures 144 extending through it. Adjacent to the sidewall 112 is liquid channel 170 which opens to process microchannel 110 through apertured section 140. The process microchannel 110 has non-apertured or non-porous regions 111 and 117, and mixing zone 113. The non-apertured region 111 extends from the entrance to the process microchannel to the entrance to the mixing zone 113. The non-apertured region 111 is upstream of the mixing zone 113. The mixing zone 113 is adjacent to the apertured section 140. The non-apertured region 117 extends from the end of mixing zone 113 to the exit of the process microchannel 110. The non-apertured region 117 is downstream of the mixing zone 113. Adjacent to sidewall 114 is heat exchange channel 190. In operation, a first liquid flows into process microchannel 110, as indicated by directional arrow 116, and through the non-apertured region 111 into the mixing zone 113. A second liquid flows into liquid channel 170, as indicated by directional arrow 172, and then flows through apertured section 140, as indicated by directional arrows 174, into the mixing zone 113. In mixing zone 113, the second liquid contacts and mixes with the first liquid to form an emulsion. The second liquid may form a discontinuous phase within the first liquid. The first liquid may form a continuous phase. The emulsion flows from the mixing zone 113 through the non-apertured region 117 and out of the process microchannel 110, as indicated by directional arrow 118. The emulsion may be a water-in-oil emulsion or an oil-in-water emulsion. Heating or cooling may be optional. When heating or cooling is desired, heat exchange fluid flows through the heat exchange channel 190, as indicated by directional arrows 192, and heats or cools the liquids in the process microchannel 110 and liquid channel 170. The degree of heating or cooling may vary over the length of the process microchannel 110 and liquid channel 170. The heating or cooling may be negligible or non-existent in some sections of the process microchannel and liquid channel, and moderate or relatively high in other sections. Alternatively, the heating or cooling can be effected using other than a heat exchange fluid. For example, heating can be effected using an electric heating element. The electric heating element can be used to form one or more walls of the process microchannel 110 and/or liquid channel 170. The electric heating can be built into one or more walls of the process microchannel 110 and/or liquid channel 170. Cooling can be effected using a non-fluid cooling element. Multiple heating or cooling zones may be employed along the length of the process microchannel 110. Similarly, multiple heating fluids at different temperatures may be employed along the length of the process microchannel 110 and/or liquid channel 170.

Figure 2:
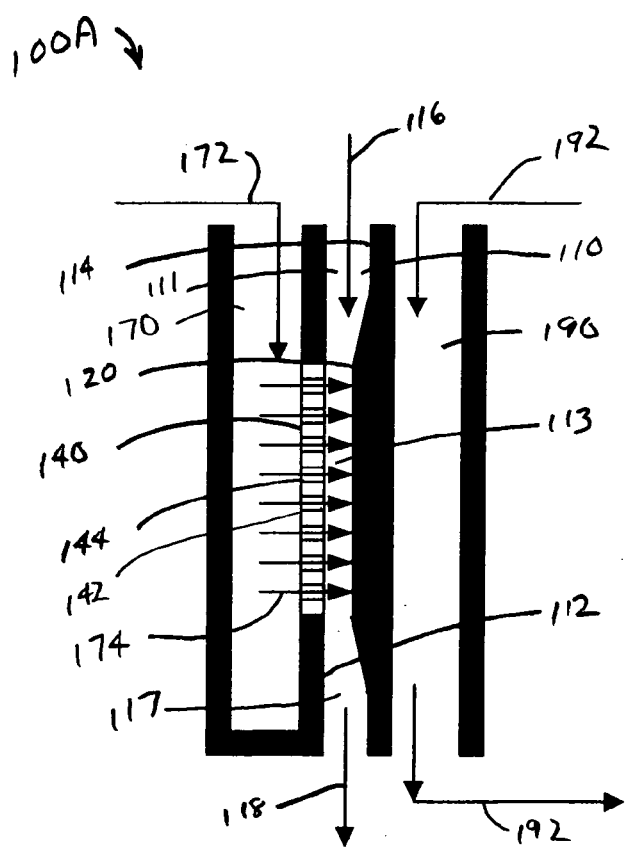
FIGS. 2-6 are flow sheets illustrating embodiments of emulsion forming units for use with the inventive process.

The emulsion forming unit 100A illustrated in FIG. 2 is identical to the emulsion forming unit 100 illustrated in FIG. 1 with the exception that the sidewall 114 of process microchannel 110 includes tapered section 120 which is aligned opposite apertured section 140. Tapered section 120 reduces the width or height of the process microchannel 110 in the mixing zone 113, and thus provides a restricted cross section for the process microchannel 110 in the mixing zone 113. The width or height may be in the range from about 0.001 to about 5 mm, and in one embodiment from about 0.01 to about 2 mm. The presence of tapered section 120 provides for an increase in the velocity of the liquid flowing through the mixing zone 113. The increased velocity of the liquid flowing through the mixing zone 113 results in an increased shear force acting on the second fluid flowing through apertures 144 into the mixing zone 113. This facilitates the flow of the second liquid through the apertures 144 into the mixing zone 113. The velocity of liquid flowing through the restricted cross section of the process microchannel 110 adjacent to the tapered section 120 may be in the range from about 0.005 to about 50 m/s, and in one embodiment from about 0.01 to about 50 m/s.

Figure 3:
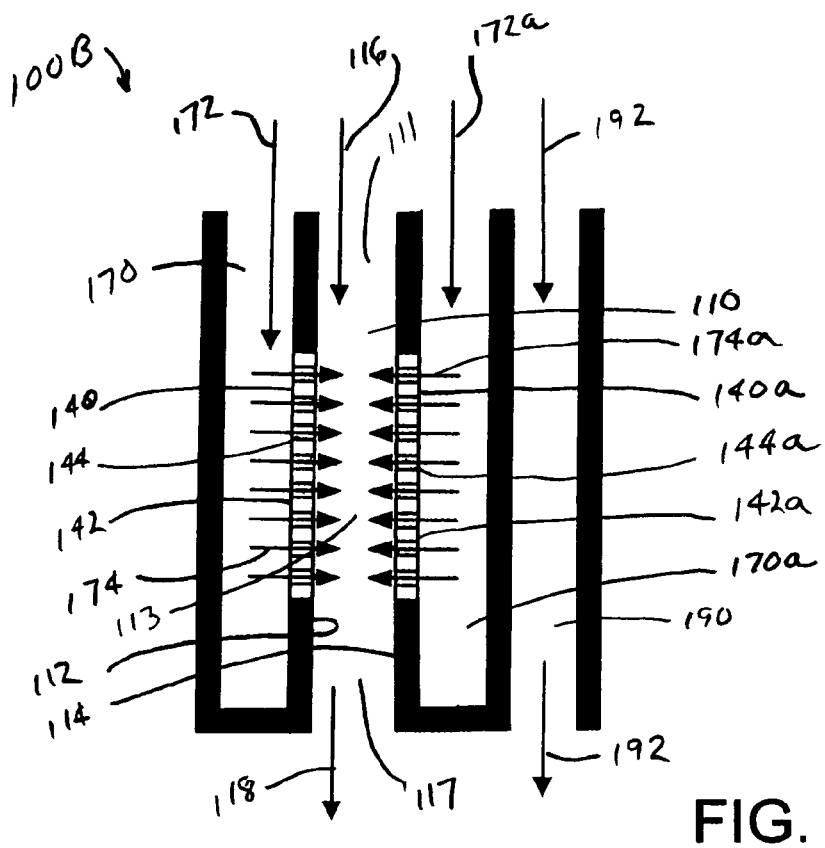

The emulsion forming unit 100B illustrated in FIG. 3 is similar to the emulsion forming unit 100 illustrated in FIG. 1 with the exception that the emulsion forming unit 100B also includes liquid channel 170a and apertured section 140a. Liquid channel 170a is positioned between process microchannel 110 and heat exchange channel 190. Apertured section 140a is formed in sidewall 114. Liquid channel 170a opens to process microchannel 110 through apertured section 140a. The apertured section 140a may comprise a sheet or plate 142a having an array of apertures 144a extending through it. The process microchannel 110 has non-apertured or non-porous region 111 and 117, and a mixing zone 113. The non-apertured region 111 extends from the entrance to the process microchannel to the entrance to the mixing zone 113 and is upstream from the mixing zone 113. The mixing zone 113 is adjacent to the apertured sections 140 and 140a. The non-apertured region 117 extends from the end of mixing zone 113 to the exit of the process microchannel 110. The non-apertured region 117 is downstream of the mixing zone 113. In operation, a first liquid flows into process microchannel 110, as indicated by directional arrow 116, and through the non-apertured region 111 into the mixing zone 113. A second liquid flows into liquid channels 170 and 170a as indicated by directional arrows 172 and 172a, respectively. The second liquid flows through apertured sections 140 and 140a, as indicated by directional arrows 174 and 174a, respectively, into the mixing zone 113. In mixing zone 113, the second liquid contacts and mixes with the first liquid to form an emulsion. The second liquid may form a discontinuous phase within the first liquid. The first liquid may form a continuous phase.

The emulsion flows through the non-apertured region 117 and out of the process microchannel 110, as indicated by directional arrow 118. The emulsion may be a water-in-oil emulsion or an oil-in-water emulsion. Heating or cooling may be optional. When heating or cooling is desired, heat exchange fluid flows through heat exchange channel 190, as indicated by directional arrows 192, and heats or cools the liquids in the process microchannel 110 and the liquid channels 170 and 170a. The degree of heating or cooling may vary over the length of the process microchannel and the liquid channels. The heating or cooling may be negligible or non-existent in some sections of the process microchannel and liquid channels, and moderate or relatively high in other sections.

Figure 4:
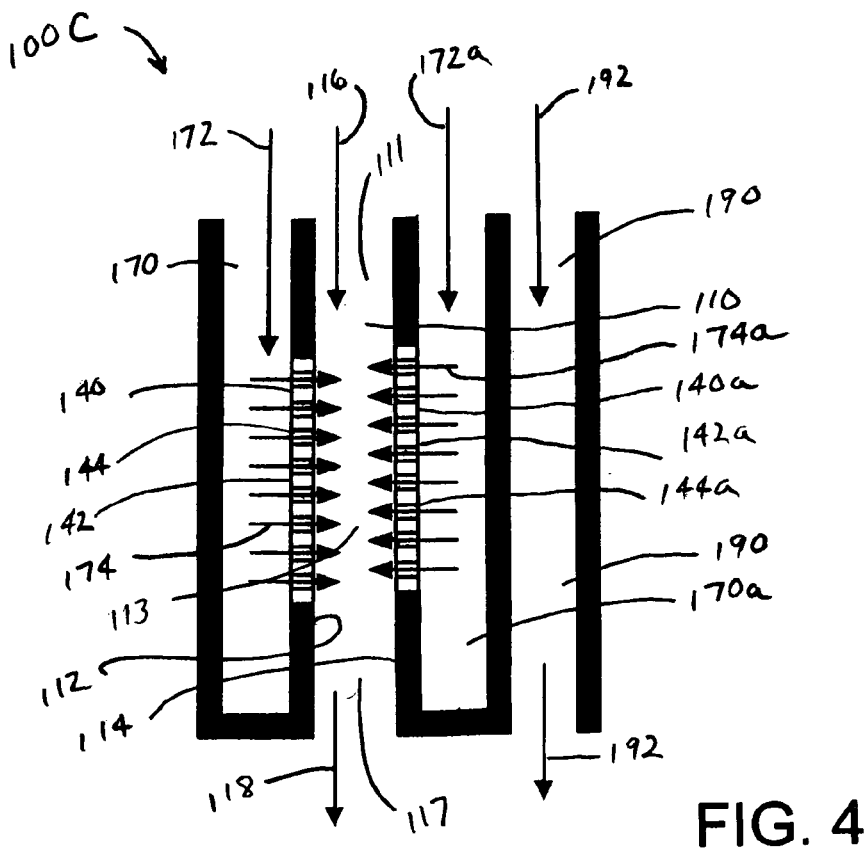

The emulsion forming unit 100C illustrated in FIG. 4 is identical to the emulsion forming unit 100B illustrated in FIG. 3 with the exception that the apertures 144 and 144a illustrated in FIG. 3 are aligned directly opposite each other, while the apertures 144 and 144a illustrated in FIG. 4 are offset from such direct alignment. In FIG. 3 streams of the second liquid flowing through the apertures 144 and 144a impinge directly on one another and thereby enhance the diffusion of the second liquid into the first liquid. On the other hand, in FIG. 4 the streams of the second liquid flowing through the apertures 144 and 144a are offset from one another and thereby enhance diffusion by providing a swirling effect within the mixing zone 113.

Figure 5:
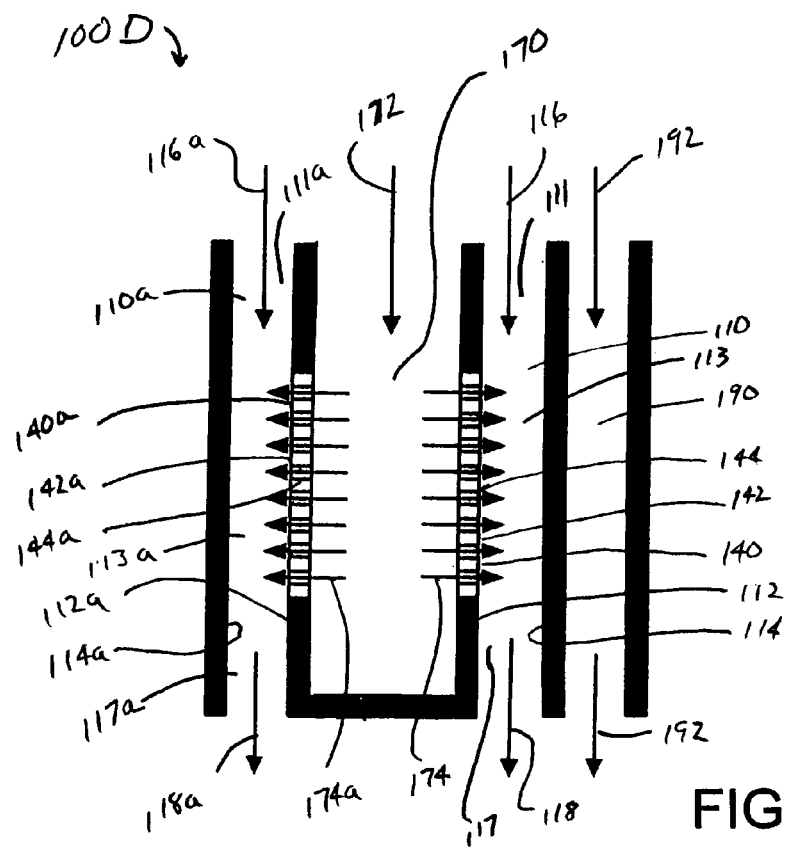

The emulsion forming unit 100D illustrated in FIG. 5 includes process microchannels 110 and 110a, apertured sections 140 and 140a, liquid channel 170, and heat exchange channel 190. Apertured section 140 is formed in side wall 112, and apertured section 140a is formed in side wall 114. The apertured sections 140 and 140a may be referred to as porous sections or porous substrates. Liquid channel 170 opens to process microchannels 110 and 110a through apertured sections 140 and 140a, respectively. The apertured section 140 may comprise a sheet or plate 142 having an array of apertures 144 extending through it. Similarly, the apertured section 140a may comprise a sheet or plate 142a having an array of apertures 144a extending through it. The process microchannels 110 and 110a have non-apertured or non-porous regions 111 and 117, and 111a and 117a, and mixing zones 113 and 113a, respectively. The non-apertured regions 111 and 111a extend from the entrance to the process microchannels 110 and 110a to the entrances to the mixing zones 113 and 113a, respectively. The non-apertured regions 111 and 111a are upstream from the mixing zones 113 and 113a, respectively. The mixing zones 113 and 113a are adjacent to the apertured sections 140 and 140a, respectively. The non-apertured regions 117 and 117a extend from the end of the mixing zones 113 and 113a to the exit of the process microchannels 110 and 110a, respectively. The non-apertured regions 117 and 117a are downstream from the mixing zones 113 and 113a, respectively. Adjacent to the process microchannel 110 is heat exchange channel 190. In operation, a first liquid flows into the process microchannels 110 and 110a, as indicated by directional arrows 116 and 116a, respectively, and through the non-apertured regions 111 and 111a into the mixing zones 113 and 113a. A second liquid flows into liquid channel 170, as indicated by directional arrow 172, and then flows through apertured sections 140 and 140a, as indicated by directional arrows 174 and 174a, into mixing zones 113 and 113a, respectively. In the mixing zones 113 and 113a, the second liquid contacts and mixes with the first liquid to form an emulsion. The second liquid may form a discontinuous phase within the first liquid. The first liquid may form a continuous phase. The emulsion flows through non-apertured section 117 and 117a and out of the process microchannels 110 and 110a, as indicated by directional arrows 118 and 118a, respectively. The emulsion may be a water-in-oil emulsion or an oil-in-water emulsion. Heating or cooling may be optional. When heating or cooling is desired, heat exchange fluid flows through the heat exchange channel 190, as indicated by directional arrows 192, and heats or cools the liquid in the channels 110, 110a and 170. The degree of heating or cooling may vary over the length of the channels. The heating or cooling may be negligible or non-existent in some sections of the process microchannels 110 and 110a and liquid channel 170, and moderate or relatively high in other sections.

Figure 6:
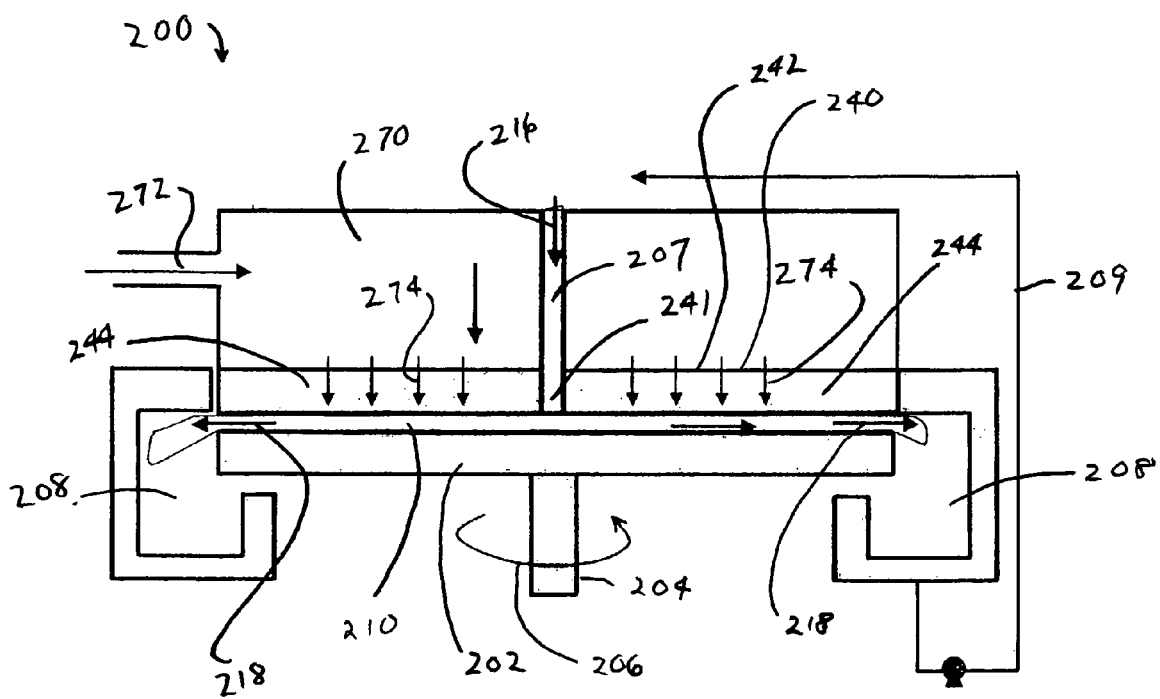

In one embodiment, the emulsion forming unit may include a rotating disk and the process microchannel may be circular in form. This embodiment is illustrated in FIG. 6. Referring to FIG. 6, emulsion forming unit 200 includes circular disk 202, process microchannel 210, apertured section 240 and liquid channel or container 270. Process microchannel 210 is circular in form and is positioned between circular disk 202 and apertured section 240. The apertured section 240 may contain a plurality of apertures 244 in a sheet or plate 242 for permitting liquid to flow from the liquid channel or container 270 to the process microchannel 210. Circular disk 202 rotates about shaft 204 as indicated by circular arrow 206. Shaft 204 may be driven by or connected to a motor or a rotation transformation mechanism, such as a gear. The first liquid flows through inlet 207, as indicated by directional arrow 216, to and through opening 241 in apertured section 240 into microchannel 210. The second liquid flows through inlet 272 into liquid channel 270. In liquid channel 270 the second liquid is pressurized and forced through apertured section 240 into process microchannel 210, as indicated by directional arrows 274. The first liquid and second liquid are mixed with each other in process microchannel 210 to form an emulsion. The second liquid may form a discontinuous phase within the first liquid. The first liquid may form a continuous phase. The emulsion formed in the process microchannel 210 flows outwardly from the center of the process microchannel as indicated by directional arrows 218, into emulsion collector 208. The flow of the emulsion outwardly in the direction indicated by arrows 218 is effected by a pressure differential within the process microchannel 210 and/or the centrifugal force resulting from the rotation of the disk 202. Optionally, the emulsion may be recirculated back from the emulsion collector to the first liquid entrance 207, as indicated by line 209. The gap between the circular disk 202 and the apertured section 240, which defines the process microchannel 210, may be up to about 10 mm, and in one embodiment from about 0.05 to about 10 mm, and in one embodiment from about 0.05 to about 5 mm, and in one embodiment from about 0.05 to about 2 mm, and in one embodiment from about 0.05 to about 1.5 mm, and in one embodiment from about 0.05 to about 1 mm. The diameter of the circular disk 202 may be of any dimension, for example, from about 0.5 to about 500 cm, and in one embodiment about 1 to about 250 cm, and in one embodiment from about 2 to about 100 cm, and in one embodiment from about 2 to about 50 cm. The circular disk 202 may rotate at any rate, for example, about 0.2 to about 50,000 revolutions per minute (rpm), and in one embodiment from about 1 to about 5000 rpm. Optionally, heat exchange channels may be employed in positions adjacent to the liquid channel or container 270 and/or rotating disk 202 to heat or cool the liquids. The height or thickness of liquid channel or container 270 may be of any dimension, for example, about 0.01 to about 50 mm, and in one embodiment about 0.1 to about 10 mm. The flow rate of liquid through the process microchannel 210 may range from about 0.01 to about 1000 liters per minute (lpm), and in one embodiment 0.1 to about 200 lpm. The velocity of liquid flowing through the process microchannel 210 may range from about 0.001 to about 50 meters per second (m/s), and in one embodiment about 0.01 to about 10 m/s. The Reynolds Number for the liquid flowing through the process microchannel 210 may range from about 5 to about 50,000, and in one embodiment about 10 to about 5000. The temperature of the first liquid entering the process microchannel 210 may range from about 0° C. to about 200° C., and in one embodiment about 20° C. to about 100° C. The pressure within the process microchannel 210 may be in the range of about 0.01 to about 1000 atmospheres, and in one embodiment about 1 to about 10 atmospheres. The flow rate of the second liquid flowing through the liquid channel or container 270 may range from about 0.001 to about 200 ml/s, and in one embodiment about 0.01 to about 100 ml/s. The temperature of the second liquid in the liquid channel 270 may range from about −20° C. to about 250° C., and in one embodiment about 20° C. to about 100° C. The pressure within the liquid channel or container 270 may be at about 0.1 to about 1000 atmospheres, and in one embodiment about 0.2 to about 100 atmospheres. The pressure drop for the second liquid flowing through the apertured section 240 may range from about 0.01 to about 500 atmospheres, and in one embodiment about 0.1 to about 100 atmospheres.

Figure 33:
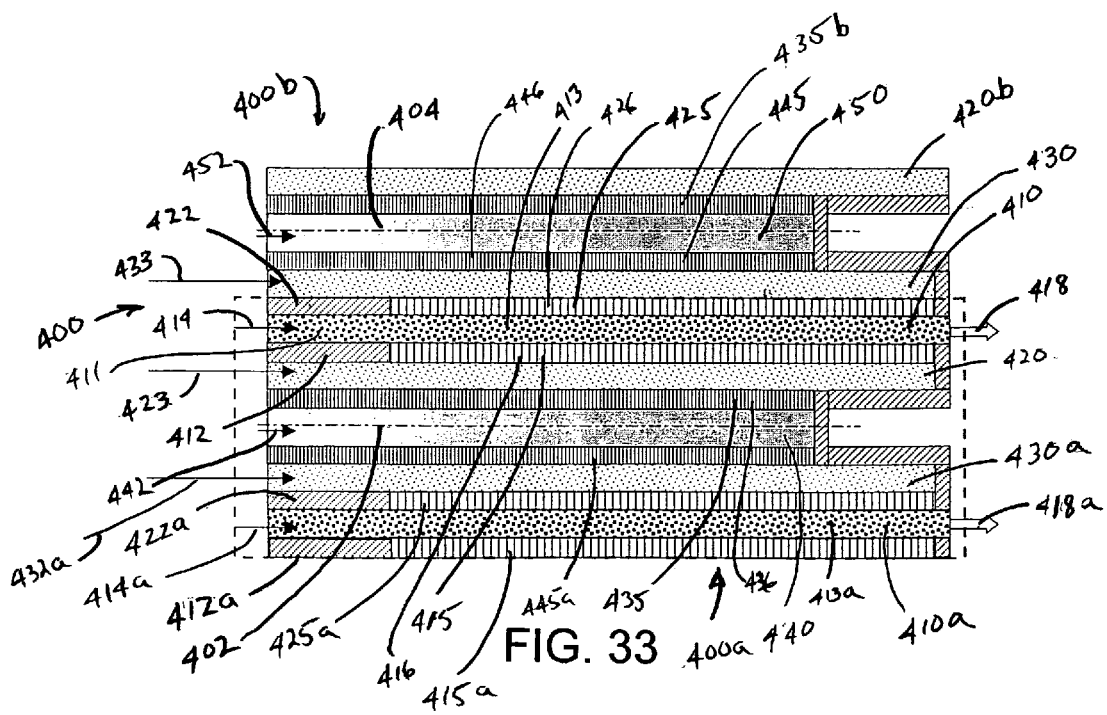
FIG. 33 is a flow sheet illustrating an embodiment of an emulsion forming unit for use with the inventive process, this emulsion forming unit being useful for making double emulsions.

In one embodiment, the inventive process is suitable for making double emulsions. These double emulsions may be made using the emulsion forming unit 400 illustrated in FIG. 33. In FIG. 33, the emulsion forming unit 400 is positioned between center lines 402 and 404. Emulsion forming unit 400 includes process microchannel 410, and liquid channels 420, 430, 440 and 450. Liquid channels 420 and 430 are adjacent to process microchannel 410. Liquid channel 440 is adjacent to liquid channel 420, and liquid channel 450 is adjacent to liquid channel 430. Common wall 412, which includes coarse apertured section 415, separates process microchannel 410 and liquid channel 420. Common wall 422, which includes coarse apertured section 425, separates process microchannel 410 and liquid channel 430. Apertured sections 415 and 425 contain apertures 416 and 426, respectively. Fine apertured section 435, which contains apertures 436, is positioned between and separates liquid channel 440 and liquid channel 420. Fine apertured section 445, which contains apertures 446, is positioned between and separates liquid channel 450 and liquid channel 430. The apertures 416 and 426 in the coarse apertured sections 415 and 425 are larger than the apertures 436 and 446 in the fine apertured sections 435 and 445. The process microchannel 410 has a non-apertured or non-porous region 411 and a mixing zone 413. The non-apertured region 411 extends from the entrance to the process to the entrance to the mixing zone 413. The mixing zone 413 is adjacent to the apertured sections 415 and 425. Optionally, heat exchange channels may be inserted in the positions shown by centerlines 402 and/or 404 to provide desired heating or cooling for the liquids.

Part of an adjacent emulsion forming unit 400a, which is also illustrated in FIG. 33, is positioned below center line 402. The emulsion forming unit 400a includes process microchannel 410a, coarse apertured sections 415a and 425a, liquid channel 430a, and fine apertured section 445a. These are the same as the process microchannel 410, coarse apertured sections 415 and 425, liquid channel 430, and fine apertured section 445 discussed above. Also, part of another adjacent emulsion forming unit 400b is positioned above the center line 404 in FIG. 33. The emulsion forming 400b includes fine apertured section 435b and liquid channel 420b. These are the same as the fine apertured section 435 and liquid channel 420 discussed above. The inclusion of parts of emulsion forming units 400a and 400b in FIG. 33 illustrates the repeating character of the emulsion forming unit 400 when it is employed in a microchannel mixer pursuant to the inventive process.

In operation, referring to FIG. 33, a first liquid enters process microchannel 410, as indicated by arrow 414, and flows through the non-apertured region 411 into the mixing zone 413. A second liquid enters liquid channels 420 and 430, as indicated by arrows 423 and 433, respectively. A third liquid enters liquid channels 440 and 450, as indicated by arrows 442 and 452, respectively. The third liquid flows from liquid channel 440 through apertured section 435 into liquid channel 420 where it mixes with the second liquid and forms another emulsion. Also, the third liquid flows from liquid channel 450 through apertured section 445 into liquid channel 430 where it mixes with the second liquid and forms another emulsion. The third liquid forms a discontinuous phase and the second liquid forms a continuous phase in the another emulsions formed in the liquid channels 420 and 430. The another emulsions formed in the liquid channels 420 and 430 flow through the apertured sections 415 and 425, respectively, into mixing zone 413 where they mix with the first liquid. In the mixing zone 413, the another emulsion is dispersed as a discontinuous phase in the first liquid, the first liquid being in the form of a continuous phase. The emulsion that is formed in the mixing zone 413 is a double emulsion. In the double emulsion at least part of the third liquid may be encapsulated within droplets of the second liquid. The encapsulated droplets are dispersed as a discontinuous phase in the first liquid which is in the form of a continuous phase. The double emulsion exits process microchannel 410, as indicated by arrow 418.

Figure 34:
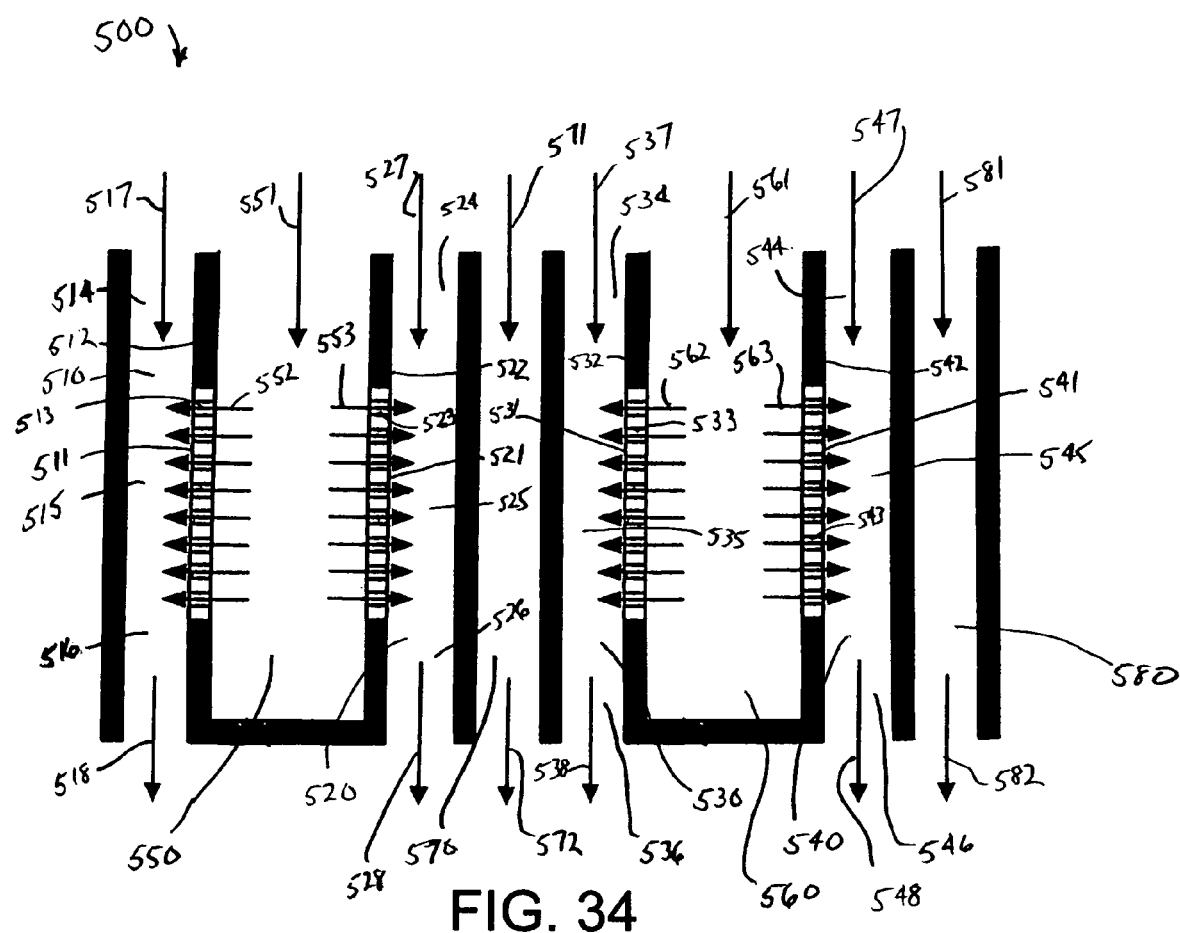
FIG. 34 is a flow sheet illustrating an embodiment of an emulsion forming unit for use with the inventive process wherein multiple emulsion formulations and/or processing conditions may be used to generate separate and distinct emulsions within one device.

In one embodiment, multiple emulsion formulations and/or sets of processing conditions may be used to generate distinct emulsions within a single microchannel mixer. For example, a single microchannel mixer may employ two or more process microchannels and associated liquid channels and heat exchange channels to make two, three, four, five, six, seven, eight, nine, ten, tens, hundreds, thousands, tens of thousands, hundreds of thousands, etc. of distinct emulsions within a single microchannel mixer. This type of mixer can be referred to as a combinatorial-synthesis device. This is illustrated in FIG. 34 wherein emulsion forming unit 500 is illustrated. Emulsion forming unit 500 employs four process microchannels and as a result may be capable of generating up to four distinct emulsions. The emulsion forming unit 500 can be repeated any desired number of times, for example, two, three, four, five, six, seven, eight, nine, ten, tens, hundreds, thousands, tens of thousands, etc., to provide for the possibility of the multiple distinct emulsions indicated above. Emulsion forming unit 500 includes process microchannels 510, 520, 530 and 540, liquid channels 550 and 560, and heat exchange channels 570 and 580. Apertured section 511 is formed in sidewall 512. Apertured section 521 is formed in sidewall 522. Apertured section 531 is formed in sidewall 532. Apertured section 541 is formed in sidewall 542. Apertures 513, 523, 533 and 543 are positioned in and extend through apertured sections 511, 521, 531 and 541, respectively. The process microchannels 510, 520, 530 and 540 include non-apertured section 514, 524, 534 and 544 positioned upstream from mixing sections 515, 525, 535 and 545, respectively. Mixing sections 515, 525, 535 and 545 are positioned adjacent to apertured sections 511, 521, 531 and 541, respectively. The process microchannels 510, 520, 530 and 540 also include non-apertured sections 516, 526, 536 and 546 which are positioned downstream of the mixing zones 515, 525, 535 and 545, respectively. In operation, first liquids flow into process microchannels 510, 520, 530 and 540 as indicated by arrows 517, 527, 537 and 547, respectively. The first liquids entering process microchannels 510, 520, 530 and 540 may have compositions that are the same as one another or the compositions may be different from one another. The first liquids flow through the non-apertured sections 514, 524, 534 and 544 into the mixing zones 515, 525, 535 and 545, respectively. The second liquid flows into liquid channels 550 and 560, as indicated by arrows 551 and 561. The second liquid entering liquid channel 550 may be the same as the second liquid entering the liquid channel 560, or it may be different. The difference between the second liquid entering liquid channel 550 and the second liquid entering liquid channel 560 may be based on composition or processing conditions, physical properties (e.g., viscosity, density, surface tension, etc.) and/or operating parameters. The second liquid entering liquid channel 550, as indicated by directional arrow 551, flows through the apertured sections 511 and 521, as indicated by directional arrows 552 and 553, into mixing zones 515 and 525, respectively. In the mixing zones 515 and 525, the second liquid contacts and mixes with the first liquid to form an emulsion. Similarly, a second liquid flows into liquid channel 560, as indicated by directional arrow 561, and then flows through apertured sections 531 and 541, as indicated by directional arrows 562 and 563, into mixing zones 535 and 545, respectively. In the mixing zones 515, 525, 535 and 545 the second liquids contact and mix with the first liquids to form the emulsions. The emulsions formed in mixing zones 515, 525, 535 and 545 can be the same or different. If different the emulsions may differ from one another with respect to composition and/or physical properties or operating parameters (e.g., composition of the dispersed and/or continuous phase, particle size, particle size distribution, viscosity, density, surface tension, temperature, pressure, flow rate, etc.). The emulsions formed in each of the process microchannels 510, 520, 530 and 540 may be water-in-oil emulsions, oil-in-water emulsions, or combinations thereof. For example, the emulsion formed in process microchannel 510 may be a water-in-oil emulsion while the emulsions formed in process microchannels 520, 530 and/or 540 may be oil-in-water emulsions, etc. Other combinations and permutations on which emulsions are water-in-oil and which are oil-in-water are possible. The emulsions flow from mixing zones 515, 525, 535 and 545 through non-apertured sections 516, 526, 536 and 546 out of the process microchannels 510, 520, 530 and 540, as indicated by directional arrows 518, 528, 538 and 548, respectively. Heating or cooling using heat exchange channels 570 and 580 may be optional. When heating or cooling is desired, heat exchange fluid flows through heat exchange channels 570 and 580, as indicated by directional arrows 571 and 572, and 581 and 582, and heats or cools the liquid in the channels 510, 520, 530, 540, 550 and 560. The degree of heating or cooling may vary over the length of each of the channels. The heating or cooling may be negligible or non-existent in some sections of the process channels and/or liquid channels, and moderate or relatively high in other sections. An advantage of this embodiment of the invention is that it may provide for the forming and evaluating of multiple product emulsions at the same time using the same apparatus. This can be advantageous when it is desired to screen multiple formulations as potential new products.

Although only one emulsion forming unit is fully illustrated in each of FIGS. 1-6, 33 and 34, there is practically no upper limit to the number of emulsion forming units that may be used in a microchannel mixer for conducting the inventive process. For example, one, two, three, four, five, six, eight, ten, twenty, fifty, one hundred, hundreds, one thousand, thousands, ten thousand, tens of thousands, one hundred thousand, hundreds of thousands, millions, etc., of the emulsion forming units described above may be used. In one embodiment, each emulsion forming unit may be manifolded. Manifolding may be effected by connecting macro-tubing, piping or ducting to each unit. Alternatively, many of the emulsion forming units may be internally manifolded within a microchannel mixer containing the emulsion forming units by creating relatively equal pressure drop circuits between each unit. On the other hand, the pressure drop may not be equal between each unit, as some flow maldistribution may not affect product quality. In one embodiment, up to about a 50% flow maldistribution may be acceptable in forming an emulsion using the inventive process. The process microchannels, and associated liquid channels and heat exchange channels may be aligned side-by-side or stacked one above another. For the emulsion forming units 100 and 10A, for example, the process microchannels 110 may be aligned in parallel in one plane, the liquid channels 170 may be aligned in parallel in an adjacent plane on one side of the process microchannels 110, and the heat exchange channels 190 may be aligned in parallel in another plane on the other side of the process microchannels 110. For the emulsion forming units 100B and 100C, for example, the process microchannels 110 may be aligned in parallel in one plane, the liquid channels 170 and 170*a* may be aligned in parallel in adjacent planes on each side of the process microchannels 110, and the heat exchange channels 190 may be aligned in parallel in a plane adjacent to the liquid channels 170*a*. For the emulsion forming unit 100D, the liquid channels 170 may be aligned in parallel in one plane, the process microchannels 110 and 110*a* may be aligned in parallel in adjacent planes on each side of the liquid channels 170, and the heat exchange channels 190 may be aligned in parallel in a plane adjacent to the process microchannel 110. These emulsion forming units may have appropriate headers, footers, manifolds, valves, conduit lines, tubings, control mechanisms, etc., to control the input and output of process liquids and heat exchange fluids which are not shown in FIGS. 1-6 and 33, but can be provided by those skilled in the art. For example, at the inlet and outlet to the microchannel mixer containing the emulsion forming units, sloped headers and footers may be used for connecting the conduit lines or tubings to avoid unnecessary pressure drops associated with the size of the process microchannels. The use of emulsion forming unit 100D in a microchannel mixer is further illustrated in FIGS. 16-20 discussed below.

In one embodiment, a plurality of emulsion forming units (100, 100A, 100B, 100C, 100D, 400 or 500) may be stacked one above another to form a core of units scaled up for on-demand large capacity. The scaled-up units may have sloped headers and footers as manifolds for the liquids used to form the emulsions as well as for the emulsion products. More uniform flow distribution may also be enhanced by the addition of an orifice plate or other apertured zone at the entrance of the process or dispersed phase or heat exchange channels. Frame sections may be used to hold and seal the emulsion forming units.

Each of the process microchannels (110, 110a, 410, 510, 520, 530, 540) may have a cross section that has any configuration, for example, square, rectangular, circular, annular, oval, trapezoidal, etc. The process microchannels (110, 110a, 410, 510, 520, 530, 540) may be tubular. The process microchannels (110, 110a, 410, 510, 520, 530, 540) may be formed from parallel spaced sheets or plates positioned side-by-side or one above another. The term "sheet" refers to a wall thickness of up to about 5 mm. The term "plate" refers to a wall thickness of about 5 mm or higher. Sheets may be supplied to the user in roll form while plates may be supplied to the user in the form of flat pieces of material. Each of the process microchannels (110, 110a, 410, 510, 520, 530, 540) has an internal dimension perpendicular to the flow of liquid through the process microchannel (for example, height, width or diameter) in the range of up to about 50 mm, and in one embodiment up to about 10 mm, and in one embodiment up to about 2 mm. This dimension may be in the range from about 0.05 to about 50 mm, and in one embodiment about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. Another internal dimension perpendicular to the flow of liquid through the process microchannel (for example, height or width) may be of any value, for example, it may be in the range from about 0.01 cm to about 100 cm, and in one embodiment from about 0.01 cm to about 75 cm, and in one embodiment from about 0.1 cm to about 50 cm, and in one embodiment about 0.2 cm to about 25 cm. The length of each of the process microchannels (110, 110a, 410, 510, 520, 530, 540) may be of any value, for example, in the range from about 0.1 cm to about 500 cm, and in one embodiment about 0.1 cm to about 250 cm, and in one embodiment about 1 cm to about 100 cm, and in one embodiment about 1 cm to about 50 cm, and in one embodiment about 2 cm to about 25 cm.

In one embodiment, the process microchannels (110, 110a, 410, 510, 520, 530, 540) may have a non-apertured or non-porous region (111, 111a, 411, 514, 524, 534, 544) in their entrances upstream of the mixing zones (113, 113a, 413, 515, 525, 535, 545) to provide an even distribution of flow of the first liquid in the process microchannels. This may be useful when multiple process microchannels are aligned side-by-side and/or one-above-another, and the flow of the first liquid into the multiple process microchannels is non-uniform. The provision of these non-apertured regions (111, 111a, 411, 514, 524, 534, 544) may stabilize the flow of the first liquid prior to reaching the mixing zones (113, 113a, 413, 515, 525, 535, 545). The use of the non-apertured regions (111, 111a, 411, 514, 524, 534, 544) may be advantageous when the process microchannels (110, 110a, 410, 510, 520, 530, 540) have circular cross sections (i.e., tubular geometries). In one embodiment, the ratio of the length of the non-apertured region (111, 111a, 411, 514, 524, 534, 544) from the entrance to the process microchannel (110, 110a, 410, 510, 520, 530, 540) to the entrance to the mixing zone (113, 113a, 413, 515, 525, 535, 545) relative to the smallest internal dimension of the process microchannel (110, 110a, 410, 510, 520, 530, 540) in the non-apertured region (111, 111a, 411, 514, 524, 534, 544) may be from about 0.0001 to about 10000, and in one embodiment about 0.001 to about 1000.

The liquid channels (170, 170a, 420, 430, 440, 450, 550, 560) may be microchannels although they may have larger dimensions that would not characterize them as microchannels. Each of these channels may have a cross section that has any configuration, for example, square, rectangular, circular, annular, oval, trapezoidal, etc. The liquid channels (170, 170a, 420, 430, 440, 450, 550, 560) may be tubular. The liquid channels (170, 170a, 420, 430, 440, 450, 550, 560) may be formed from parallel spaced sheets or plates positioned side-by-side or one-above-another. Each liquid channel may have an internal dimension perpendicular to the flow of liquid through the liquid channel (for example, height, width or diameter) in the range up to about 100 cm, and in one embodiment in the range from about 0.05 mm to about 100 cm, and in one embodiment about 0.05 mm to about 50 cm, and in one embodiment from about 0.05 mm to about 10 cm, and in one embodiment from about 0.05 mm to about 5 cm, and in one embodiment about 0.05 mm to about 10 mm, and in one embodiment about 0.05 mm to about 5 mm, and in one embodiment about 0.05 mm to about 2 mm, and in one embodiment about 0.05 mm to about 1 mm. Another internal dimension perpendicular to the flow of liquid through the liquid channel (for example, height or width) may be in the range from about 0.01 cm to about 100 cm, and in one embodiment about 0.01 cm to about 75 cm, and in one embodiment about 0.1 cm to about 50 cm, and in one embodiment about 0.2 cm to about 25 cm. The length of the liquid channels (170, 170a, 420, 430, 440, 450, 550, 560) may be of any value, for example, in the range from about 0.1 cm to about 500 cm, and in one embodiment about 0.1 cm to about 250 cm, and in one embodiment about 1 cm to about 100 cm, and in one embodiment about 1 cm to about 50 cm, and in one embodiment about 2 cm to about 25 cm. The separation between each process microchannel and the next adjacent liquid channel or between adjacent liquid channels may be in the range from about 0.05 mm to about 50 mm, and in one embodiment from about 0.1 to about 10 mm, and in one embodiment from about 0.2 mm to about 2 mm.

The heat exchanger may be used for cooling, heating or both cooling and heating. The heat exchanger may comprise one or more heat exchange channels (190, 570, 580), electric heating elements, resistance heaters and/or non-fluid cooling elements. These may be adjacent to the process microchannel, the liquid channel, or both the process microchannel and the liquid channel. In one embodiment, the heat exchanger may not be in contact with or adjacent to the process microchannel and/or liquid channel, but rather can be remote from either or both the process microchannel and liquid channel. The electric heating element, resistance heater and/or non-fluid cooling element can be used to form one or more walls of the process microchannels (110, 110a, 210, 410, 510, 520, 530, 540) and/or liquid channels (170, 170a, 270, 420, 430, 440, 450, 560, 570). The electric heating element, resistance heater and/or non-fluid cooling element can be built into one or more walls of the process microchannels and/or liquid channels. The electric heating elements and/or resistance heaters can be thin sheets, rods, wires, discs or structures of other shapes embedded in the walls of the process microchannels and/or liquid channels. The electric heating elements and/or resistance heaters can be in the form of foil or wire adhered to the process microchannel walls and/or liquid channel wall. Heating and/or cooling may be effected using Peltier-type thermoelectric cooling and/or heating elements. Multiple heating and/or cooling zones may be employed along the length of the process microchannels and/or liquid channels. Similarly, multiple heat exchange fluids at different temperatures may be employed along the length of the process microchannels and/or liquid channels. Cooling can be used to quench the emulsion after formation to enhance droplet stability. The heat exchanger can be use to provide precise temperature control within the process microchannels and/or liquid channels.

The heat exchange channels (190, 570, 580) may be microchannels although they may have larger dimensions that would not typically characterize them as microchannels. Each of these channels may have a cross section that has any configuration, for example, square, rectangular, circular, annular, oval, trapezoidal, etc. The heat exchange channels (190, 570, 580) may be tubular. The heat exchange channels (190, 570, 580) may be formed from parallel spaced sheets or plates positioned side-by-side or one-above-another. Each of the heat exchange channels may have an internal dimension perpendicular to the flow of heat exchange fluid through the heat exchange channel, for example height, width or diameter, in the range up to about 50 mm, and in one embodiment up to about 10 mm, and in one embodiment up to about 2 mm. This dimension may be in the range from about 0.05 to about 50 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. Another internal dimension perpendicular to the flow of heat exchange fluid through the heat exchange channel, for example height or width, may be of any value, for example, in the range from about 0.01 cm to about 100 cm, and in one embodiment about 0.01 cm to about 75 cm, and in one embodiment about 0.1 cm to about 50 cm, and in one embodiment about 0.2 cm to about 25 cm. The length of the heat exchange channels may be of any value, for example, in the range from about 0.1 cm to about 500 cm, and in one embodiment about 0.1 cm to about 250 cm, and in one embodiment about 1 cm to about 100 cm, and in one embodiment about 1 cm to about 50 cm, and in one embodiment about 2 cm to about 25 cm. The separation between each process microchannel or liquid channel and the next adjacent heat exchange channel may be in the range from about 0.05 mm to about 50 mm, and in one embodiment about 0.1 to about 10 mm, and in one embodiment about 0.2 mm to about 2 mm.

The heat exchange channels 190 illustrated in FIGS. 1-5 and the heat exchange channels 570 and 580 illustrated in FIG. 34 are adapted for heat exchange fluid to flow through the channels in a direction parallel to and co-current with the flow of liquid through the process microchannels (110, 110a, 510, 520, 530, 540) and liquid channels (170, 170a, 550, 560), as indicated by the directional arrows. Alternatively, the heat exchange fluid may flow through the heat exchange channels (190, 570, 580) in a direction opposite to the direction indicated in FIGS. 1-5 and 34, and thus flow countercurrent to the flow of liquid through the process microchannels (110, 110a, 510, 520, 530, 540) and liquid channels (170, 170a, 550, 560). Alternatively, the heat exchange channels (190, 570, 580) may be oriented relative to the process microchannels (110, 110a, 510, 520, 530, 540) and liquid channels (170, 170a, 550, 560) to provide for the flow of heat exchange fluid in a direction that is cross-current relative to the flow of liquid through the process microchannels (110, 110a, 510, 520, 530, 540) and liquid channels (170, 170a, 550, 560). The heat exchange channels (190, 570, 580) may have a serpentine configuration to provide a combination of cross-flow and co-current or counter-current flow.

In one embodiment, the process microchannels (110, 110a, 410, 510, 520, 530, 540), liquid channels (170, 170a, 420, 430, 440, 450, 550, 560) and heat exchange channels (190, 570, 580) have square or rectangular cross sections and are formed from parallel spaced sheets or plates. These channels may be aligned in side-by-side vertically oriented interleaved planes, or horizontally oriented interleaved planes stacked one above another. These configurations, which may be referred to as parallel plate configurations, have a number of advantages. In comparison with circular tubes, for example, parallel plate configurations incur less pressure drop while the same shear force is realized for the height or width, or diameter at the same continuous phase mass flux. When the aspect ratio of a rectangular channel approaches, for example, about 10, i.e., approaches a parallel sheet or plate configuration, its pressure drop may be only about 50% of that in a circular channel under the same conditions. Process microchannels, liquid channels and heat exchange channels having parallel plate configurations can be easily arranged in a compact device for scale-up. Also, a higher capacity per unit volume for the emulsion forming process can be achieved with parallel plate configurations as compared with circular tubes.

Figure 7:
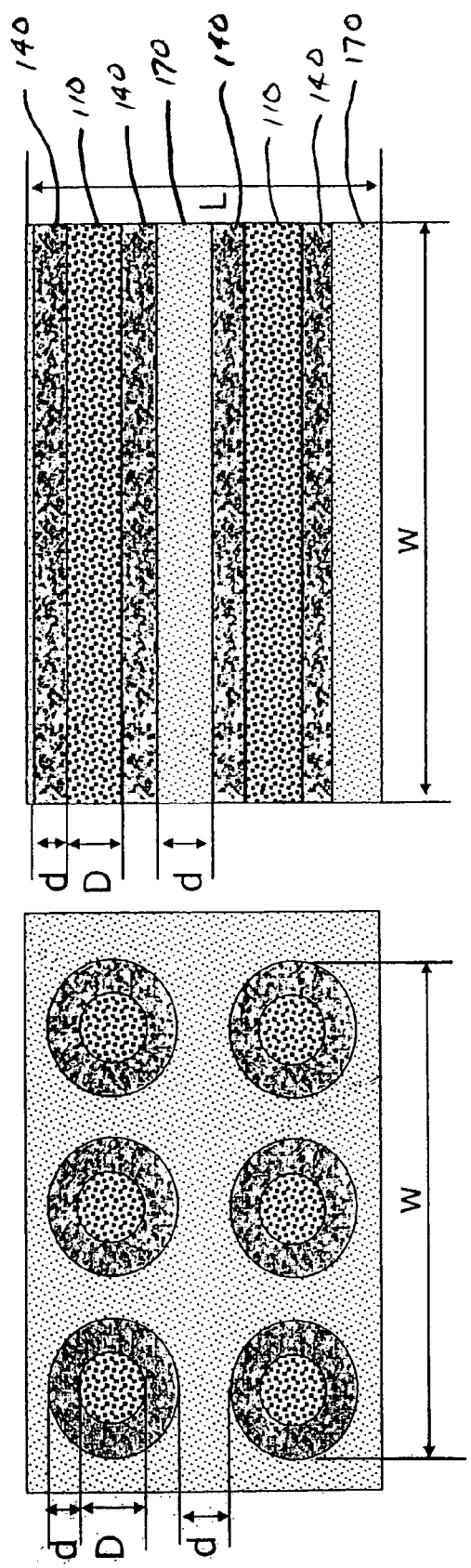
FIG. 7 provides a schematic illustration showing a comparison between rectangular channels having a parallel plate configuration and circular tubes for the flow of fluids through such channels and tubes.

An advantage of using parallel plate configurations is that these configurations have larger fluid/wall material ratios as compared to circular tubes, and are thus more compact with the potential for higher capacity or output. A comparison may be made at the same velocity (thus, similar shear force and droplet size) and the same dimensions d, D, L and W as depicted in FIG. 7. The comparison results are: continuous phase flow rate $G_{tube}=D\pi/[8(D+d)]G_{plate}$. When D=d, then $G_{tube}=0.196\ G_{plate}$. When d=D/2 then $G_{tube}=0262G_{plate}$. This means that for the same flow rate/capacity and system volume, the tube inner diameter has to increase by a factor of $(1/0.196)^{0.55}=2.25$ times or $(1/0.262)^{0.5}=1.954$ times. However, an increase of tube diameter leads to much lower shear force and in turn larger droplet size. In this case, the packing density becomes lower as the emulsification area has the following relation: when D=d, then $A_{tube}=0.39A_{plate}$; when d=D/2, then $A_{tube}=0.52A_{plate}$.

In one embodiment, the process microchannels (110, 110a, 410, 510, 520, 530, 540), liquid channels (170, 170a, 420, 430, 440, 450, 550, 560) and optionally heat exchange channels (190, 570, 580), may be in the form of circular tubes arranged concentrically. The process microchannels and liquid channels may be adjacent to each other with one channel being in the annular space and the other channel being in the center space or an adjacent annular space. In one embodiment, a microchannel mixer that is useful with the inventive process may comprise a plurality of alternating interleaved concentric tubular process microchannels, liquid channels, and optionally heat exchange channels, the microchannel mixer being in cylindrical form.

Figure 8:
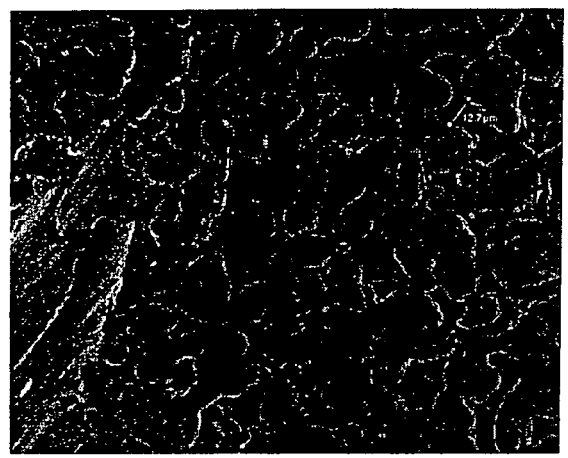
FIG. 8 is an SEM image of a porous stainless steel substrate before being heat treated.
Figure 9:
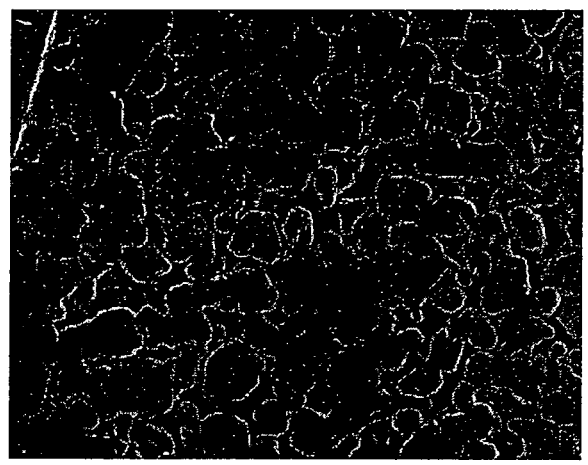
FIG. 9 is an SEM image of the substrate illustrated in FIG. 8 after being heat treated.

The apertures (144, 144a, 244, 416, 426, 436, 446, 513, 523, 533, 543) may be of sufficient size to permit the flow of the indicated liquids through the apertured sections. The apertures may be referred to as pores. The apertured section (140, 140a, 240, 415, 425, 435, 445, 511, 521, 531, 541) may have a thickness in the range from about 0.01 to about 50 mm, and in one embodiment about 0.05 to about 10 mm, and in one embodiment about 0.1 to about 2 mm. The apertures (144, 144a, 244, 416, 426, 436, 446, 513, 523, 533, 543) may have an average diameter in the range of up to about 50 microns, and in one embodiment in the range from about 0.001 to about 50 microns, and in one embodiment from about 0.05 to about 50 microns, and in one embodiment from about 0.1 to about 50 microns. In one embodiment, the apertures may have an average diameter in the range from about 0.5 to about 10 nanometers (nm), and in one embodiment about 1 to about 10 nm, and in one embodiment about 5 to about 10 nm. The number of apertures in the apertured sections may be in the range from about 10 to about $5\times10^8$ apertures per square centimeter, and in one embodiment about 1 to about $1\times10^6$ apertures per square centimeter. The apertures may or may not be isolated from each other. A portion or all of the apertures may be in fluid communication with other apertures within the apertured section. The ratio of the thickness of the apertured sections (140, 140a, 240, 415, 425, 435, 445, 511, 521, 531, 541) to the length of the apertured sections along the flow path of the liquids flowing through the process microchannels (110, 110a, 210, 410, 510, 520, 530, 540) may be in the range from about 0.001 to about 1, and in one embodiment about 0.01 to about 1, and in one embodiment about 0.03 to about 1, and in one embodiment about 0.05 to about 1, and in one embodiment about 0.08 to about 1, and in one embodiment about 0.1 to about 1. The apertured sections (140, 140a, 240, 415, 425, 435, 445, 511, 521, 531, 541) may be constructed of any material that provides sufficient strength and dimensional stability to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; microporous carbon, including carbon nanotubes or carbon molecular sieves; zeolites; or a combination of two or more thereof. The apertures may be formed using known techniques such as laser drilling, microelectro machining system (MEMS), lithography electrodeposition and molding (LIGA), electrical sparkling or electrochemical etching. The apertures may be formed using techniques used for making structured plastics, such as extrusion, or membranes, such as aligned carbon nanotube (CNT) membranes. The apertures may be formed using techniques such as sintering or compressing metallic powder or particles to form tortuous interconnected capillary channels and the techniques of membrane fabrication. The aperatures may be reduced in size from the size provided by any of these methods by the application of coatings over the apertures internal side walls to partially fill the apertures. The selective coatings may also form a thin layer exterior to the porous body that provides the smallest pore size adjacent to the continuous flow path. The smallest average pore opening may be in the range from about one nanometer to about several hundred microns depending upon the desired droplet size for the emulsion. The aperatures may be reduced in size by heat treating as well as by methods that form an oxide scale or coating on the internal side walls of the apertures. These techniques may be used to partially occlude the aperatures to reduce the size of the openings for flow. FIGS. 8 and 9 show a comparison of SEM surface structures of a stainless steel porous substrate before and after heat treatment at the same magnification and the same location. FIG. 8 shows the surface before heat treating and FIG. 9 shows the surface after heat treating. The surface of the porous material after the heat treatment has a significantly smaller gap and opening size. The average distance between the openings is correspondingly increased.

Figure 10:
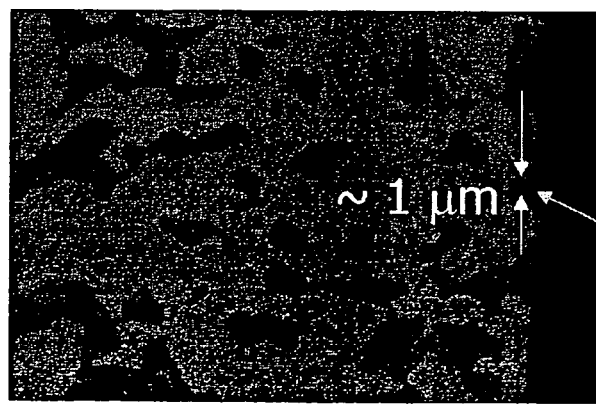
FIG. 10 is an SEM image of a tailored porous substrate useful with the inventive process.

The apertured sections (140, 140a, 240, 415, 425, 435, 445, 511, 521, 531, 541) may be made from a metallic or nonmetallic porous material having interconnected channels or pores of an average pore size in the range from about 0.01 to about 200 microns. These pores may function as the apertures (144, 144a, 244, 416, 426, 436, 446, 513, 523, 533, 543). The porous material may be made from powder or particulates so that the average inter-pore distance is similar to the average pore size. When very small pore sizes are used, the inter-pore distance may also be very small and the droplets may merge at the surface in the side of process microchannels (110, 110a, 210, 410, 510, 520, 530, 540) or liquid channels (420, 430) to form unwanted larger droplets. The porous material may be tailored by oxidization at a high temperature in the range from about 300° C. to about 1000° C. for a duration of about 1 hour to about 20 days, or by coating a thin layer of another material such as alumina by SOL coating or nickel using chemical vapor deposition over the surface and the inside of pores to block the smaller pores, decrease pore size of larger pores, and in turn increase the inter-pore distance. As such, the merger of droplets may be reduced or eliminated and the formation of smaller droplets may be permitted. An SEM image of a tailored substrate or apertured section is shown in FIG. 10.

The making of substrates for use as apertured sections (140, 140a, 240, 415, 425, 435, 445, 511, 521, 531, 541) with sufficiently small micro-scale apertures or pores (144, 144a, 244, 416, 426, 436, 446, 513, 523, 533, 543) to provide emulsions having droplet sizes smaller than about one micron can be problematic. One of the reasons for this lies in the fact that relatively high surface roughness occurs with untreated regular porous materials such as a metallic porous substrates made from powder/particles by compression and/or sintering. These metallic porous substrates typically do not have the required pore size in the surface region when a given nominal pore size is lower than a certain value. While the bulk of the porous material may have the specified nominal pore size, the surface region is often characterized by merged pores and cavities of much larger sizes. This problem can be overcome by tailoring these substrates to provide for the desired pore size and inter-pore distance in the surface region. This may be done by removing a surface layer from the porous substrate and adding a smooth new surface with smaller openings. The droplet size in the emulsion that may be formed using these tailored substrates may be reduced without increasing the pressure drop across the substrate. Since direct grinding or machining of the porous surface may cause smearing of the surface structure and blockage of the pores, the porous structure may be filled with a liquid filler, followed by solidification and mechanical grinding/polishing. The filler is then removed to regain the porous structure of the material. The filler may be a metal with a low melting point such as zinc or tin or the precursor of a polymer such as an epoxy. The liquid filling and removing steps may be assisted by the use of a vacuum. Grinding/polishing may be effected using a grinding machine and a grinding powder. Metal filler removal may be effected by melting and vacuum suction, or by acid etching. Epoxies or other polymers may be removed by solvent dissolution or by burn-off in air.

Figure 11:
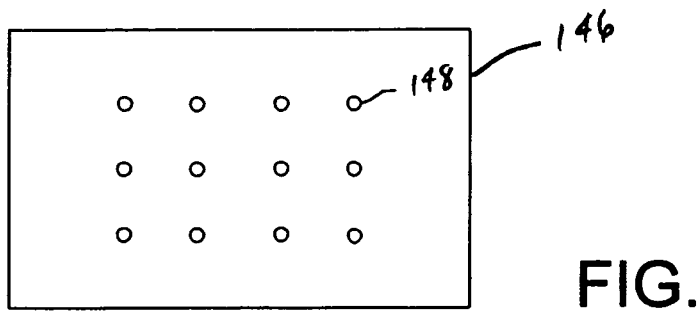
FIG. 11 is a plan view of an apertured sheet which is useful in making the apertured section of the process microchannel used with the inventive process.
Figure 12:
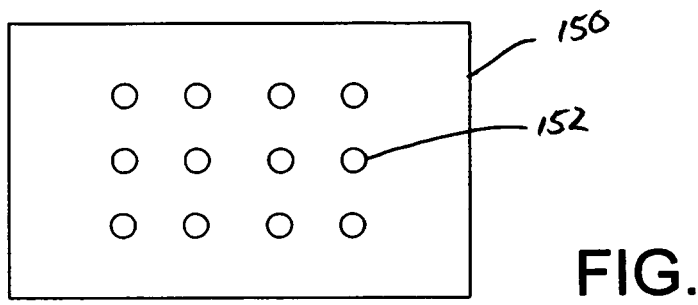
FIG. 12 is a plan view of an apertured sheet or plate which is useful in making the apertured section of the process microchannel used with the inventive process.
Figure 13:
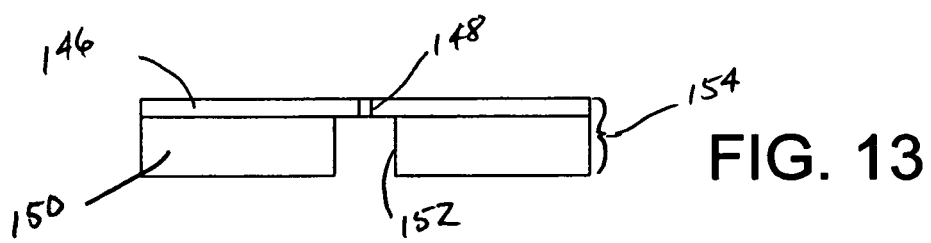
FIG. 13 is an illustration of a relatively thin apertured sheet overlying a relatively thick apertured sheet or plate which is useful in making the apertured section of the process microchannel used with the inventive process.

Referring to FIGS. 11-13, the apertured sections (140, 140a, 240, 415, 425, 435, 445, 511, 521, 531, 541), in one embodiment, may be constructed of a relatively thin sheet 146 containing relatively small apertures 148, and a relatively thick sheet or plate 150 containing an array of relatively large apertures 152 which are coaxially aligned with or connected to apertures 148. The relatively thin sheet 146 overlies and is bonded to the relatively thick sheet 150, the relatively thin sheet 146 facing the interior of process microchannel (110, 110a, 210, 410, 510, 520, 530, 540) or liquid channels (420, 430) and the relatively thick sheet 150 facing the interior of the liquid channel (170, 170a, 270, 420, 430, 440, 450, 550, 560). The relatively thin sheet 146 may be bonded to the relatively thick sheet 150 using any suitable procedure (e.g., diffusion bonding) to provide a composite construction 154 with enhanced mechanical strength. The relatively thin sheet 146 may have a thickness in the range from about 0.001 to about 0.5 mm, and in one embodiment about 0.05 to about 0.2 mm. The relatively small apertures 148 may have any shape, for example, circular, triangular or rectangular. The relatively small apertures 148 may have an average diameter in the range from about 0.05 to about 50 microns, and in one embodiment about 0.05 to about 20 microns. The relatively thick sheet or plate 150 may have a thickness in the range from about 0.1 to about 5 mm, and in one embodiment about 0.1 to about 2 mm. The relatively large apertures 152 may have any shape, for example, circular, triangular or rectangular. The relatively large apertures 152 may have an average diameter in the range from about 0.1 to about 4000 microns, and in one embodiment about 1 to about 2000 microns, and in one embodiment about 10 to about 1000 micron. The array of apertures 148 in sheet 146 and the array of apertures 152 in sheet or plate 150 may each comprise from about 2 to about 10000 apertures per square centimeter, and in one embodiment from about 2 to about 1000 apertures per square centimeter. The sheet 146 and the sheet or plate 150 may be constructed of any of the materials described above as being useful for constructing the apertured sections (140, 140a, 240, 415, 425, 435, 445, 511, 521, 531, 541). The apertures 148 and 152 may be coaxially aligned or connected in such a manner that liquid flowing through the apertured sections flows initially through apertures 152 then through apertures 148. The relatively short passageway for the liquid to flow through the relatively small apertures 148 enables the liquid to flow through the apertures 148 with a relatively low pressure drop as compared to the pressure drop that would occur if the passageway in the apertures had a length equal to the combined length of apertures 146 and 152.

Figure 14:
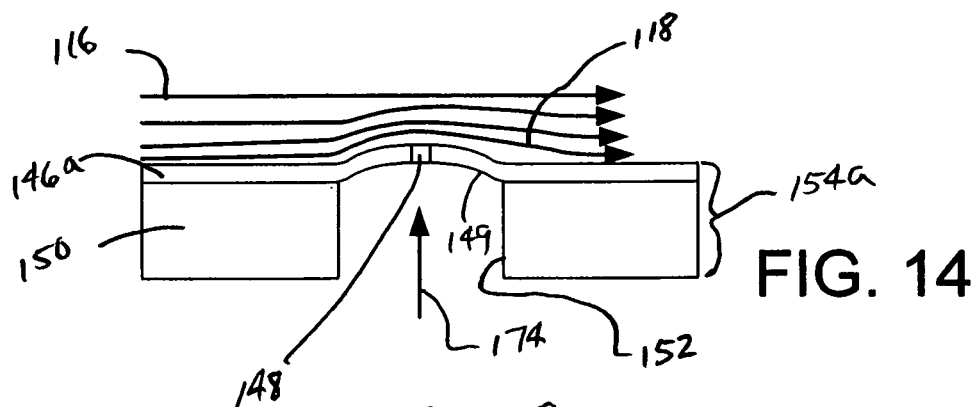
FIG. 14 is illustrative of a relatively thin apertured sheet overlying a relatively thick apertured sheet or plate which is useful in making the apertured section of the process microchannel used with the inventive process.

In the embodiment illustrated in FIG. 14, the composite construction 154a has the same design as illustrated in FIG. 13 with the exception that convex portion 149 of the relatively thin sheet 146 covering the aperture 152 is provided. Convex portion 149 provides increased local shear force in the adjacent channel. The directional arrows 116 and 118 in FIG. 14 showing the flow of liquid in the channel adjacent to the aperture 148. The higher shear force leads to a smaller droplet size for the liquid flowing through the aperture 148.

Figure 15:
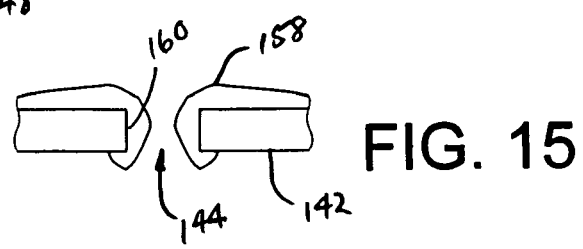
FIG. 15 is illustrative of an alternated embodiment of an aperture that may be used in the apertured section of the process microchannel used with the inventive process, the aperture having a coating partially filling it and overlying its sidewalls.
Figure 16:
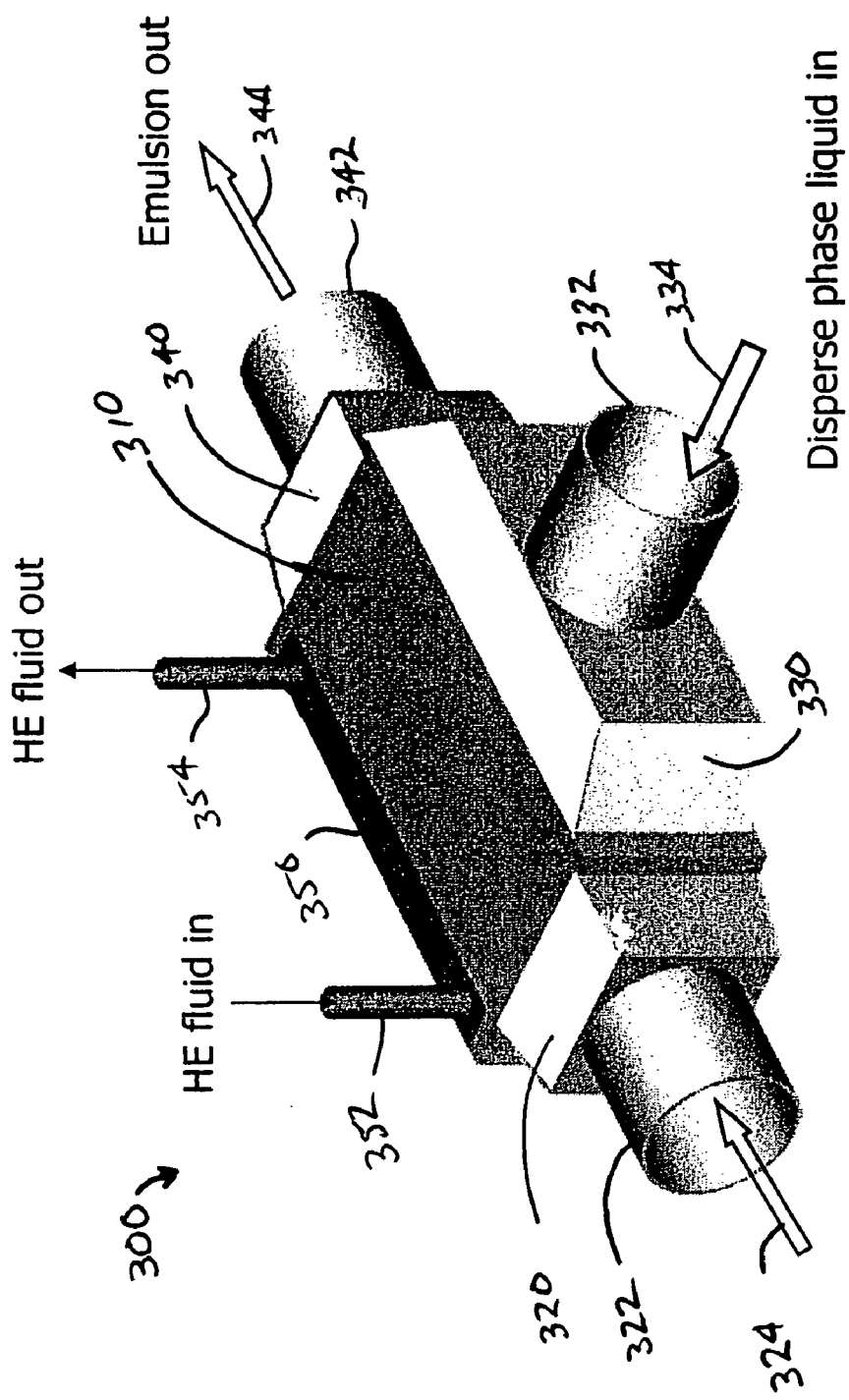
FIGS. 16-20 illustrate a mixing apparatus useful in conducting the inventive process.
Figure 17:
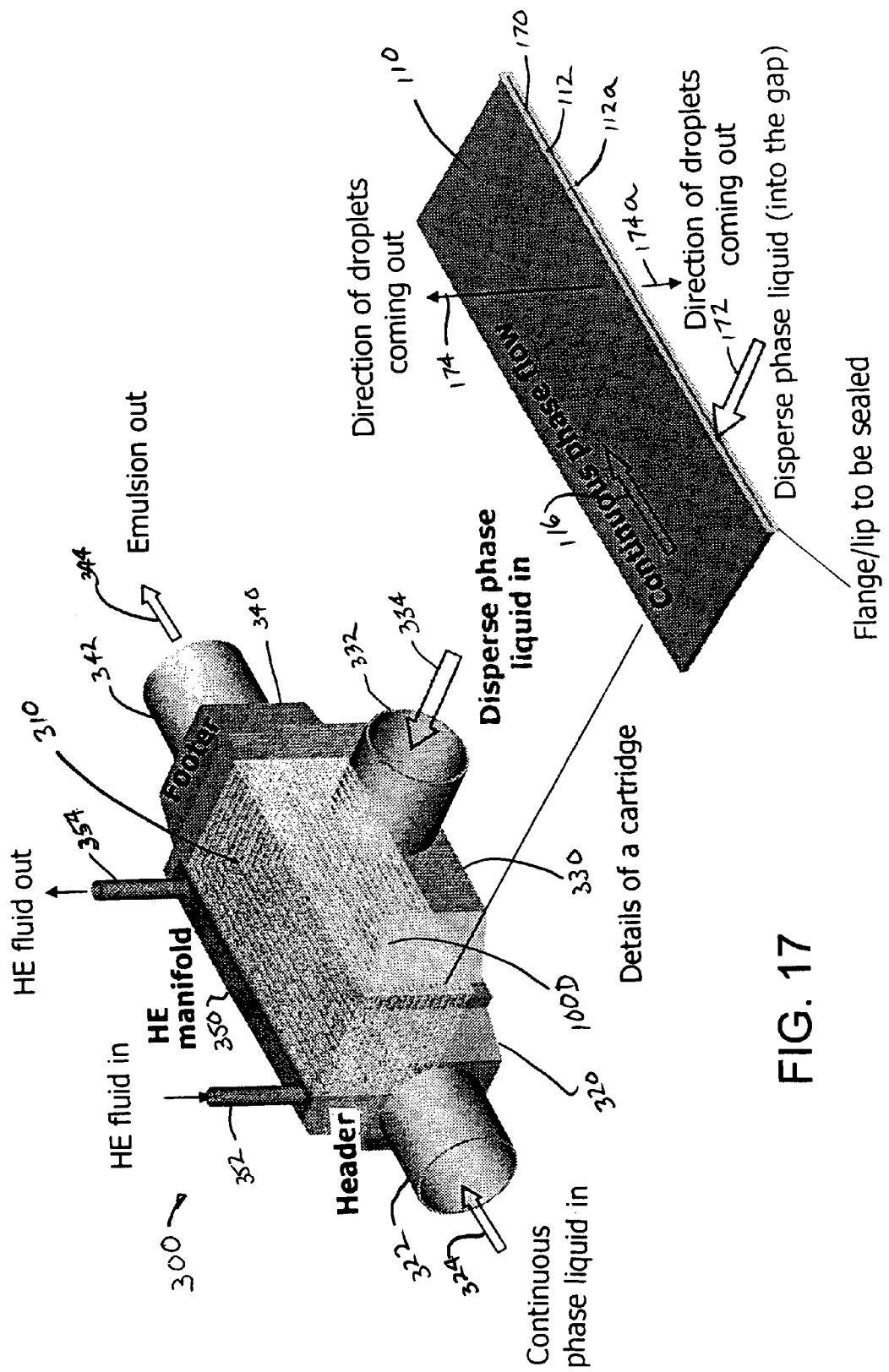

In the embodiment illustrated in FIG. 15, a surface coating 158 is deposited on the surface of sheet or plate 142 and on the internal sidewalls 160 of aperture 144. This coating provides a facilitated way of reducing the diameter of the apertures 144 (or apertures 144a, 244, 416, 426, 436, 446, 513, 523, 533, 543). The coating material used to form coating 158 may be alumina, nickel, gold, or a polymeric material (e.g., Teflon). The coating 158 may be applied to the sheet or plate 142 using known techniques including chemical vapor deposition, metal sputtering, metal plating, sintering, sol coating, and the like. The diameter of the apertures 144 (or apertures 144a, 244, 416, 426, 436, 446, 513, 523, 533, 543) may be controlled by controlling the thickness of the coating 158.

In one embodiment, the apertured sections (140, 140a, 240, 415, 425, 435, 445, 511, 521, 531, 541) may be formed from an asymmetric porous material, for example, a porous material having multiple layers of sintered particles. The number of layers may be two, three, or more. An advantage of these multilayered substrates is that they provide enhanced durability and adhesion. Examples include sintered ceramics that have relatively large pores on one side and relatively small pores on the other side. The relatively small pores may have diameters in the range of about 2 to about 10 nm. The relatively small pores may be positioned in a relatively thin layer of the multilayered substrate. The relatively thin layer may have a thickness in the range of about 1 to about 10 microns. The side with the relatively small pores may be placed facing the continuous phase flow (i.e., the interior of the process microchannel) to take advantage of relatively high shear forces to remove the relatively small emulsion droplets as they are formed.

Figure 18:
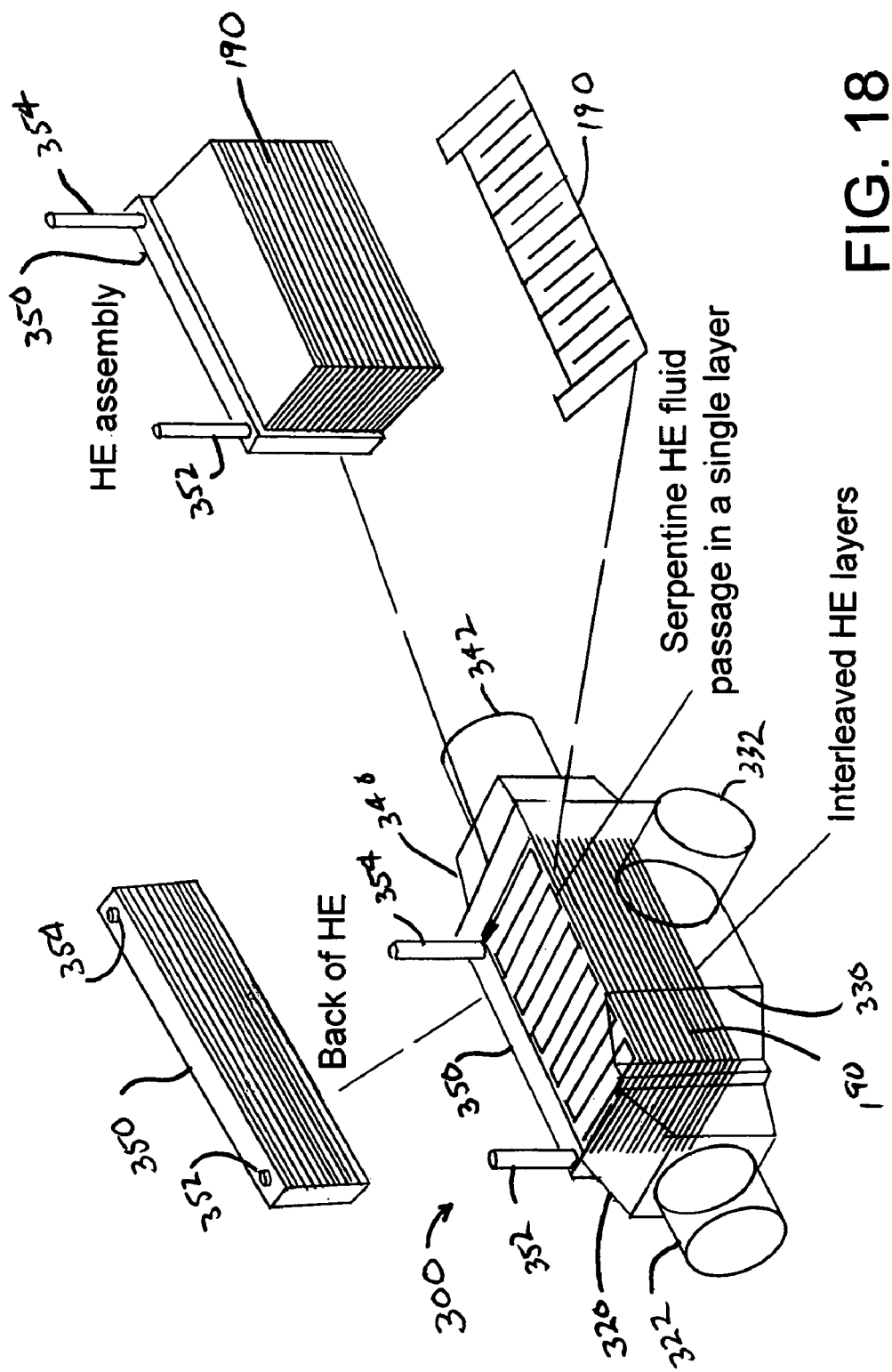
Figure 19:
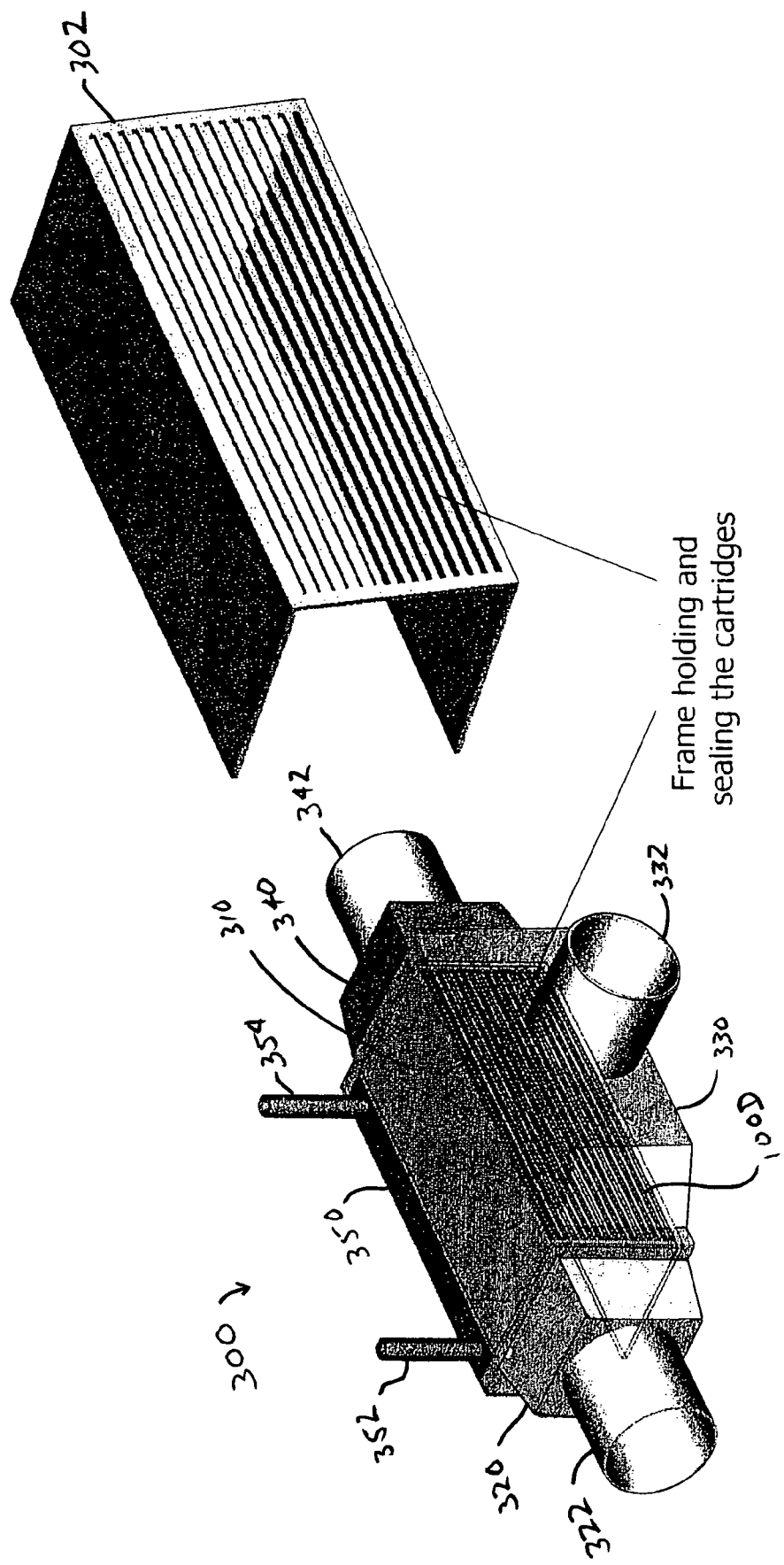
Figure 20:
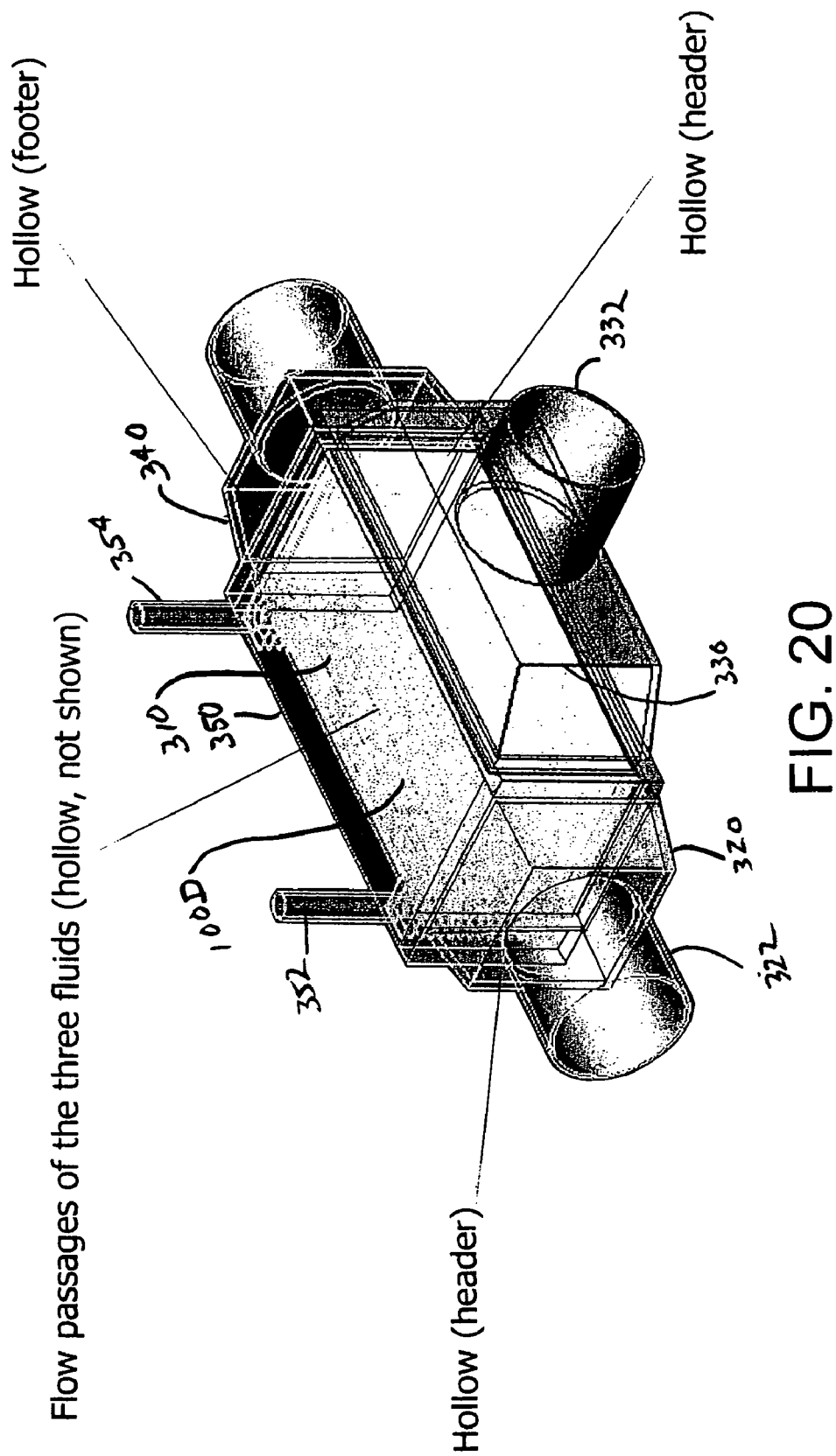

The emulsion forming units 100, 100A, 100B, 100C or 100D may be employed in the microchannel mixer 300 illustrated in FIGS. 16-20. Emulsion forming unit 100D is specifically shown in these drawings. Microchannel mixer 300 includes mixing core 310, sloped first liquid header 320, sloped second liquid header 330, sloped emulsion footer 340, and optional heat exchange manifold 350. The mixing core 310 may contain a plurality of the emulsion forming units 100, 100A, 100B, 100C or 100D stacked one above another. Frame section 302 may be used to hold and seal the emulsion forming units. The first liquid enters microchannel mixer 300 through conduit 322, as indicated by direction arrow 324. The first liquid flows through header 320 and from header 320 into the process microchannels 110 and 110a in the mixing core 310. The second liquid flows through conduit 332 into header 330, as indicated by directional arrow 334. The second liquid flows from header 330 into liquid channels 170. The liquid channels 170 may be in the form of flat, wide cartridges containing apertured sections (140, 140a) in parallel spaced opposed walls (112, 112a). These cartridges can be removed for maintenance or replacement. The second liquid flows through liquid channels 170 to and through apertured sections 140 and 140a into process microchannels 110 and 110a, respectively. The first liquid and second liquid are mixed in the process microchannels 110 and 110a to form the desired emulsion. The emulsion flows from the process microchannels 110 and 110a to and through product footer 340 and from product footer 340 to and through conduit 342 and out of the microchannel mixer, as indicated by directional arrow 344. Heat exchange fluid flows through heat exchange inlet 352 into heat exchange manifold 350. The heat exchange fluid flows from heat exchange manifold 450 through heat exchange channels 190 and from the heat exchange channels 190 back to the heat exchange manifold 350 where the heat exchange fluid exits through heat exchange fluid outlet 354. As indicated in FIG. 18, the heat exchange channel 190 has a serpentine configuration which provides a combination of cross-flow and either co-current or counter-current flow of the heat exchange fluid relative to the flow of the liquids in the process microchannels 110 and 110a and liquid channels 170. Alternatively, the flow path could be non-serpentine, that is, co-current or counter-current to the flow of the liquids in the process microchannels 110 and 110a and/or liquid channels 170.

The process microchannels (110, 110a, 210, 410, 510, 520, 530, 540), liquid channels (170, 170a, 270, 420, 430, 440, 450, 560, 570) and heat exchange channels (190, 570, 580) along with the associated headers, footers, manifolds, etc., may be made of any material that provides sufficient strength, dimensional stability, corrosion resistance and heat transfer characteristics to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof.

The first liquid and the second liquid may be immiscible relative to each other. The third liquid may be immiscible relative to the second liquid, and may or may not be immiscible relative to the first liquid. Each liquid may be organic, aqueous, or a combination thereof. For example, the first liquid may be benzene and the second liquid may be glycerol, or vice versa. One of the liquids may be an ionic liquid (e.g., a salt of 1-butyl-3-methylimidazolium) while another may be an organic liquid. One of the liquids may comprise water, and another liquid may comprise a hydrophobic organic liquid such as an oil. The emulsions made by the inventive process may be referred to as water-in-oil (w/o) or oil-in-water (o/w) emulsions. The double emulsions made by the inventive process may be referred to as water-in-oil-in-water (w/o/w) or oil-in-water-in-oil (o/w/o) emulsions. Throughout the specification and in the claims the term "oil" is sometimes used to refer to an organic phase of an emulsion although the organic material may or may not be an oil. The first liquid may be present in the emulsion made by the inventive process at a concentration in the range from about 0.1 to about 99.9% by weight, and in one embodiment about 1 to about 99% by weight, and in one embodiment about 5 to about 95% by weight. The second liquid may be present in the emulsion made by the inventive process at a concentration in the range from about 99.9 to about 0.1% by weight, and in one embodiment about 99 to about 1% by weight, and in one embodiment about 95 to about 5% by weight. The third liquid, when used, may be present in the emulsion made by the inventive process at a concentration in the range up to about 50% by weight, and in one embodiment from about 0.1 to about 20% by weight, and in one embodiment about 0.5 to about 10% by weight.

The first, second and/or third liquid may comprise one or more liquid hydrocarbons. The term "hydrocarbon" denotes a compound having a hydrocarbon or predominantly hydrocarbon character. These hydrocarbon compounds include the following:

(1) Purely hydrocarbon compounds; that is, aliphatic compounds, (e.g., alkane or alkylene), alicyclic compounds (e.g., cycloalkane, cycloalkylene), aromatic compounds, aliphatic- and alicyclic-substituted aromatic compounds, aromatic-substituted aliphatic compounds and aromatic-substituted alicyclic compounds, and the like. Examples include hexane, dodecane, cyclohexane, ethyl cyclohexane, benzene, toluene, the xylenes, ethyl benzene, styrene, etc.

(2) Substituted hydrocarbon compounds; that is, hydrocarbon compounds containing non-hydrocarbon substituents which do not alter the predominantly hydrocarbon character of the compound. Examples of the non-hydrocarbon substituents include hydroxy, acyl, nitro, halo, etc.

(3) Hetero substituted hydrocarbon compounds; that is, hydrocarbon compounds which, while predominantly hydrocarbon in character, contain atoms other than carbon in a chain or ring otherwise composed of carbon atoms. The hetero atoms include, for example, nitrogen, oxygen and sulfur.

The first, second and/or third liquid may comprise a natural oil, synthetic oil, or mixture thereof. The natural oils include animal oils and vegetable oils (e.g., castor oil, lard oil) as well as mineral oils such as liquid petroleum oils and solvent treated or acid-treated mineral oils of the paraffinic, naphthenic or mixed paraffinic—naphthenic types. The natural oils include oils derived from coal or shale. The oil may be a saponifiable oil from the family of triglycerides, for example, soybean oil, sesame seed oil, cottonseed oil, safflower oil, and the like. The oil may be a silicone oil (e.g., cyclomethicone, silicon methicones, etc.). The oil may be an aliphatic or naphthenic hydrocarbon such as Vaseline, squalane, squalene, or one or more dialkyl cyclohexanes, or a mixture of two or more thereof. Synthetic oils include hydrocarbon oils such as polymerized and interpolymerized olefins (e.g., polybutylenes, polypropylenes, propylene isobutylene copolymers, etc.); poly(1-hexenes), poly-(1-octenes), poly(1-decenes), etc. and mixtures thereof; alkylbenzenes (e.g., dodecylbenzenes, tetradecylbenzenes, dinonylbenzenes, di-(2-ethylhexyl)benzenes, etc.); polyphenyls (e.g., biphenyls, terphenyls, alkylated polyphenyls, etc.); alkylated diphenyl ethers and alkylated diphenyl sulfides and the derivatives, analogs and homologs thereof and the like. Alkylene oxide polymers and interpolymerso and derivatives thereof where the terminal hydroxyl groups have been modified by esterification, etherification, etc., are synthetic oils that may be used. The synthetic oil may comprise a poly-alpha-olefin or a Fischer-Tropsch synthesized hydrocarbon.

The first, second and/or third liquid may comprise a normally liquid hydrocarbon fuel, for example, a distillate fuel such as motor gasoline as defined by ASTM Specification D439, or diesel fuel or fuel oil as defined by ASTM Specification D396.

The first, second and/or third liquid may comprise a fatty alcohol, a fatty acid ester, or a mixture thereof. The fatty alcohol may be a Guerbet alcohol. The fatty alcohol may contain from about 6 to about 22 carbon atoms, and in one embodiment about 6 to about 18 carbon atoms, and in one embodiment about 8 to about 12 carbon atoms. The fatty acid ester may be an ester of a linear fatty acid of about 6 to about 22 carbon atoms with linear or branched fatty alcohol of about 6 to about 22 carbon atoms, an ester of a branched carboxylic acid of about 6 to about 13 carbon atoms with a linear or branched fatty alcohol of about 6 to about 22 carbon atoms, or a mixture thereof. Examples include myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. The fatty acid ester may comprise: an ester of alkyl hydroxycarboxylic acid of about 18 to about 38 carbon atoms with a linear or branched fatty alcohol of about 6 to about 22 carbon atoms (e.g., dioctyl malate); an ester of a linear or branced fatty acid of about 6 to about 22 carbon atoms with a polyhydric alcohol (for example, propylene glycol, dimer diol or trimer triol) and/or a Guerbet alcohol; a triglyceride based on one or more fatty acids of about 6 to about 18 carbon atoms; a mixture of mono-, di- and/or triglycerides based on one or more fatty acids of about 6 to about 18 carbon atoms; an ester of one or more fatty alcohols and/or Guerbet alcohols of about 6 to about 22 carbon atoms with one or more aromatic carboxylic acids (e.g., benzoic acid); an ester of one or more dicarboxylic acids of 2 to about 12 carbon atoms with one or more linear or branched alcohols containing 1 to about 22 carbon atoms, or one or more polyols containing 2 to about 10 carbon atoms and 2 to about 6 hydroxyl groups, or a mixture of such alcohols and polyols; an ester of one or more dicarboxylic acids of 2 to about 12 carbon atoms (e.g., phthalic acid) with one or more alcohols of 1 to about 22 carbon atoms (e.g., butyl alcohol, hexyl alcohol); an ester of benzoic acid with linear and/or branched alcohol of about 6 to about 22 carbon atoms; or mixture of two or more thereof.

The first, second and/or third liquid may comprise: one or more branched primary alcohols of about 6 to about 22 carbon atoms; one or more linear and/or branched fatty alcohol carbonates of about 6 to about 22 carbon atoms; one or more Guerbet carbonates based on one or more fatty alcohols of about 6 to about 22 carbon atoms; one or more dialkyl (e.g., diethylhexyl) naphthalates wherein each alkyl group contains 1 to about 12 carbon atoms; one or more linear or branched, symmetrical or nonsymmetrical dialkyl ethers containing about 6 to about 22 carbon atoms per alkyl group; one or more ring opening products of epoxidized fatty acid esters of about 6 to about 22 carbon atoms with polyols containing 2 to about 10 carbon atoms and 2 to about 6 hydroxyl groups; or a mixture of two or more thereof.

The first, second and/or third liquid may comprise water. The water may be taken from any convenient source. The water may be deionized or purified using osmosis or distillation.

Although emulsifiers and/or surfactants are not required for one or more embodiments of the invention, it is possible to use one or more emulsifiers and/or surfactants in forming the emulsions prepared by the inventive process. The emulsifiers and/or surfactant can be premixed with either the first, second and/or third liquid. The emulsifiers and/or surfactants may comprise ionic or nonionic compounds having a hydrophilic lipophilic balance (HLB) in the range of zero to about 18 in Griffin's system, and in one embodiment about 0.01 to about 18. The ionic compounds may be cationic or amphoteric compounds. Examples include those disclosed in *McCutcheons Surfactants and Detergents*, 1998, North American & International Edition. Pages 1-235 of the North American Edition and pages 1-199 of the International Edition are incorporated herein by reference for their disclosure of such emulsifiers. The emulsifiers and/or surfactants that may be used include alkanolamines, alkylarylsulfonates, amine oxides, poly(oxyalkylene) compounds, including block copolymers comprising alkylene oxide repeat units, carboxylated alcohol ethoxylates, ethoxylated alcohols, ethoxylated alkyl phenols, ethoxylated amines and amides, ethoxylated fatty acids, ethoxylated fatty esters and oils, fatty esters, fatty acid amides, glycerol esters, glycol esters, sorbitan esters, imidazoline derivatives, lecithin and derivatives, lignin and derivatives, monoglycerides and derivatives, olefin sulfonates, phosphate esters and derivatives, propoxylated and ethoxylated fatty acids or alcohols or alkyl phenols, sorbitan derivatives, sucrose esters and derivatives, sulfates or alcohols or ethoxylated alcohols or fatty esters, sulfonates of dodecyl and tridecyl benzenes or condensed naphthalenes or petroleum, sulfosuccinates and derivatives, and tridecyl and dodecyl benzene sulfonic acids. The emulsifiers and/or surfactants may comprise: one or more polyalkylene glycols; one or more partial esters of glycerol or sorbitan and fatty acids containing about 12 to about 22 carbon atoms; or a mixture thereof. The emulsifier and/or surfactant may comprise a pharmaceutically acceptable material such as lecithin. The concentration of these emulsifiers and/or surfactants in the emulsions made by the inventive process may range up to about 20% by weight of the emulsion, and in one embodiment in the range from about 0.01 to about 5% by weight, and in one embodiment from about 0.01 to about 2% by weight. In one embodiment, the concentration may be up to about 2% by weight, and in one embodiment up to about 1% by weight, and in one embodiment up to about 0.5% by weight.

The emulsions made by the inventive process may contain one or more of the following additives. These additives may be premixed with either the first, second and/or third liquid. These additives include: UV protection factors (e.g., 3-benzylidene camphor and derivatives thereof, 4-aminobenzoic acid derivatives, esters of salicylic acid, derivatives of benzophenone, esters of benzalmalonic acid, triazine derivatives, 2-phenylbenzimidazole-5-sulfonic acid and salts thereof, sulfonic acid derivatives of benzophenone and salts thereof, derivatives of benzoyl methane); waxes (e.g., candelilla wax, carnauba wax, Japan wax, cork wax, rice oil wax, sugar cane wax, beeswax, petrolatum, polyalkylene waxes, polyethylene glycol waxes); consistency factors (e.g., fatty alcohols, hydroxy fatty alcohols; partial glycerides, fatty acids, hydroxy fatty acids); thickeners (e.g., polysaccharides such as xanthan gum, guar-guar and carboxymethyl cellulose, polyethylene glycol monoesters and diesters, polyacrylates, polyacrylamides, polyvinyl alcohol, polyvinyl pyrrolidone); superfatting agents (e.g., lanolin, lecithin, polyol fatty acid esters, monoglycerides, fatty acid alkanolamides); stabilizers (e.g., metal salts of fatty acids, such as magnesium, aluminum or zinc stearate or ricinoleate); polymers (e.g., catonic polymers such as cationic cellulose derivatives, cationic starch, copolymers of diallyl ammonium salts and acrylamides, quaternized vinyl pyrrolidone/vinyl imidazole polymers, polyetheyneimine, cationic silicone polymers, polyaminopolyamides; anionic, zwitterionic, amphoteric and nonionic polymers); silicone compounds (e.g., dimethyl polysiloxanes; methyl phenyl polysiloxanes; cyclic silicones; amino-, fatty acid-, alcohol-, polyether-, epoxy-, fluorine-, glycoside-and/or alkyl- modified silicone compounds; simethicones; dimethicones); fats; waxes; lecithins; phospholipids; biogenic agents (e.g., tocopherol, ascorbic acid, deoxyribonucleic acid, retinol, amino acids, plant extracts, vitamin complexes); antioxidants (e.g., amino acids, imidazoles, peptides, carotinoids, carotenes, liponic acid and derivatives thereof, aurothioglucose, propylthiouracil, dilaurylthiodipropionate, sulfoximine compounds, metal chelators such as alpha-hydroxy fatty acids, alpha-hydroxy acids such as citric or lactic acid, humic acid, bile acid, EDTA, EGTA, folic acid and derivatives thereof, vitamin complexes such as vitamins A, C or E, stilbenes and derivatives thereof); deodorants; antiperspirants; antidandruff agents; swelling agents (e.g., montmorillonites, clay minerals); insect repellents; self-tanning agents (e.g., dihydroxyacetone); tyrosine inhibitors (depigmenting agents); hydrotropes (e.g., ethanol, isopropyl alcohol, and polyols such as glycerol and alkylene glycols used to improve flow behavior); solubilizers; preservatives (e.g., phenoxyethanol, formaldehyde solution, parabens, pentane diol, sorbic acid), perfume oils (e.g., extracts of blossoms, fruit peel, roots, woods, herbs and grasses, needles and branches, resins and balsams, and synthetic perfumes including esters, ethers, aldehydes, ketones, alcohols and hydrocarbons); dyes; and the like. The concentration of each of these additives in the inventive emulsions may be up to about 20% by weight, and in one embodiment from about 0.01 to about 10% by weight, and in one embodiment about 0.01 to about 5% by weight, and in one embodiment about 0.01 to about 2% by weight, and in one embodiment about 0.01 to about 1% by weight.

The inventive emulsions may contain one or more particulate solids. These may be premixed with the first, second and/or third liquid. The particulate solids may be organic, inorganic, or a combination thereof. The particulate solids may comprise catalysts (e.g., combustion catalysts such as $CeO_2/BaAl_{12}O_{19}$, $Pt/Al_2O_3$, etc., polymerization catalysts, and the like), pigments (e.g., $TiO_2$, carbon black, iron oxides, etc.), fillers (e.g., mica, silica, talcum, barium sulfate, polyethylenes, polytetrafluroethylene, nylon powder, methyl methacrylate powder), etc. The particulate solids may comprise nanosize particles. The particulate solids may have a mean particle diameter in the range of about 0.001 to about 10 microns, and in one embodiment about 0.01 to about 1 micron. The concentration of the particulate solids in the emulsions may range up to about 70% by weight, and in one embodiment from about 0.1 to about 30% by weight based on the weight of the emulsion.

In one embodiment, the emulsion made by the inventive process comprises a discontinuous phase dispersed in a continuous phase. The discontinuous phase may comprise droplets having a volume-based mean diameter of up to about 200 microns, and in one embodiment about 0.01 to about 200 microns, and in one embodiment about 0.01 to about 100 microns, and in one embodiment about 0.01 to about 50 microns, and in one embodiment about 0.01 to about 25 microns, and in one embodiment about 0.01 to about 10 microns, and in one embodiment about 0.01 to about 5 microns, and in one embodiment about 0.01 to about 2 microns, and in one embodiment about 0.01 to about 1 micron, and in one embodiment about 0.01 to about 0.5 micron, and in one embodiment about 0.01 to about 0.2 micron, and in one embodiment about 0.01 to about 0.1 micron, and in one embodiment about 0.01 to about 0.08 micron, and in one embodiment about 0.01 to about 0.05 micron, and in one embodiment about 0.01 to about 0.03 micron. In one embodiment, the discontinuous phase comprises water and the continuous phase comprises an organic liquid. In one embodiment, the discontinuous phase comprises an organic liquid and the continuous phase comprises water or another organic liquid. The continuous phase may contain particulate solids dispersed or suspended in the continuous phase. The discontinuous phase may contain particulate solids and/or droplets encapsulated within droplets in the discontinuous phase. An advantage of the inventive process is that at least in one embodiment the droplets may be characterized by having a relatively narrow distribution of droplet sizes. In one embodiment, the droplet sizes in the dispersed phase may be plotted with the result being a normal distribution curve.

"Relative span" is often referred to as "span." It is a dimensionless parameter calculated from volume distribution. As with volume median droplet size (VMD), D[v,0.1] and D[v,0.9] are diameters representing the points at which 10% and 90%, respectively, of the volume of liquid dispersed is in droplets of smaller diameter. The span may be defined as D[v,0.9] minus D[v,0.1] which is then divided by the VMD (D[v,0.5]). The span for the droplets in emulsions made by the inventive process may be in the range from about 0.005 to about 10, and in one embodiment about 0.01 to about 10, and in one embodiment about 0.01 to about 5, and in one embodiment about 0.01 to about 2, and in one embodiment about 0.01 to about 1, and in one embodiment about 0.01 to about 0.5, and in one embodiment about 0.01 to about 0.2, and in one embodiment about 0.01 to about 0.1. In one embodiment, the inventive process may be conducted in a single process microchannel and the span may be in the range of from about 0.01 to about 0.5. In one embodiment, the inventive process may be conducted in a scaled-up emulsification process employing multiple process microchannels and the span may be in the range from about 0.01 to about 1.

In one embodiment, the volume-based diameter for the droplets in the emulsions made by the inventive process may be in the range from about 0.01 to about 200 microns, and the span may be in the range from about 0.005 to about 10. In one embodiment, the volume-based mean diameter may be in the range from about 0.01 to about 100 microns, and the span may be in the range from about 0.01 to about 5. In one embodiment, the volume-based mean diameter may be in the range from about 0.01 to about 50 microns, and the span may be in the range from about 0.02 to about 5. In one embodiment, the volume-based mean diameter may be in the range from about 0.01 to about 10 microns, and the span may be in the range from about 0.05 to about 2.5. In one embodiment, the volume-based mean diameter may be in the range from about 0.01 to about 5 microns, and the span may be in the range from about 0.01 to about 2. In one embodiment, the volume-based mean diameter may be in the range of about 0.01 to about 1 micron, and the span may be in the range of about 0.005 to about 1.

Figure 32:
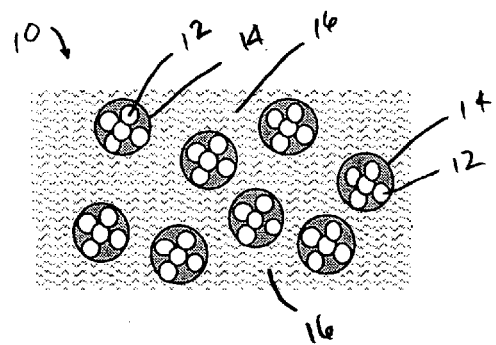
FIG. 32 is a s schematic illustration of a double emulsion, that is, a water-in-oil-in-water (w/o/w) or an oil-in-water-in-oil (o/w/o) emulsion.

As indicated above, the emulsion formed with the inventive process may be a double emulsion, that is, a w/o/w or o/w/o emulsion. These may be characterized by droplets of a third liquid encapsulated within droplets of a second liquid. The encapsulated droplets are dispersed in a continuous phase. This is illustrated in FIG. 32. Referring to FIG. 32, double emulsion 10 contains droplets 12 of a third liquid which are encapsulated within droplets 14 of a second liquid. The encapsulated droplets are dispersed in continuous phase 16 of a first liquid. The first liquid may or may not have the same composition as the third liquid. The droplets 12 may have a volume-based mean diameter of about 0.001 to about 10 microns, and in one embodiment about 0.01 to about 5 microns. The droplets 14 may have a volume-based mean diameter of about 0.001 to about 10 microns, and in one embodiment about 0.01 to about 5 microns. Any of the three phases in these double emulsions may contain particulate solids as discussed above. Double emulsions are used in various applications, such as in the drug, medical, food and cosmetic industries. An advantageous feature that can be provided by these double emulsions is to provide for a controlled disposal time and rate where an active ingredient in the third liquid is consumed in a later time, typically after or during the use or transport of the second liquid. Another feature is that an active ingredient in the third liquid can be separated from the first liquid and thus maintained unchanged during delivery before use when the active ingredient in the third liquid is chemically or physically incompatible with the first liquid or when the first liquid can only be used as a carrier liquid.

In one embodiment, the emulsion produced by the inventive process may be terminally filtered or filtered in-line. The use of such filtering is particularly suitable for producing emulsions such as pharmaceutical compositions where sterilization issues are significant. With such filtering relatively large particles of contaminants (e.g., biological materials) may be removed. In one embodiment, the inventive process includes providing for the filtering of the product emulsion in-line in a continuous closed (i.e., antiseptic) process.

Figure 21:
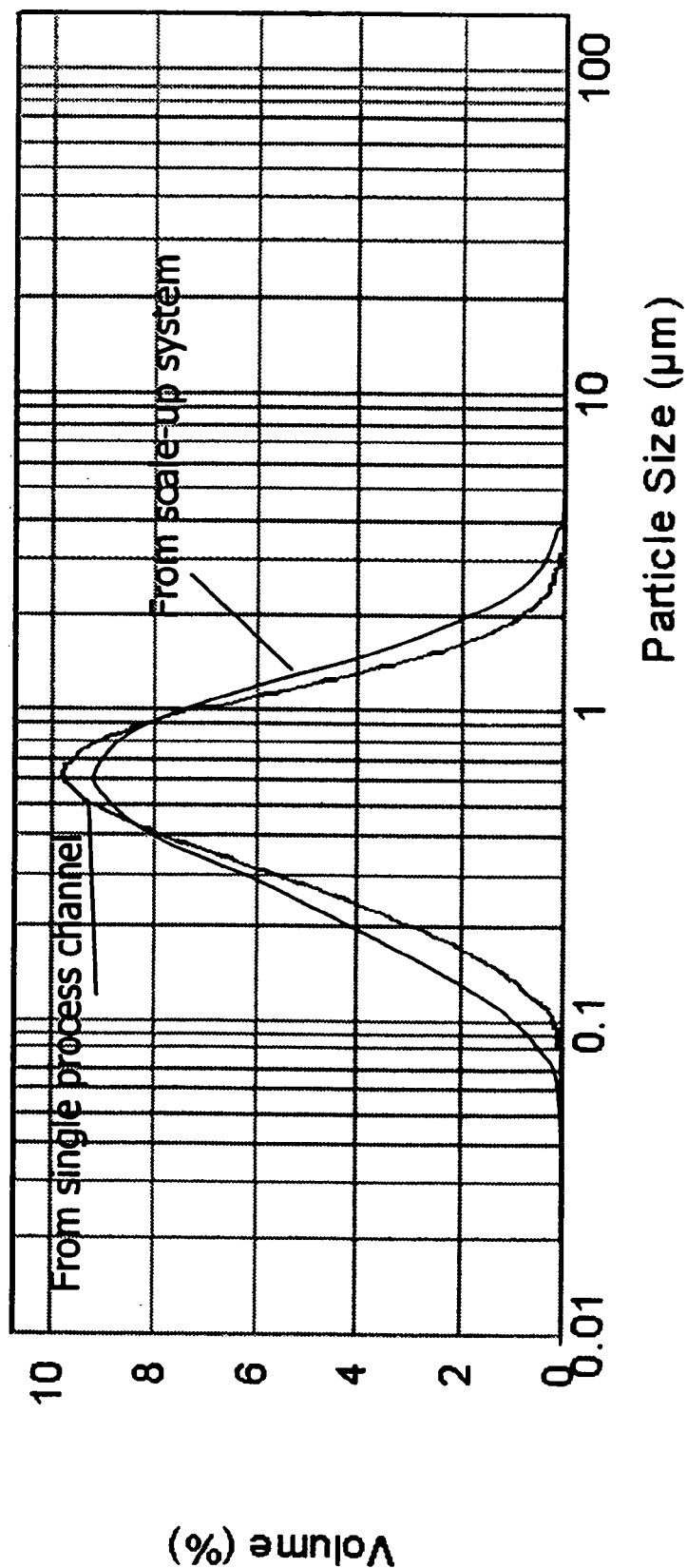
FIG. 21 shows particle size distribution curves for emulsions made in accordance with the inventive process wherein one of the curves is for an emulsion made using a single process microchannel and the other curve is for an emulsion made using a scaled-up system with multiple process microchannels.

An advantage of the inventive process, at least in one embodiment, is that the gap distances between the process microchannels, liquid channels and heat exchange channels may be the same whether the process is intended for laboratory or pilot plant scale or for full production scale. As a result, the particle size distribution of the emulsions produced by the microchannel mixers used with the inventive process may be substantially the same whether the microchannel mixer is built on a laboratory or pilot plant scale or as a full scale plant unit. This is shown by the particle size distribution curve presented in FIG. 21. The difference in the distribution curves provided in FIG. 21 for the single process channel and for the scale up system may result from an unwanted corner effect contribution. However, by making the edges opaque the unwanted effect of non-uniform shear force on droplet size can be minimized and thus the particle size distribution curve for the single process microchannel may be the same or substantially the same as that for the scale-up system.

Shear force on a liquid control element (in discretized form) in the direction of velocity u may be calculated by the formula $F_x$=mu*du/dy, where mu is viscosity, and du/dy is the velocity gradient for the liquid flow normal to the apertured section. However, as in a location of liquid (represented by a control element) the velocity generally has three components, and shear force also has three components. For a channel flow near and at the surface, a one dimensional assumption can be made and $F_x$ can approximate the net shear at an element surface of the liquid. The use of computational fluid dynamics, including commercial software packages such as Fluent or FEMLAB, may be used to solve the required transport equations such that the surface shear force may be calculated. The surface shear force may be calculated along the channel length, parallel to the direction of flow. Shear force may also be calculated between parallel channels, where flow distribution effects are included to determine the mass flux into each parallel channel as a function of the detailed channel and manifold geometry. Additional calculation methods can be found, for example, in "Fundamentals of Fluid Mechanics," $3^{rd}$ Ed., B. R. Munson, D. F. Young and T. H. Okiishi, John Wiley & Son, Inc., Weinheim, 1998.

In one embodiment, the shear force deviation factor (SFDF) for a process employing a single process microchannel may be within about 50% of the SFDF for a scaled-up process involving multiple process microchannels. SFDF may be calculated using the formula $$SFDF=(F_{max}-F_{min})/(2F_{mean})$$

wherein: $F_{max}$ is the maximum shear force in a process microchannel for a specific liquid; $F_{min}$ is the minimum shear force in the process microchannel for the liquid; and $F_{mean}$ is the arithmetic average shear force for the liquid at the surface of the apertured section (140, 140a, 240, 415, 425, 435, 445, 511, 521, 531, 541) within the process microchannel. Within a single process microchannel, operated in accordance with the inventive process, the SFDF may be less than about 2, and in one embodiment less than about 1, and in one embodiment less than about 0.5, and in one embodiment less than about 0.2.

In one embodiment, the inventive process may provide for a relatively uniform shear force while employing multiple process microchannels. To measure the shear force uniformity among multiple process microchannels, the average shear force is calculated for each channel and compared. $F_{max}$ is the largest value of the average channel shear force, and $F_{min}$ is the smallest value of the average shear force. $F_{mean}$ is the mean of the average shear forces of all the channels. SFDF may be calculated from these values. Among multiple process microchannels, at least with one embodiment of the inventive process, the SFDF may be less than about 2, and in one embodiment less than about 1, and in one embodiment less than about 0.5, and in one embodiment less than about 0.2.

A comparison of an emulsion made using the inventive process having a narrow distribution of droplet sizes to an emulsion made using a conventional batch emulsification process may be provided with reference to FIGS. 22 and 23. FIG. 22 is a microscopic image of an emulsion made by the inventive process while FIG. 23 shows an emulsion made by a conventional process. The droplets in FIG. 23 have a wide size distribution and larger droplet sizes. The droplets in FIG. 22 have a relatively narrow size distribution and smaller droplet sizes. The benefits of narrow droplet size distribution include, for example, uniform spread of active ingredients on an applied surface such as skin, and exclusions of unwanted small droplet penetration into small scale surface structures that may occur using an emulsion having a wide distribution. Another advantage relates to reducing the use of surfactants, as excess surfactant is often used to maintain a stable emulsion due to the presence of the smallest droplets if the emulsion droplet size distribution has a wide range, for example, from about 2 to about 20 microns. A narrow droplet size distribution enables a more accurate determination of the amount of surfactant that is just required, and in turn reduces or eliminates the use of unnecessary surfactant. In one embodiment of the present invention, when the droplet size distribution is sufficiently narrow, for example a span of less than about 0.5, the amount of surfactant that may be used can be reduced significantly since the emulsion does not contain unwanted small droplets that may require a higher surfactant concentration in the whole emulsion after production has been completed.

The heat exchange fluid may be any fluid. These include air, steam, liquid water, gaseous nitrogen, liquid nitrogen, other gases including inert gases, carbon monoxide, carbon dioxide, molten salt, oils such as mineral oil, gaseous hydrocarbons, liquid hydrocarbons, and heat exchange fluids such as Dowtherm A and Therminol which are available from Dow-Union Carbide.

The heat exchange fluid may comprise the first, second or third liquid used in making the emulsions. This can provide process pre-heat or pre-cooling and increase overall thermal efficiency of the process.

In one embodiment, the heatexchange channels comprise process channels wherein an endothermic or exothermic process is conducted. These heat exchange process channels may be microchannels. Examples of endothermic processes that may be conducted in the heat exchange channels include steam reforming and dehydrogenation reactions. In one embodiment, the incorporation of a simultaneous endothermic reaction to provide an improved heat sink may enable a typical heat flux of roughly an order of magnitude or more above the convective cooling heat flux. Examples of exothermic processes that may be conducted in the heat exchange channels include water-gas shift reactions, methanol synthesis reactions and ammonia synthesis reactions. The use of simultaneous exothermic and endothermic reactions to exchange heat in a microchannel reactor is disclosed in U.S. patent application Ser. No. 10/222,196, filed Aug. 15, 2002.

In one embodiment, the heat exchange fluid undergoes a phase change as it flows through the heat exchange channels. This phase change provides additional heat addition or removal from the process microchannels or liquid channels beyond that provided by convective heating or cooling. For a liquid heat exchange fluid being vaporized, the additional heat being transferred from the process microchannels would result from the latent heat of vaporization required by the heat exchange fluid. An example of such a phase change would be an oil or water that undergoes nucleate boiling. In one embodiment, the vapor mass fraction quality of the boiling of the phase change fluid may be up to about 50%.

The use of enhanced heat transfer from phase change or a chemical reaction may be more advantageous when emulsion generation occurs in coordination with a chemical reaction in the process channels. In one embodiment, the emulsion may be, for example, a reactive monomer for a polymerization reaction or other and as such require additional heat exchange.

The heat flux for convective heat exchange or convective cooling in the microchannel mixer may be in the range from about 0.01 to about 125 watts per square centimeter of surface area of the process microchannels ($W/cm^2$) in the microchannel mixer, and in one embodiment about 0.1 to about 50 $W/cm^2$, and in one embodiment about 1 to about 25 $cm^2$, and in one embodiment from about 1 to about 10 $W/cm^2$. The heat flux for phase change heat exchange may be in the range from about 1 to about 250 $W/cm^2$, and in one embodiment, from about 1 to about 100 $W/cm^2$, and in one embodiment from about 1 to about 50 $W/cm^2$, and in one embodiment from about 1 to about 25 $W/cm^2$, and in one embodiment from about 1 to about 10 $W/cm^2$.

The heat exchange channels may be used to provide sterile conditions during formation of the emulsions using the inventive process. Unlike batch mixers, the inventive process may be closed to the environment and does not need an inert gas blanket for isolation from the environment. The heat exchange channels, which may be adjacent to the process microchannels or liquid channels may provide relatively short heat transport and diffusion distances which permits rapid heating and cooling of the liquids in the microchannel mixer with decreased temperature gradients. As a result, emulsions that are not suitable for prolonged heating or would degrade under large temperature gradients may be prepared using the inventive process. In one embodiment, the temperature gradients between the process microchannel walls and the bulk flow within the process microchannels at the same axial position in the process microchannels may be less than about 5° C., and in one embodiment less than about 2° C., and in one embodiment less than about 1° C.

Heat exchange channels in close proximity to the process microchannels and/or liquid channels with controlled heating and/or cooling may provide for uniform temperature profiles between multiple process microchannels. This enables uniform heating and cooling at more rapid rates than can be obtained with conventional processing equipment such as mixing tanks. In a multichannel microchannel mixer, at least some axial position along the process flow length the temperature difference between the process microchannels may be less than about 5° C., and in one embodiment less than about 2° C., and in one embodiment less than about 1° C.

The heat exchange channels adjacent to either the process microchannels, liquid channels or both, may employ temperature zones along the length of such channels. In one embodiment, the temperature in a first zone near the entrance to the process channel is maintained at a temperature above a second temperature in a second zone near the end of the process microchannel. A cool down or quench zone may be incorporated into the process microchannel to quickly cool and stabilize the emulsion. Numerous combinations of thermal profiles are possible, allowing for a tailored thermal profile along the length of the process microchannel including the possibility of sections both before and/or after the mixing zone in the process microchannel to heat and/or cool the feed and or emulsion products.

The flow rate of liquid through the process microchannels (110, 110a, 410, 510, 520, 530, 540) may be in the range from about 0.001 to about 500 lpm, and in one embodiment about 0.001 to about 250 lpm, and in one embodiment about 0.001 to about 100 lpm, and in one embodiment about 0.001 to about 50 lpm, and in one embodiment about 0.001 to about 25 lpm, and in one embodiment about 0.01 to about 10 lpm. The velocity of liquid flowing through the process microchannels (110, 110a, 410, 510, 520, 530, 540) may be in the range from about 0.01 to about 100 m/s, and in one embodiment about 0.01 to about 75 m/s, and in one embodiment about 0.01 to about 50 m/s, and in one embodiment about 0.01 to about 30 m/s, and in one embodiment about 0.02 to about 20 m/s. The Reynolds Number for the liquid flowing through the process microchannels (110, 110a, 410, 510, 520, 530, 540) may be in the range from about 0.0001 to about 100000, and in one embodiment about 0.001 to about 10000. The temperature of the liquid entering the process microchannels (110, 110a, 410, 510, 520, 530, 540) may be in the range from about 0° C. to about 300° C., and in one embodiment about 20° C. to about 200° C. The pressure within the process microchannels (110, 110a, 410, 510, 520, 530, 540) may be in the range from about 0.01 to about 100 atmospheres, and in one embodiment about 1 to about 10 atmospheres. In the inventive process, a relatively high pressure drop across the apertured section (140, 140a, 415, 425, 435, 445, 511, 521, 531, 541) or a correspondingly high dispersion phase liquid flow rate through the liquid channel (170, 170a, 420, 430, 440, 450, 550, 560) may not be a necessary requirement to achieve the desired weight loading of the dispersed phase as is often the case in, for example, high pressure homogenizers. A low flow rate or low pressure drop may lead to a smaller droplet size with the inventive process, as lower inertia of the dispersion phase flow through the aperture reduces droplet growth before droplet breakup. This is shown schematically in FIG. 24.

The flow rate of liquid flowing through the liquid channels (170, 170a, 420, 430, 440, 450, 550, 560) may be in the range from about 0.05 to about 5000 ml/s, and in one embodiment about 0.1 to about 500 ml/s. The velocity of the liquid flowing through the liquid channels (170, 170a, 420, 430, 440, 450, 550, 560) may be in the range from about 0.0001 to about 0.1 m/s, and in one embodiment about 0.0001 m/s to about 0.05 m/s. The Reynolds Number for the liquid flowing through the liquid channels (170, 170a, 420, 430, 440, 450, 550, 560) may be in the range from about 0.0000001 to about 1000, and in one embodiment about 0.0001 to about 100. The temperature of the liquid entering the liquid channels (170, 170a, 420, 430, 440, 450, 550, 560) may be in the range from about −20° C. to about 250° C., and in one embodiment about 20° C. to about 100° C. The pressure within the liquid channels (170, 170a, 420, 430, 440, 450, 550, 560) may be in the range from about 1 to about 200 atmospheres, and in one embodiment about 1 to about 100 atmospheres. The pressure drop for the liquid flowing through the apertures (144, 144a, 416, 426, 436, 446, 513, 523, 533, 543) may be in the range from about 0.05 to about 200 atmospheres, and in one embodiment about 1 to about 150 atmospheres.

The emulsion exiting the process microchannels (110, 110a, 410, 510, 520, 530, 540) may be at a temperature in the range from about −20° C. to about 300° C., and in one embodiment about 0° C. to about 200° C.

The heat exchange fluid entering the heat exchange channels (190, 570, 580) may have a temperature in the range from about −50° C. to about 300° C., and in one embodiment about −10 to about 200° C., and in one embodiment about 0° C. to about 100° C. The heat exchange fluid exiting the heat exchange channels (190, 570, 580) may have a temperature in the range from about 0° C. to about 200° C., and in one embodiment about 10° C. to about 200° C. The pressure drop for the heat exchange fluid as it flows through the heat exchange channels may be in the range from about 0.01 to about 20 atmospheres, and in one embodiment from about 0.1 to about 20 atmospheres. The flow of the heat exchange fluid through the heat exchange channels may be laminar or in transition, and in one embodiment it is laminar. The Reynolds Number for the flow of heat exchange fluid flowing through the heat exchange channels may be in the range up to about 100000, and in one embodiment up to about 10000, and in one embodiment in the range from about 20 to about 10000, and in one embodiment about 100 to about 5000.

The first, second and/or third liquids may be preheated in the microchannel mixer or prior to entering the microchannel mixer using any type of heat exchange device, including a microchannel heat exchanger or heat pipe. In one embodiment, the first liquid may be preheated in the non-apertured region (111, 111a, 411, 514, 524, 534, 544) of the process microchannels (110, 110a, 410, 510, 520, 530, 540) upstream of the mixing zone (113, 113a, 413, 515, 525, 535, 545). The emulsion produced in the microchannel mixer may be cooled in the microchannel mixer or upon exiting the microchannel mixer using any type of heat exchange device, including a microchannel heat exchanger. In one embodiment, the emulsion may be quenched to stabilize the emulsion or lock it in. In one embodiment, the emulsion may be quenched in the non-apertured region (117, 117a, 516, 526, 536, 546) of the process microchannel (110, 110a, 510, 520, 530, 540). In one embodiment, the emulsion may be cooled to room temperature or quenched in a period in the range of up to about 10 minutes, and in one embodiment up to about 5 minutes, and in one embodiment up to about 1 minute, and in one embodiment up to about 30 seconds, and in one embodiment up to about 10 seconds, and in one embodiment in less than about 1 second.

The inventive process may be used to make an emulsion at a rate of at least about 0.01 liter per minute, and in one embodiment at least about 1 liter per minute. In one embodiment, the process may be used to make an emulsion at a rate of at least about 1 liter per second.

Figure 25:
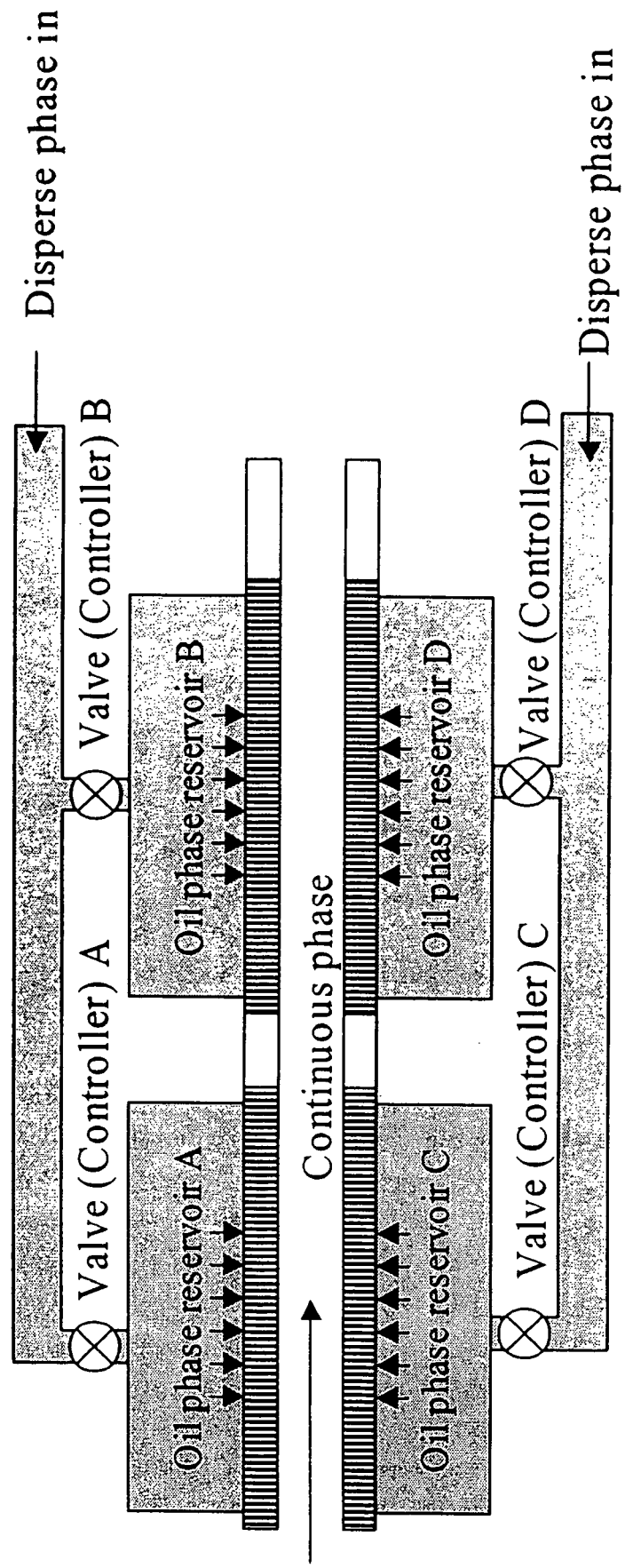
FIG. 25 is a flow sheet illustrating an alternate embodiment of the inventive process wherein multiple disperse phase reservoirs are used to form an emulsion containing multiple dispersed phases.

In one embodiment, multiple disperse phase liquid reservoirs or chambers may be built around the continuous phase channels, as illustrated in FIG. 25. The individual reservoirs or chambers may be separated and have their own inlet control mechanism such as valves. In this configuration the volumetric ratio of the two phases (packing density) may be controlled and changed according to different formulations of the desired product emulsions without changing other components such as aperture or pore size of the apertured section or individual flow rates of the continuous phase or the disperse phase. This is useful for an "one pass process" (i.e., without recirculation). For example, if all reservoirs or chambers A, B, C and D have the same oil flow rates and pore size, the emulsion packing density by closing valves A and B will be 50% of that by opening all valves. It is noted that various modifications of this concept are possible, for example more than two oil reservoirs or chambers can be configured on each side of the continuous phase channel. Multiple continuous phase channels may be parallel interleaved (sandwiched) to form an array of process channels. In FIG. 25, the disperse phase is identified as an oil phase, however, those skilled in the art will recognize that the dispersed phase may be any liquid that is immiscible with the continuous phase liquid. With this embodiment it is possible to produce emulsions having multi-modal droplet size distributions and/or multi-component dispersed phases. With this embodiment it is possible to provide for two or more second liquids entering the process microchannel through different apertured sections. This arrangement may be used to provide for multiple feed points for sequential additions of ingredients.

In one embodiment, optical or thermal-optical features may be adjusted in the process microchannel. Examples of techniques for measuring and/or adjusting these optical or thermal-optical features include: in-line LSD (laser scattering diffraction) detection for emulsion quality control and analysis including mean droplet size and span; viscometers for assessing product viscosity and solids loading; optical measurement using photographs for droplet size measurement; holographic imaging including interferometry via adjusting emulsion properties; and the like.

In one embodiment, a liquid adsorption process, a liquid-gas adsorption process, a liquid separation process, a solidification process, or a gasification process may be conducted in the process microchannel. In one embodiment, an emulsion may be produced in the process microchannels for applications wherein charged particles are tacked.

In one embodiment, a chemical reaction may be conducted in the process microchannel. Examples of the chemical reactions that may be conducted include polymerization reactions (e.g., methyl methacrylate emulsion polymerization reactions), catalytic polymerization reactions (e.g., ethylene polymerization in aqueous solution with neutral nickel (II) complexes as catalysts), production of copolymers and terpolymers, catalyzed and non-catalyzed reactions of liquid phase oxidations (e.g., the production of adipic acid) or gas-liquid phase reactions and catalyzed and non-catalyzed liquid-liquid reactions (e.g., nitration of benzene or olefin alkylation).

In one embodiment, a biological process may be conducted in the process microchannel. Examples of such biological processes include bioremediation (cleaning) processes using emulsified detergents.

In one embodiment, emulsions prepared in accordance with the inventive process provide the advantage of enabling the manufacturer to supply the emulsions in concentrate form, thus enabling the end user to add additional ingredients, such as water or oil, to obtain the final fully formulated product.

The emulsions made by the inventive process have numerous applications. These include personal skin care products wherein reduced concentrations of emulsifiers or surfactants are desirable (e.g., waterproof sun screen, waterproof hand creams or lotions).

The emulsions made by the inventive process may be useful as paints or coatings. These include water-resistant latex paints with strong weatherability characteristics. The emulsions may be useful as adhesives, glues, caulks, waterproof sealants, and the like. As a result of the inclusion of an aqueous phase in these compositions, the problem of volatile organic compounds (VOC) in these products can be reduced.

The inventive process may be used in various food processing applications, particularly continuous processing operations.

The inventive process may be used in the production of agricultural chemicals where the use of a dispersed phase with a narrow distribution of droplet sizes is advantageous for spreading the chemicals on leafs, and providing enhanced waterproofing with smaller concentrations of chemicals. In one embodiment, the inventive process may be used in the production of agricultural chemicals such as pesticides wherein it may be desired to employ a droplet size for the dispersed phase that is smaller than the wavelength of visible light.

The inventive process may be used for the production of emulsified lubricants and fuels. These may include on-board fuel emulsification systems such as those used for diesel engines.

The inventive process may be used in emulsion polymerization processes. For example, it may be possible to solublize monomers in a surfactant with a catalyst. The inventive process may be used to make rapid setting emulsions containing bitumen. These emulsions may be used as surface dressings for cement or asphalt surfaces such as roads, driveways, and the like. These emulsions may contain from about 60 to about 70% by weight bitumen and may be sprayed onto the surface being treated. Chippings may be spread on top of these surface dressings and rolled to ensure proper embedding and alignment. This provides a water impervious surface seal and also an improved surface texture.

The emulsions made using the inventive process may be silicone emulsions. These emulsions may be used for treating fibers and other substrates to alter their water repellant properties. The inventive process may be used in a crystallization process, for example, a continuous crystallization process. This process may be used to isolate, purify and/or produce powders of a specified size. An example of such crystals include highly refined sugar. In emulsion crystallization, a melt may be crystallized within droplets of the emulsion so that homogeneous nucleation may occur at a lower rate than in a bulk melt. This process may be conducted without solvents, and thus may provide the advantage of low capital and operating costs. The inventive process may be used to make liquid crystals. The liquid crystals formed in the process may help to reduce the use of emulsifiers and/or surfactants, as the dispersed phase may be "locked" in place.

The inventive process may be used to make wax emulsions for adhesives, liquid soaps, laundry detergents, coatings for textiles or fabrics, and the like.

The inventive process may be used in the manufacture of pharmaceuticals wherein the provision of a dispersed oil phase with a narrow distribution of droplet sizes is advantageous. These may include oral or injectable compositions as well as dermatological creams, lotions and opthalmics. The droplet size and distribution achieved with the inventive process may increase the efficacy of the drug and provide for reduced levels of use of the drug for required treatments. This also provides the advantage of avoiding or limiting the use of non-aqueous solvent components which tend to solubilize organic substances used in packaging materials. The droplet size for the dispersed oil phase for these applications may be up to about 0.5 micron, in order to avoid being eliminated by the spleen or liver, and in one embodiment in the range from about 0.01 to about 0.2 micron, and in one embodiment 0.01 to about 0.1 micron. The emulsions produced by the inventive process may function as emulsion vehicles for insoluble or poorly soluble drugs (e.g., ibuprofen, diazepam, griseofulvin, cyclosporin, cortisone, proleukin, etoposide, paclitaxel, cytotoxin, vitamin E, alpha-tocopherol, and the like). Many of the pharmaceutical compounds or drugs, oils and surfactants disclosed in U.S. Patent Application Publication No. 2003/0027858A1 may be used in making pharmaceutical compositions using the inventive process; this patent publication is incorporated herein by reference for its disclosure of such compounds or drugs, oils and surfactants. An advantage of using the inventive process relates to the fact that many of the problems associated with using conventional high-shear mixing equipment for attempting to achieve small droplets with a narrow droplet size distribution while maintaining a sterile environment are avoided.

EXAMPLE 1

Figure 26:
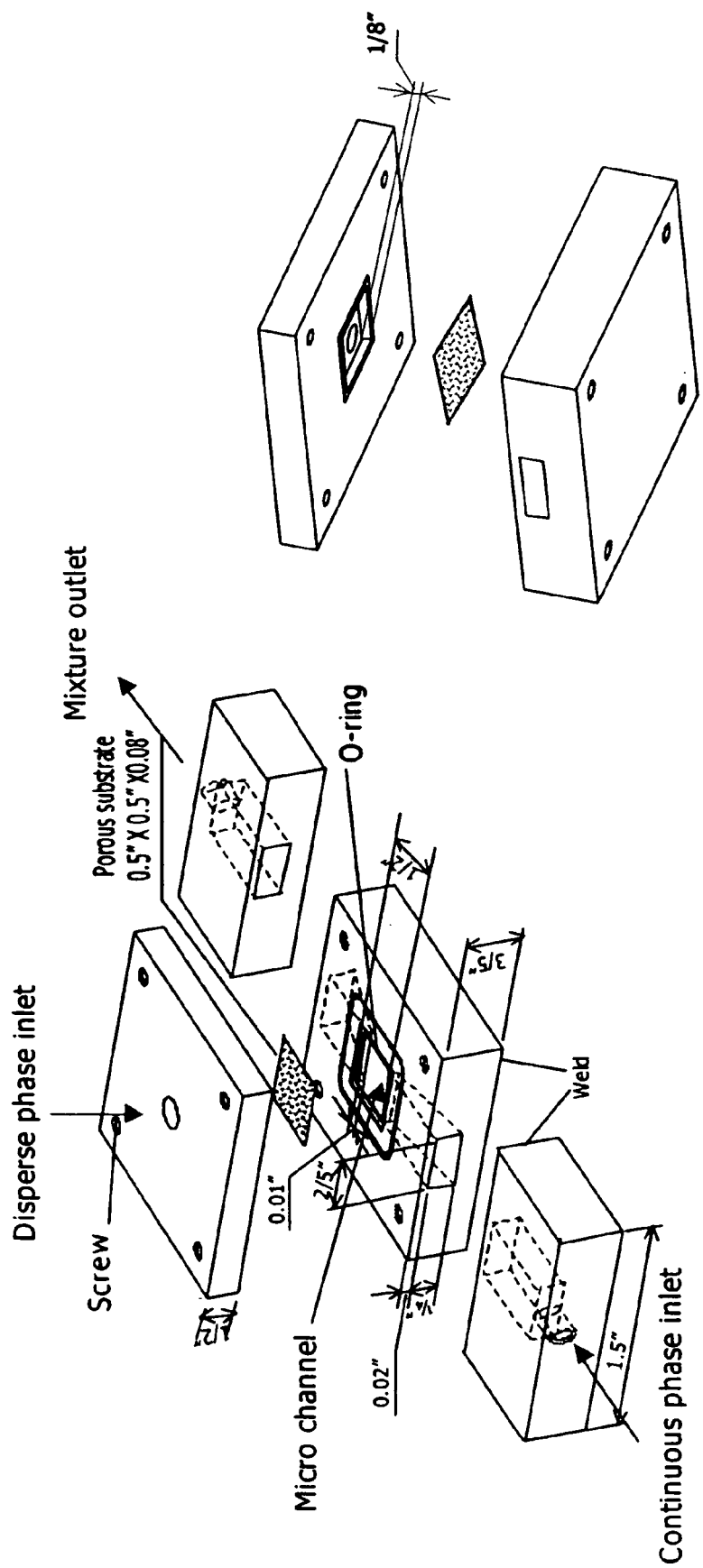
FIG. 26 is a schematic illustration of the microchannel device used in Example 1.

The microchannel device illustrated in FIG. 26 is made from stainless steel and used to form an oil-in-water emulsion. The device includes a base part for continuous phase flow, a top part for delivering a discontinuous oil phase, a porous substrate, a header, a footer, and tubing and piping to provide for the flow of liquids to the microchannel device.

The base part, which has an overall size of $\frac{3}{8} \times 1.5 \times 1.5$ inches, has an open microchannel having the dimensions of $0.02 \times 0.5 \times 0.5$ inch, and sloping inlet and outlet flow passageways (0.5 inch long, 0.5 inch wide, slopping angle 27°) that are connected via welding with the header and footer for the continuous phase liquid. The edge of the open microchannel has a lip (step) with a width of 0.02 inch for mounting the porous substrate via rubber gasket of thickness 0.005 inch for sealing. With the mounting of the porous substrate ($0.5 \times 0.5 \times 0.04$ inch), a microchannel is formed for providing high velocity flow of a continuous phase and generating micro-scale droplets as a dispersed phase in the continuous phase.

The top part comprises a built-in oil chamber (see right-side figure in FIG. 26) connected to an oil pipe line (not shown in the drawing). The header and footer (the parts with slope and connected spaces) are designed for flow area transition from ordinary tubes to the microchannel with a small gap (less than 1 mm), while the overall pressure drop is maintained at a reasonable value depending upon the pump and heating capacity.

Figure 27:
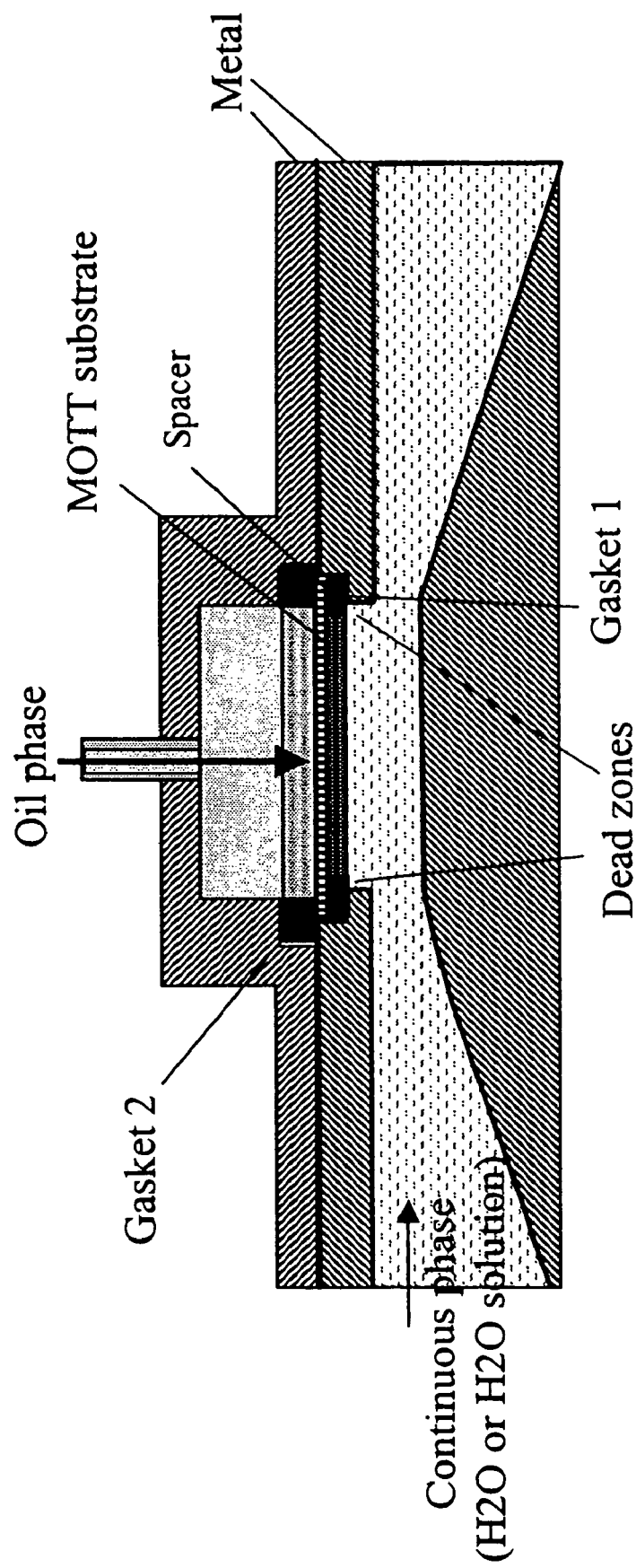
FIG. 27 is another schematic illustration of the microchannel device used in Example 1.

A schematic of the basic structure is illustrated in FIG. 27. The porous substrate is a heat treated porous substrate supplied by MOTT Metallurgical Corp. of Farmington, Conn. The porous substrate is made from stainless steel 316. The average diameter of each pore is 0.5 micron. The porous substrate separates the disperse phase liquid chamber from the continuous phase liquid channel. A pressure difference (10 to 20 psia) during the emulsification operation drives the disperse phase liquid through the porous substrate into the continuous liquid channel which results in the formation of droplets in the continuous phase.

Figure 28:
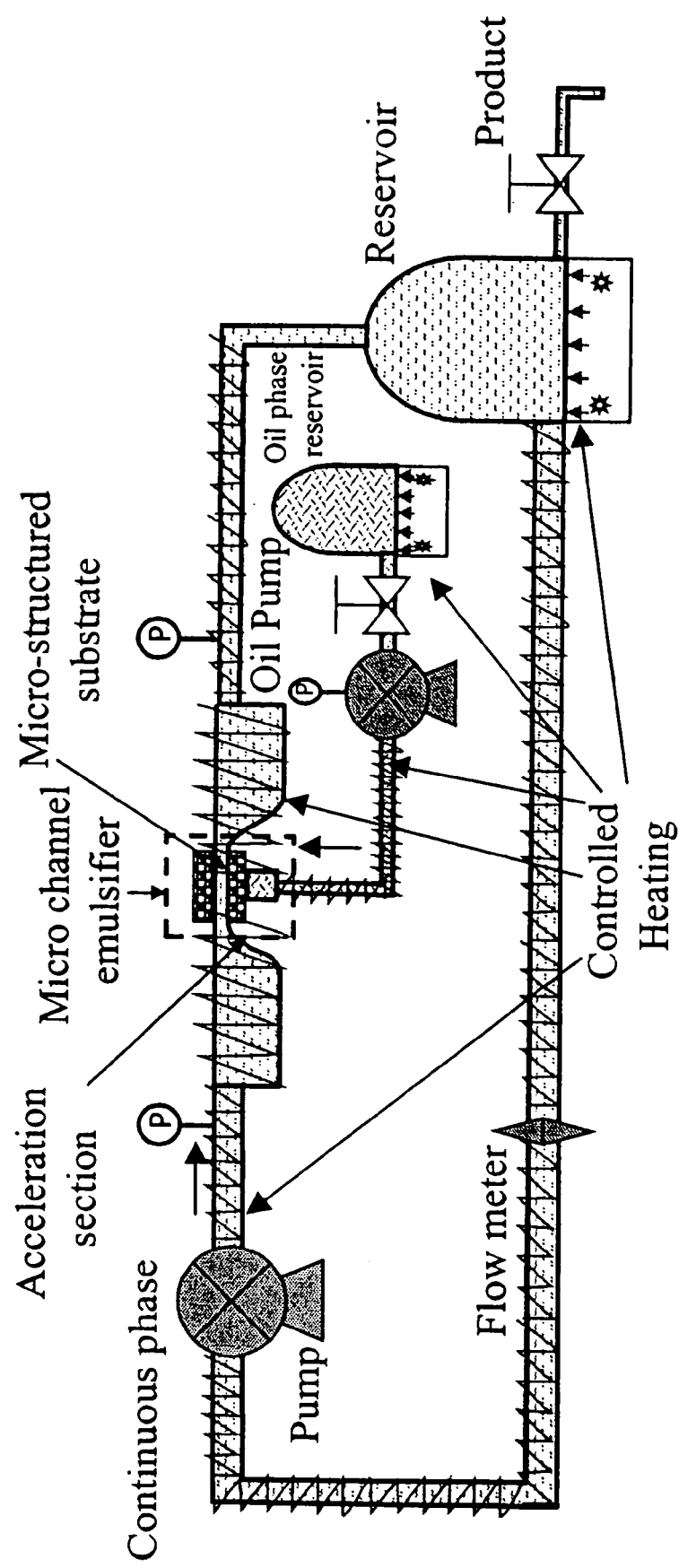
FIG. 28 is a flow sheet illustrating the emulsification system used in Example 1.

The emulsification system is illustrated in FIG. 28. This system includes an oil pump (FMI "Q" pump, Model QG6 from FluidMetering, Inc, Syosset, N.Y.), a water pump with a flow rate dial (Micropump Model GJ-N25, JF18A from Cole Parmer, Vernon Hills, Ill.), a heated oil reservoir, a continuous phase liquid reservoir, and metallic tubings (¼") connecting the pumps and the microchannel emulsifier. An extra rotor flow meter (Cole Parmer) is installed to record the actual flow rate and for later calibration. By installing heating tapes around most of the metallic tubing, exposed components as well as the microchannel device and by feed-back controlling the heating power via TC signals from multiple key locations, all components and the liquids in the system are maintained at a temperature that is higher than the ambient. The components to be heated up and controlled include the microchannel emulsifier, oil pump and reservoir, and water reservoir. The reservoirs have inside volume scales.

Before being used for emulsification, the porous substrate is cleaned and heat-treated. The following cleaning procedure is used.
1. Sonicate in hexane for 5 min. If the porous substrate is pre-exposed to oil, repeat hexane sonication once with fresh hexane.
2. Air dry at room temperature over night, or at 80° C. for 10-20 minutes in a drying oven.
3. Sonicate the porous substrate in 20% nitric acid for 20 minutes.
4. Sonicate the porous substrate in fresh deionized water for 5 minutes.
5. Repeat step #4 at least three times to achieve pH reading of the water of over 5.
6. Sonicate the porous substrate in acetone or isopropanol for 3 minutes.
7. Air dry at room temperature overnight, or at 80° C. for 10-20 minutes in a drying oven.

The porous substrate is then heat treated in a heat treatment vessel using the following procedure:
1. Evacuate and refill with nitrogen three times.
2. Heat in the presence of hydrogen and water to 650° C. at a rate of 3.5° C. per minute.
3. Maintain temperature at 650° C. for 30 minutes with nitrogen flow.
4. Maintain temperature at 650° C. in air for 100 hours.
5. Cool in air to room temperature at a rate of 3.5° C. per minute.

Figure 29:
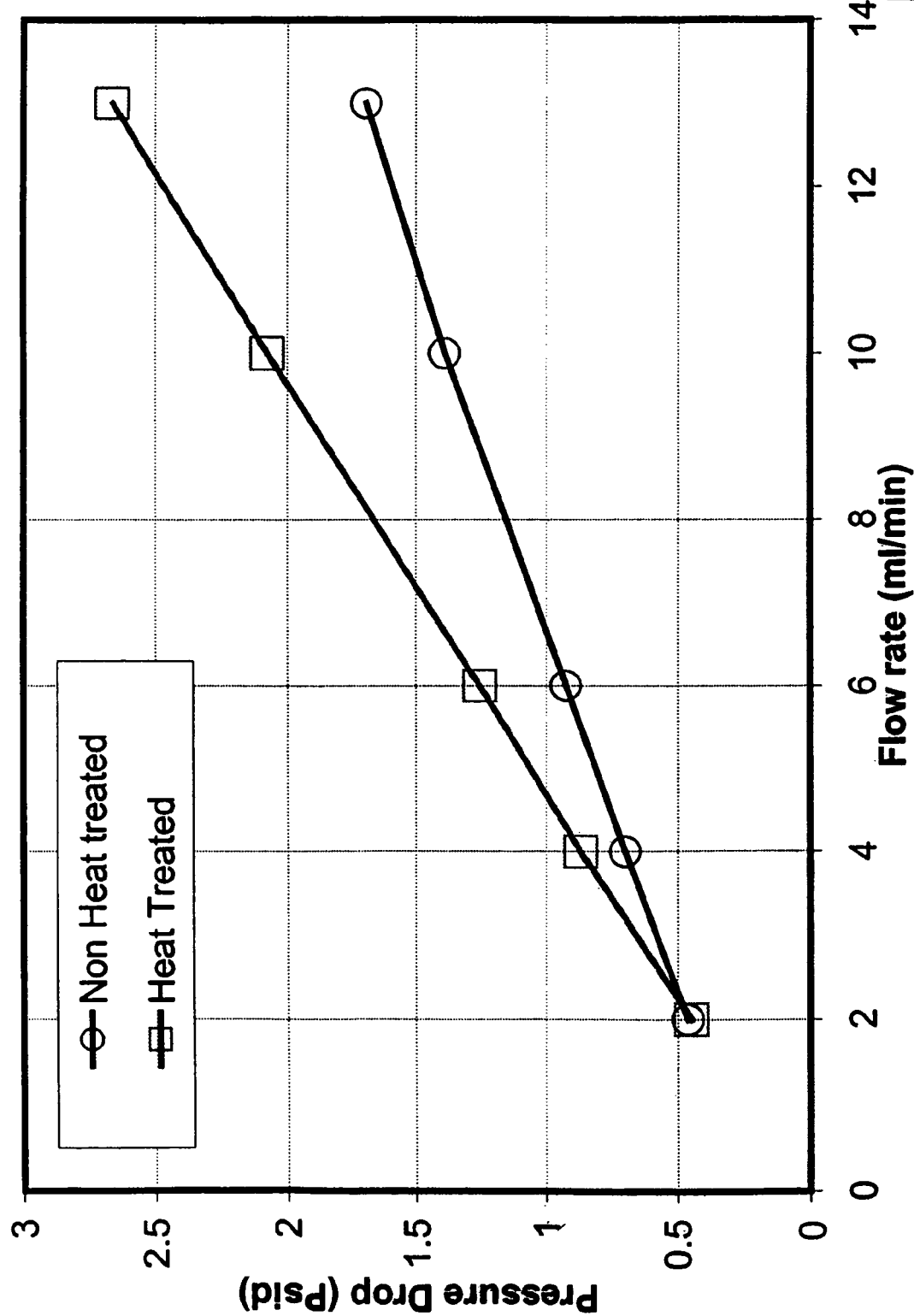
FIG. 29 is a plot of pressure drop versus flow rate for the porous substrates tested in Example 1.

One of the methods to characterize the heat treatment effect on the pore size and number is to conduct permeability tests using water. Using the same flow rate, water is pumped through the heat-treated porous substrate and through an untreated porous substrate. Different pressure drop curves are obtained as shown in FIG. 29. The heat-treated substrate has a higher pressure drop than that of untreated substrate. In this example, the average pore size decreases from 0.5 to 0.44 micron while the inter-pore distance increases from 0.5 to 0.6 micron.

A moisturizing lotion having the formulation indicated below is prepared using the microchannel device.

| | Parts by Wt. |
|---|---|
| First Liquid (Continuous Aqueous) | |
| Water | 82.90 |
| Carbopol 934 (a product supplied by BF Goodrich/Harris and Ford identified as a resin) | 0.20 |
| Na2 EDTA (a product supplied by Dow Chemical Company) | 0.05 |
| Glycerine USP (a product supplied by Humco) | 4.00 |
| Second Liquid (Discontinuous Oil) | |
| Stearic Acid | 2.00 |
| Cetyl Alcohol | 0.50 |
| Glyceryl Monostearate | 0.20 |
| Ethylene Glycol Monostearate | 0.30 |
| Propylparaben | 0.10 |
| Methylparaben | 0.20 |
| Mineral Oil | 7.00 |

-continued

| | Parts by Wt. |
|---|---|
| Silicone Fluid DC200 (a product supplied by Dow Corning identified as a silicone fluid) | 1.00 |
| Tween 20 (a product supplied by Uniqema Americas (ICI) identified as a surfactant) | 0.50 |
| Triethanolamine | 0.90 |

The following process steps are used:
1. All ingredients in the Second Liquid are mixed in a beaker and heated to 75° C. The triethanolamine is added last. The Second Liquid is then maintained at 75° C. in the oil phase reservoir.
2. Prepare the First Liquid by dispersing the Carbopol 934 in the water and heating to 75° C. The remaining ingredients for the First Liquid are then added. The First Liquid is maintained at 75° C. in the reservoir that is connected to the continuous phase liquid pump.
3. The heating powers of the system for all components are adjusted and stabilized at 75±10° C.
4. The continuous phase liquid pump is activated and set for a flow rate of 2.5 l/min.
5. The oil pump is activated and set for a flow rate of 2.5 ml/min. The pressure drop across the porous substrate is maintained at 10-20 psia.
6. The First Liquid is recirculated until the desired amount of the Second Liquid is mixed with the First Liquid.
7. The product emulsion is cooled to a temperature below 38° C. by placing the reservoir in a cold water/ice bath or by turning on a cooling coil built in the reservoir.

Figure 30:
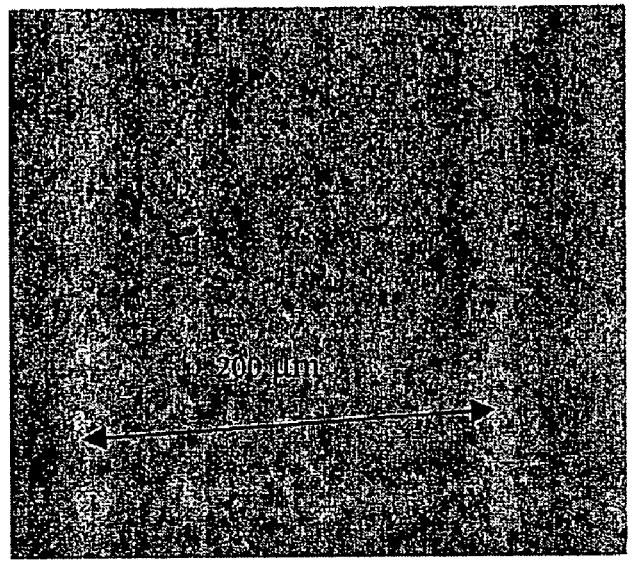
FIGS. 30 and 31 are microscopic images of emulsions made in Example 1.
Figure 31:
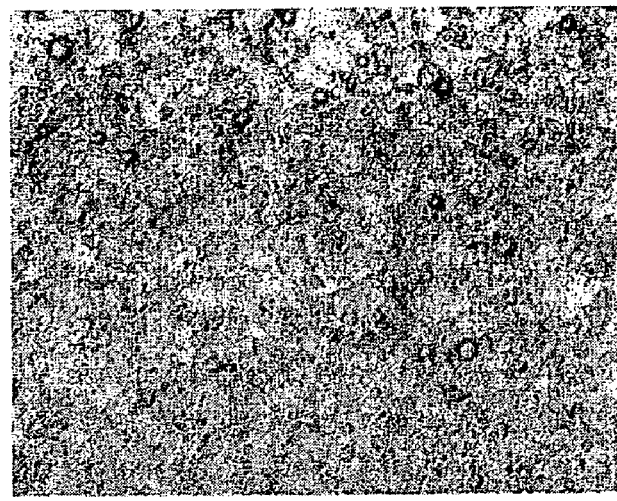

FIGS. 30 and 31 are microscopic images at a magnification of 100 for the foregoing emulsion for two different size ranges. FIG. 30. shows a droplet size from about 0.5 to about 2 microns using the heat treated porous substrate of pore size 0.5 micron at a First Liquid flow rate of 2.0 standard liters per minute (SLPM). FIG. 31 shows a droplet size from about 1 to about 8 microns using the heat treated porous substrate of pore size 0.5 micron at a First Liquid flow rate of 0.5 SLPM.

While the invention has been explained in relation to specific embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:
1. A process for making an emulsion, comprising:
flowing a first liquid through at least one first liquid manifold into a plurality of process microchannels, each process microchannel having at least one wall with at least one apertured section;
flowing a second liquid through at least one second liquid manifold into a plurality of liquid channels adjacent to the process microchannels and through the apertured sections into the process microchannels in contact with the first liquid to form the emulsion, the process microchannels and liquid channels being aligned side by side or stacked one above another, the first liquid forming a continuous phase, the second liquid forming a discontinuous phase dispersed in the continuous phase.
2. The process of claim 1 wherein heat is exchanged between the process microchannel and a heat exchanger.

3. The process of claim 2 wherein the heat exchanger comprises at least one heat exchange channel.

4. The process of claim 3 wherein the process microchannel exchanges heat with a heat exchange fluid flowing through the heat exchange channel.

5. The process of claim 4 wherein the heat exchange fluid undergoes a phase change as it flows through the heat exchange channel.

6. The process of claim 4 wherein an endothermic process is conducted in the heat exchange channel.

7. The process of claim 4 wherein an exothermic process is conducted in the heat exchange channel.

8. The process of claim 4 wherein the heat exchange fluid comprises air, steam, liquid water, carbon monoxide, carbon dioxide, gaseous nitrogen, liquid nitrogen, a gaseous hydrocarbon or a liquid hydrocarbon.

9. The process of claim 4 wherein the heat exchange fluid comprises the first liquid, the second liquid, or a mixture of the first liquid and the second liquid.

10. The process of claim 3 wherein the heat exchange channel has an internal dimension perpendicular to the flow of heat exchange fluid through the heat exchange channel of up to about 50 mm.

11. The process of claim 3 wherein the heat exchange channel has an internal dimension perpendicular to the flow of heat exchange fluid through the heat exchange channel of up to about 10 mm.

12. The process of claim 3 wherein the heat exchange channel has an internal dimension perpendicular to the flow of heat exchange fluid through the heat exchange channel of up to about 2 mm.

13. The process of claim 3 wherein the heat exchange channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; or a combination of two or more thereof.

14. The process of claim 1 wherein the second liquid flows from a liquid channel through the apertured section.

15. The process of claim 14 wherein heat is exchanged between the process microchannel and a heat exchanger, the liquid channel and a heat exchanger, or both the process microchannel and the liquid channel and a heat exchanger.

16. The process of claim 15 wherein the heat exchanger comprises an electric heating element, resistance heater and/or non-fluid cooling element.

17. The process of claim 16 wherein the electric heating element, resistance heater and/or non-fluid cooling element is adjacent to the process microchannel and/or liquid channel.

18. The process of claim 16 wherein the electric heating element, resistance heater and/or non-fluid cooling element is built into one or more walls of the process microchannel and/or liquid channel.

19. The process of claim 16 wherein one or more walls of the process microchannel and/or liquid channel are formed from the electric heating element, resistance heater and/or non-fluid cooling element.

20. The process of claim 15 wherein the heat exchanger is adjacent to the process microchannel and/or liquid channel.

21. The process of claim 15 wherein the heat exchanger is remote from the process microchannel and/or liquid channel.

22. The process of claim 14 wherein the liquid channel has an internal dimension perpendicular to the flow of liquid through the liquid channel of up to about 100 cm.

23. The process of claim 14 wherein the liquid channel has an internal dimension perpendicular to the flow of liquid through the liquid channel of about 0.05 mm to about 10 mm.

24. The process of claim 14 wherein the liquid channel has an internal dimension perpendicular to the flow of liquid through the liquid channel of about 0.05 to about 2 mm.

25. The process of claim 14 wherein the liquid channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; or a combination of two or more thereof.

26. The process of claim 1 wherein the second liquid flows in a liquid channel, the liquid channel having another wall with another apertured section, the process further comprising:
flowing a third liquid through the another apertured section in contact with the second liquid to form a liquid mixture; and
flowing the liquid mixture through the apertured section into the process microchannel in contact with the first liquid.

27. The process of claim 26 wherein the third liquid flows from another liquid channel through the another apertured section.

28. The process of claim 27 wherein the another liquid channel has an internal dimension perpendicular to the flow of liquid through the liquid channel of up to about 100 cm.

29. The process of claim 27 wherein the another liquid channel has an internal dimension perpendicular to the flow of liquid through the liquid channel of about 0.05 mm to about 10 mm.

30. The process of claim 27 wherein the another liquid channel has an internal dimension perpendicular to the flow of liquid through the liquid channel of about 0.05 to about 2 mm.

31. The process of claim 27 wherein the another liquid channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; or a combination of two or more thereof.

32. The process of claim 26 wherein the liquid mixture is dispersed as a discontinuous phase in the first liquid.

33. The process of claim 26 wherein the liquid mixture comprises another emulsion.

34. The process of claim 26 wherein the third liquid is dispersed in the second liquid.

35. The process of claim 26 wherein at least part of the second liquid is in the form of droplets dispersed in the first liquid, and at least part of the third liquid is in the form of droplets encapsulated within the droplets of the second liquid.

36. The process of claim 26 wherein the third liquid comprises water.

37. The process of claim 26 wherein at least one heat exchange channel is adjacent to the process microchannel and/or liquid channel, a heat exchange fluid flows through the heat exchange channel, the heat exchange fluid comprising the first liquid, second liquid and/or third liquid.

38. The process of claim 26 wherein the emulsion comprises a water-in-oil-in-water emulsion.

39. The process of claim 1 wherein the process microchannel comprises two or more apertured sections and separate second liquids flow through each of the apertured sections.

40. The process of claim 39 wherein the separate second liquids flowing through each of the apertured sections have different compositions.

41. The process of claim 40 with a coating overlying at least part of the sheet or plate and filling part of the apertures.

42. The process of claim 40 wherein the sheet or plate is heat treated.

43. The process of claim 39 wherein the separate second liquids flowing through each of the apertured sections have different properties.

44. The process of claim 1 wherein the first liquid and the second liquid contact each other in a mixing zone in the process microchannel.

45. The process of claim 44 wherein heat is exchanged between a heat exchanger and at least part of the process microchannel in the mixing zone.

46. The process of claim 44 wherein heat is exchanged between a heat exchanger and at least part of the process microchannel upstream of the mixing zone.

47. The process of claim 44 wherein heat is exchanged between a heat exchanger and at least part of the process microchannel downstream of the mixing zone.

48. The process of claim 44 wherein the emulsion is quenched in the process microchannel downstream of the mixing zone.

49. The process of claim 44 wherein the process microchannel has a restricted cross section in the mixing zone.

50. The process of claim 1 wherein the process microchannel has walls that are spaced apart and apertured sections in each of the spaced apart walls, the second liquid flowing through each of apertured sections into the process microchannel.

51. The process of claim 50 wherein the apertured sections in each of the spaced apart walls comprise a plurality of apertures, the apertures in the apertured section of one of the walls being aligned directly opposite the apertures in the apertured section of the other wall.

52. The process of claim 50 wherein the apertured sections in each of the spaced apart walls comprise a plurality of apertures, at least some of the apertures in the apertured section of one of the walls being offset from being aligned directly with the apertures in the apertured section of the other wall.

53. The process of claim 1 wherein the process microchannel is circular and is positioned between a circular disk and an apertured section, the circular disk rotating about its axis, the first liquid flowing through a center opening in the apertured section into the process microchannel onto the rotating disk, the second liquid flowing through the apertured section into the process microchannel where it contacts and mixes with the first liquid to form the emulsion, the emulsion flowing radially outwardly on the rotating disk.

54. The process of claim 53 wherein the second liquid flows from a liquid channel adjacent to the process microchannel, the liquid channel being formed from parallel spaced sheets or plates, the apertured section being in one of the sheets or plates.

55. The process of claim 1 wherein the process microchannel is formed from parallel spaced sheets, plates or a combination of such sheets and plates.

56. The process of claim 55 wherein the second liquid flows from a liquid channel through the apertured section into the process microchannel, the liquid channel being formed from parallel spaced sheets or plates, the liquid channel being adjacent to the process microchannel.

57. The process of claim 55 wherein the first liquid and second liquid exchange heat with a heat exchange channel, the heat exchange channel being formed from parallel spaced sheets or plates, the heat exchange channel being adjacent to the process microchannel, the liquid channel, or both the process microchannel and the liquid channel.

58. The process of claim 1 wherein the process is conducted in a microchannel mixer, the microchannel mixer comprising a plurality of the process microchannels, the process microchannels having walls with apertured sections and adjacent liquid channels, the second liquid flowing from the liquid channels through the apertured sections into the process microchannels in contact with the first liquid, the process microchannels and liquid channels being formed from parallel spaced sheets or plates, the process microchannels and liquid channels being adjacent to each other and aligned in interleaved side-by-side vertically oriented planes or interleaved horizontally oriented planes stacked one above another.

59. The process of claim 58 wherein the microchannel mixer further comprises a plurality of heat exchange channels formed from parallel spaced sheets or plates, the heat exchange channels being adjacent to the process microchannels, the liquid channels, or both the process microchannels and the liquid channels.

60. The process of claim 1 wherein the second liquid flows from a liquid channel through the apertured section into the process microchannel, the process microchannel and the liquid channel comprising circular tubes aligned concentrically.

61. The process of claim 60 wherein the process microchannel is in an annular space and the liquid channel is in the center space or an adjacent annular space.

62. The process of claim 60 wherein the process microchannel is in the center space and the liquid channel is in an adjacent annular space.

63. The process of claim 1 wherein the process is conducted in a microchannel mixer, the microchannel mixer comprising a plurality of the process microchannels wherein separate emulsions are formed in each of the process microchannels, the emulsions formed in at least two of the process microchannels being different from each other.

64. The process of claim 63 wherein the emulsions formed in at least two of the process microchannels are different in composition.

65. The process of claim 63 wherein the emulsions formed in at least two of the process microchannels have one or more different physical properties.

66. The process of claim 1 wherein the apertured section is made from a porous material.

67. The process of claim 66 wherein the porous material is metallic.

68. The process of claim 1 wherein the emulsion comprises at least one emulsifier and/or surfactant.

69. The process of claim 68 wherein the emulsifier and/or surfactant comprises an alkanolamine, alkylaryl sulfonate, amine oxide, carboxylated alcohol ethoxylate, ethoxylated alcohol, ethoxylated alkyl phenol, ethoxylated amine, ethoxylated amide, ethoxylated fatty acid, ethoxylated fatty esters, ethoxylated fatty oil, fatty ester, glycerol ester, glycol ester, sorbitan ester, imidazoline derivative, lecithin, lecithin derivative, lignin, lignin derivative, monoglyceride, monoglyceride derivative, olefin sulfonate, phosphate ester, phosphate ester derivative, propoxylated fatty acid, ethoxylated fatty acid, propoxylated alcohol or alkyl phenol, ethoxylated alcohol or alkyl phenol, sorbitan derivative, sucrose ester, sulfonate of dodecyl or tridecyl benzene, naphthalene sulfonate, petroleum sulfonate, tridecyl or dodecyl benzene sulfonic acid, sulfosuccinate, sulfosuccinate derivative, or mixture of two or more thereof.

70. The process of claim 1 wherein the process microchannel is in an emulsion forming unit comprising a first process microchannel, a second process microchannel, and a liquid channel positioned between the first process microchannel and the second process microchannel, each process microchannel having a wall with an apertured section, the first liquid flowing through the first process microchannel and the second process microchannel, the second liquid flowing from the liquid channel through the apertured section in the first process microchannel in contact with the first liquid and through the apertured section in the second process microchannel in contact with the first liquid.

71. The process of claim 1 wherein the process microchannel has a mixing zone adjacent to the apertured section and a non-apertured region extending from the entrance to the process microchannel to the mixing zone.

72. The process of claim 1 wherein the apertured section comprises a sheet or plate with a plurality of apertures in the sheet or plate.

73. The process of claim 1 wherein the apertured section comprises a relatively thin sheet overlying a relatively thick sheet or plate, the relatively thin sheet containing a plurality of relatively small apertures, and the relatively thick sheet or plate containing a plurality of relatively large apertures, the relatively small apertures being aligned with the relatively large apertures sufficiently to permit liquid to flow from the relatively large apertures through the relatively small apertures.

74. The process of claim 1 wherein the apertured section has a wall thickness and a length along the flow path of the first liquid flowing through the process microchannel, the ratio of the wall thickness to the length along the flow path being in the range from about 0.001 to about 1.

75. The process of claim 1 wherein the apertured section is made from a porous material, the surface of the porous material being treated by filling the pores on the surface with a liquid filler, solidifying the filler, grinding and/or polishing the surface, and removing the filler.

76. The process of claim 1 wherein the discontinuous phase is in the form of droplets having a volume-based mean diameter in the range of up to about 200 microns.

77. The process of claim 1 wherein the discontinuous phase comprises droplets having a volume-based mean diameter in the range up to about 200 microns, and a span in the range from about 0.01 to about 10.

78. The process of claim 1 wherein the first liquid comprises water.

79. The process of claim 1 wherein the second liquid comprises an organic liquid.

80. The process of claim 1 wherein the process microchannel has an internal dimension perpendicular to the flow of liquid through the process microchannel of up to about 50 mm.

81. The process of claim 1 wherein the process microchannel has an internal dimension perpendicular to the flow of liquid through the process microchannel of up to about 10 mm.

82. The process of claim 1 wherein the process microchannel has an internal dimension perpendicular to the flow of liquid through the process microchannel of up to about 2 mm.

83. The process of claim 1 wherein the process microchannel is made of a material comprising: steel; monel; inconel; aluminum; titanium; nickel; copper; brass; an alloy of any of the foregoing metals; a polymer; ceramics; glass; a composite comprising a polymer and fiberglass; quartz; silicon; or a combination of two or more thereof.

84. The process of claim 1 wherein the second liquid flows from a liquid channel through the apertured section.

85. The process of claim 1 wherein the emulsion is cooled to room temperature within a time period of up to about 10 minutes.

86. The process of claim 1 wherein the emulsion is filtered.

87. The process of claim 1 wherein the emulsion comprises an oil-in-water emulsion.

88. The process of claim 1 wherein the emulsion comprises at least one organic liquid.

89. The process of claim 1 wherein the emulsion comprises at least one liquid hydrocarbon.

90. The process of claim 1 wherein the emulsion comprises at least one natural oil, synthetic oil, or mixture thereof.

91. The process of claim 1 wherein the emulsion comprises at least one liquid derived from a vegetable source, a mineral source, or mixture thereof.

92. The process of claim 1 wherein the emulsion comprises at least one normally liquid hydrocarbon fuel.

93. The process of claim 1 wherein the emulsion comprises at least one fatty alcohol, fatty acid ester, or a mixture thereof.

94. The process of claim 1 wherein the emulsion comprises: one or more branched primary alcohols of about 6 to about 22 carbon atoms; one or more linear and/or branched fatty alcohol carbonates of about 6 to about 22 carbon atoms; one or more Guerbet carbonates based on one or more fatty alcohols of about 6 to about 22 carbon atoms; one or more dialkyl naphthalates wherein each alkyl group contains 1 to about 12 carbon atoms; one or more linear or branched, symmetrical or nonsymmetrical dialkyl ethers containing about 6 to about 22 carbon atoms per alkyl group; one or more ring opening products of epoxidized fatty acid esters of about 6 to about 22 carbon atoms with polyols containing 2 to about 10 carbon atoms and 2 to about 6 hydroxyl groups; or a mixture of two or more thereof.

95. The process of claim 1 wherein the emulsion comprises one or more: UV protection factors; waxes; consistency factors; thickeners; superfatting agents; stabilizers; cationic, anionic, zwitterionic, amphoteric or nonionic polymers; silicone compounds; fats; waxes; lecithins; phospholipids; biogenic agents; antioxidants; deodorants; antiperspirants; antidandruff agents; swelling agents; insect repellents; self-tanning agents; tyrosine inhibitors; solubilizers; preservatives; perfume oils; or dyes; or a mixture of two or more thereof.

96. The process of claim 1 wherein solids are dispersed in the emulsion.

97. The process of claim 1 wherein pigment is dispersed in the emulsion.

98. The process of claim 1 wherein a catalyst is dispersed in the emulsion.

99. The process of claim 1 wherein optical or thermal-optical features of the emulsion are adjusted in the process microchannel.

100. The process of claim 1 wherein the process produces at least 1 liter of emulsion per minute.

101. The process of claim 1 wherein the process produces at least 1 liter of emulsion per second.

102. The process of claim 1 wherein the process is conducted in a microchannel mixer, the microchannel mixer comprising at least two of the process microchannels.

103. The process of claim 1 wherein the process is conducted in a microchannel mixer, the microchannel mixer comprising at least about 1000 of the process microchannels.

104. The process of claim 1 wherein the process is conducted in a microchannel mixer, the microchannel mixer comprising at least about 10 of the process microchannels.

105. The process of claim 1 wherein the process is conducted in a microchannel mixer, the microchannel mixer comprising at least about 100 of the process microchannels.

106. The process of claim 1 wherein heat exchange channels are adjacent to the process microchannels and/or liquid channels, and at least one heat exchange manifold is connected to the heat exchange channels, a heat exchange fluid flowing through the at least one heat exchange manifold to the heat exchange channels.

107. A process for making an emulsion in a microchannel mixer, the microchannel mixer comprising a plurality of emulsion forming units aligned side-by-side or stacked one above another, each emulsion forming unit comprising a process microchannel and an adjacent liquid channel, the process microchannel and adjacent liquid channel having a common wall with an apertured section in the common wall, the apertured section being suitable for flowing a liquid from the liquid channel through the apertured section into the process microchannel, each process microchannel and liquid channel being formed from parallel spaced sheets, plates, or a combination of such sheets and plates, the process comprising:

flowing a first liquid in the process microchannel;

flowing a second liquid from the liquid channel through the apertured section into the process microchannel; and mixing the first liquid and the second liquid in the process microchannel to form the emulsion.

108. The process of claim 107 wherein each emulsion forming unit further comprises a heat exchange channel adjacent to the process microchannel, the liquid channel, or both the process microchannel and the liquid channel.

109. The process of claim 108 wherein the microchannel mixer further comprises a heat exchange manifold, a heat exchange fluid flows from the heat exchange manifold through the heat exchange channel to the heat exchange manifold.

110. The process of claim 107 wherein the first liquid flows through a header into the process microchannel.

111. The process of claim 107 wherein the second liquid flows through a header into the liquid channel.

112. The process of claim 107 wherein the emulsion flows out of the process microchannel through a footer.

* * * * *

(12) EX PARTE REEXAMINATION CERTIFICATE (8391st)
United States Patent
Qiu et al.

(10) Number: US 7,307,104 C1
(45) Certificate Issued: Jul. 5, 2011

(54) PROCESS FOR FORMING AN EMULSION USING MICROCHANNEL PROCESS TECHNOLOGY

(75) Inventors: Dongming Qiu, Dublin, OH (US); Anna Lee Tonkovich, Marysville, OH (US); Laura J. Silva, Dublin, OH (US); Richard Q. Long, Columbus, OH (US); Barry L. Yang, Dublin, OH (US); Kristina Marie Trenkamp, Dublin, OH (US); Jennifer Anne Freeman, Columbus, OH (US)

(73) Assignee: Velocys, Inc., Plain City, OH (US)

Reexamination Request:
No. 90/009,346, Jan. 21, 2009

Reexamination Certificate for:
Patent No.: 7,307,104
Issued: Dec. 11, 2007
Appl. No.: 10/844,061
Filed: May 12, 2004

Related U.S. Application Data

(63) Continuation-in-part of application No. 10/440,056, filed on May 16, 2003, now Pat. No. 7,485,671.
(60) Provisional application No. 60/548,152, filed on Feb. 25, 2004.

(51) Int. Cl.
*B01F 3/08* (2006.01)
*B01F 17/00* (2006.01)
*B01F 17/38* (2006.01)
*B01F 5/06* (2006.01)

(52) U.S. Cl. ............... 516/54; 516/21; 516/22; 516/23; 516/928

(58) Field of Classification Search .......... None
See application file for complete search history.

(56) References Cited

U.S. PATENT DOCUMENTS

| | | |
|---|---|---|
| 3,489,690 A | 1/1970 | Lachampt et al. ............ 252/308 |
| 3,882,049 A | 5/1975 | Bertolacini et al. |
| 3,953,591 A | 4/1976 | Snyder ......................... 424/80 |
| 3,972,837 A | 8/1976 | Acres et al. |
| 4,070,450 A | 1/1978 | Barner et al. .................. 424/59 |
| 4,089,810 A | 5/1978 | Diwell et al. |
| 4,096,095 A | 6/1978 | Cairns |
| 4,289,652 A | 9/1981 | Hunter et al. |
| 5,248,251 A | 9/1993 | Dalla Betta et al. |
| 6,040,266 A | 3/2000 | Fay, III et al. |
| 6,155,710 A | 12/2000 | Nakajima et al. ........ 366/167.1 |
| 6,203,791 B1 | 3/2001 | Protopapa et al. ........ 424/94.64 |
| 6,281,254 B1 | 8/2001 | Nakajima et al. ............. 516/53 |
| 6,387,301 B1 | 5/2002 | Nakajima et al. ............ 264/4.4 |
| 6,440,895 B1 | 8/2002 | Tonkovich et al. |
| 6,576,023 B2 | 6/2003 | Nakajima et al. ............. 264/14 |
| 7,378,473 B2 | 5/2008 | Torii et al. ..................... 526/88 |

FOREIGN PATENT DOCUMENTS

| | | |
|---|---|---|
| DE | 246257 | 6/1987 |
| DE | 3926466 | 2/1991 |
| EP | 1 125 630 A2 | 8/2001 |
| EP | 1 197 262 A2 | 4/2002 |
| EP | 1 197 262 A3 | 2/2003 |
| EP | 1102628 | 11/2006 |
| EP | 1875959 | 10/2009 |
| GB | 1531134 | 11/1978 |
| GB | 2077136 | 12/1981 |
| JP | 11-165062 A * | 6/1999 |
| JP | 2000-84384 | 3/2000 |
| JP | 2003-71261 | 3/2003 |
| JP | 2004-237177 | 8/2004 |
| JP | 2004-268029 | 9/2004 |
| JP | 2006-505387 | 2/2006 |
| WO | 9421372 | 9/1994 |
| WO | 9700442 | 1/1997 |
| WO | 9828073 | 7/1998 |
| WO | 98/30205 | 7/1998 |
| WO | 9838147 | 9/1998 |
| WO | 9916542 | 4/1999 |
| WO | 0006301 | 2/2000 |
| WO | 02/28769 | 11/2002 |
| WO | 03006149 | 1/2003 |
| WO | 2004026457 | 1/2004 |
| ZA | 855317 | 7/1985 |

OTHER PUBLICATIONS

Nakajima, "Novel microchannel system for monodispersed microspheres," RIKEN Review, No. 36, Jun. 2001: Focused on Science and Technology in Micro/Nano Scale, pp. 21–23.*

Kawakatsu et al, Effect of Microchannel Structure on Droplet Size During Crossflow Microchannel Emulsification, Journal of Surfactants and Detergents, vol. 3, No. 3, pp. 295–302, Jul. 2000.*

U.S. Office Action, U.S. Appl. No. 11/876,850, mailed Dec. 27, 2010.

Chinese Office Action, Application No. 200480019998.4, issued Nov. 8, 2010.

Decision to Grant, Japanese Application 2006–532956, dispatched Sep. 28, 2010.

Office Action, Canadian Patent Application 2,526,965 dated Jun. 15, 2010.

Office Action, European Patent Application 04 751 902.0, dated Mar. 24, 2006.

Office Action, European Patent Application 07020713.9/ 1875959, dated Jul. 8, 2010.

Office Action, Chinese Application 200480019998.4, issued Apr. 14, 2010.

Office Action, Japanese Application 2006–532956, issued Jun. 1, 2010.

(Continued)

*Primary Examiner*—Carlos Lopez

(57) ABSTRACT

The disclosed invention relates to a process for making an emulsion. The process comprises: flowing a first liquid through a process microchannel, the process microchannel having a wall with an apertured section; flowing a second liquid through the apertured section into the process microchannel in contact with the first liquid, the first liquid forming a continuous phase, the second liquid forming a discontinuous phase dispersed in the continuous phase.

OTHER PUBLICATIONS

Iglesia: "Design, synthesis, and use of cobalt–based Fischer–Tropsch synthesis catalysts", Applied Catalysis A: General 161 (1997); pp. 59–78.
China Office Action, Application No. 200480019998.4, issued Oct. 30, 2009.
European Search Report, Application No. 07020713.9, dated Sep. 18, 2009.
Nisisako et al.; "Droplet formation in a microchannel network", Lab Chip; 2002, 2, pp. 24–26.
Office Action, U.S. Appl. No. 10/440,056, mailed Oct. 11, 2005.
Office Action, U.S. Appl. No. 10/440,056, mailed Apr. 6, 2006.
Office Action, U.S. Appl. No. 10/440,056, mailed Jul. 10, 2006.
Office Action, U.S. Appl. No. 10/440,056, mailed Dec. 29, 2006.
Office Action, U.S. Appl. No. 10/440,056, mailed Jul. 12, 2007.
Office Action, U.S. Appl. No. 10/440,056, mailed Jan. 14, 2008.
Office Action, U.S. Appl. No. 10/440,056, mailed Jun. 16, 2008.
Office Action, U.S. Appl. No. 10/440,056, mailed Sep. 30, 2008.
Office Action, U.S. Appl. No. 10/440,056, mailed Oct. 14, 2008.
Notice of Allowance, U.S. Appl. No. 10/440,056, mailed Dec. 3, 2008.
Partial European Search Report, Application No. 07020713.9, dated Jun. 17, 2009.
Cybulski et al.; "Monoliths in Heterogeneous Catalysis", Catal. Rev. –Sci. Eng., 36(2), 179–270 (1994).
Bennett et al.; "Microchannel cooled heatsinks for high average power laser diode arrays", SPIE, vol. 1865; 1993; pp. 144–153.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 41, 58, 60-62 and 107-112 are cancelled.
Claims 1, 26, and 59 are determined to be patentable as amended.
Claims 2-25, 27-40, 42-57, and 63-106 dependent on an amended claim, are determined to be patentable.
New claim 113 is added and determined to be patentable.

1. A process for making an emulsion, comprising:
   flowing a first liquid through at least one first liquid manifold into a plurality of process microchannels, each process microchannel having at least one wall with at least one apertured section;
   flowing a second liquid through at least one second liquid manifold into a plurality of liquid channels adjacent to the process microchannels and through the apertured sections into the process microchannels in contact with the first liquid to form the emulsion, the process microchannels and liquid channels being aligned side by side or stacked one above another, the first liquid forming a continuous phase, the second liquid forming a discontinuous phase dispersed in the continuous phase;
   *wherein the process is conducted in a microchannel mixer, the microchannel mixer comprising a plurality of the process microchannels, the process microchannels having walls with apertured sections and adjacent liquid channels, the second liquid flowing from the liquid channels through the apertured sections into the process microchannels in contact with the first liquid, the process microchannels and liquid channels being formed from parallel spaced sheets or plates, the process microchannels and liquid channels being adjacent to each other and aligned in interleaved side-by-side vertically oriented planes or interleaved horizontally oriented planes stacked one above another.*

26. [The process of claim 1] *A process for making an emulsion, comprising:*
    flowing a first liquid through at least one first liquid manifold into a plurality of process microchannels, each process microchannel having at least one wall with at least one apertured section;
    flowing a second liquid through at least one second liquid manifold into a plurality of liquid channels adjacent to the process microchannels and through the apertured sections into the process microchannels in contact with the first liquid to form the emulsion, the process microchannels and liquid channels being aligned side by side or stacked one above another, the first liquid forming a continuous phase, the second liquid forming a discontinuous phase dispersed in the continuous phase;
    wherein the second liquid flows in a liquid channel, the liquid channel having another wall with another apertured section, the process further comprising:
    flowing a third liquid through the another apertured section in contact with the second liquid to form a liquid mixture; and
    flowing the liquid mixture through the apertured section into the process microchannel in contact with the first liquid.

59. The process of claim [58] *1* wherein the microchannel mixer further comprises a plurality of heat exchange channels formed from parallel spaced sheets or plates, the heat exchange channels being adjacent to the process microchannels, the liquid channels, or both the process microchannels and the liquid channels.

*113. A process for making an emulsion, comprising:*
   *flowing a first liquid through at least one first liquid manifold into a plurality of process microchannels, each process microchannel having at least one wall with at least one apertured section;*
   *flowing a second liquid through at least one second liquid manifold into a plurality of liquid channels adjacent to the process microchannels and through the apertured sections into the process microchannels in contact with the first liquid to form the emulsion, the process microchannels and liquid channels being aligned side by side or stacked one above another, the first liquid forming a continuous phase, the second liquid forming a discontinuous phase dispersed in the continuous phase;*
   *wherein the process microchannel comprises two or more apertured sections and seperate second liquids flow through each of the apertured sections;*
   *wherein the separate second liquids flowing through each of the apertured sections have different compositions; and*
   *wherein the apertured section comprises a sheet or plate and a plurality of apertures in the sheet or plate with a coating overlying at least part of the sheet or plate and filling part of the apertures.*

\* \* \* \* \*